(12) United States Patent
Maas et al.

(10) Patent No.: US 8,197,514 B2
(45) Date of Patent: Jun. 12, 2012

(54) IMPLANT FOR MUTUAL SUPPORT OF THE SPINOUS PROCESSES OF VERTEBRAL BODIES

(75) Inventors: Allan Maas, Constance (DE); Claudia Vollmer, Liptingen (DE); Alexander Haas, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 589 days.

(21) Appl. No.: 12/372,033

(22) Filed: Feb. 17, 2009

(65) Prior Publication Data

US 2010/0004688 A1 Jan. 7, 2010

(30) Foreign Application Priority Data

Jul. 4, 2008 (DE) .......................... 10 2008 032 685

(51) Int. Cl.
*A61B 17/70* (2006.01)
(52) U.S. Cl. .......................................... 606/248; 606/90
(58) Field of Classification Search .......... 606/247–249, 606/263, 282, 297, 300, 74, 324, 151, 216, 606/217, 218, 232, 310, 313, 326, 327, 53, 606/60, 90, 105; 623/17.14
See application file for complete search history.

(56) References Cited

U.S. PATENT DOCUMENTS

| 5,351,792 | A | * | 10/1994 | Cohen .......................... 190/18 A |
| 5,645,589 | A | * | 7/1997 | Li .................................. 606/60 |
| 6,214,050 | B1 | * | 4/2001 | Huene ......................... 623/17.15 |
| 6,332,883 | B1 | | 12/2001 | Zucherman et al. |
| 7,585,313 | B2 | * | 9/2009 | Kwak et al. ................... 606/249 |
| 7,585,316 | B2 | * | 9/2009 | Trieu ............................. 606/279 |
| 8,012,207 | B2 | * | 9/2011 | Kim ........................... 623/17.11 |
| 2007/0032790 | A1 | * | 2/2007 | Aschmann et al. ............. 606/61 |
| 2007/0225724 | A1 | * | 9/2007 | Edmond ......................... 606/90 |
| 2008/0027438 | A1 | * | 1/2008 | Abdou ............................. 606/61 |
| 2008/0109082 | A1 | | 5/2008 | Fink et al. |
| 2008/0114367 | A1 | * | 5/2008 | Meyer ............................. 606/90 |
| 2008/0300601 | A1 | * | 12/2008 | Fabian et al. ................... 606/90 |

(Continued)

FOREIGN PATENT DOCUMENTS

DE 694 31 348 5/2003

(Continued)

OTHER PUBLICATIONS

International Search Report for Application No. PCT/EP2009/004844 dated Jan. 27, 2011.

(Continued)

*Primary Examiner* — Eduardo C Robert
*Assistant Examiner* — Lynnsy Schneider
(74) *Attorney, Agent, or Firm* — RatnerPrestia

(57) ABSTRACT

An implant includes two implant components, each having at least two adjacent support arms, which are connected to one another at one end by means of a bridge and can be spread apart at their free ends, and at least one of which support arms forms a support surface, such that with the free ends of their support arms both implant components are directed towards the free ends of the support arms of the respective other implant component, and that both implant components have slide faces for the support arms of the respective other implant component which are arranged and shaped such that as the two implant components approach one another, the support arms slide on the slide faces of the respective other implant component, and are pivoted thereby, so that the spacing of the upper and lower support surfaces is thereby increased.

40 Claims, 52 Drawing Sheets

U.S. PATENT DOCUMENTS

2009/0149886 A1 * 6/2009 Zentes et al. .................. 606/249

FOREIGN PATENT DOCUMENTS

| DE | 698 28 711 | 1/2006 |
| DE | 10 2004 047 566 B3 | 5/2006 |
| DE | 10 2004 063 996 | 8/2006 |
| DE | 20 2006 018 978 | 3/2007 |
| DE | 20 2008 009 344 | 10/2008 |
| WO | WO 2006/111174 | 10/2006 |
| WO | WO 2007/127689 | 11/2007 |

OTHER PUBLICATIONS

International Search Report of International Application No. PCT/EP2009/004844. Search Completed Oct. 28, 2009 (w/English language form PCT/ISA/210 to show relevance).

Search Report from the German Patent Office for Priority Patent Application No. DE 10 2008 032 685.2; Date of the Conclusion of the Search, Jun. 8, 2009 (w/English translation of Form PCT/ISA/210.).

* cited by examiner

FIG.28
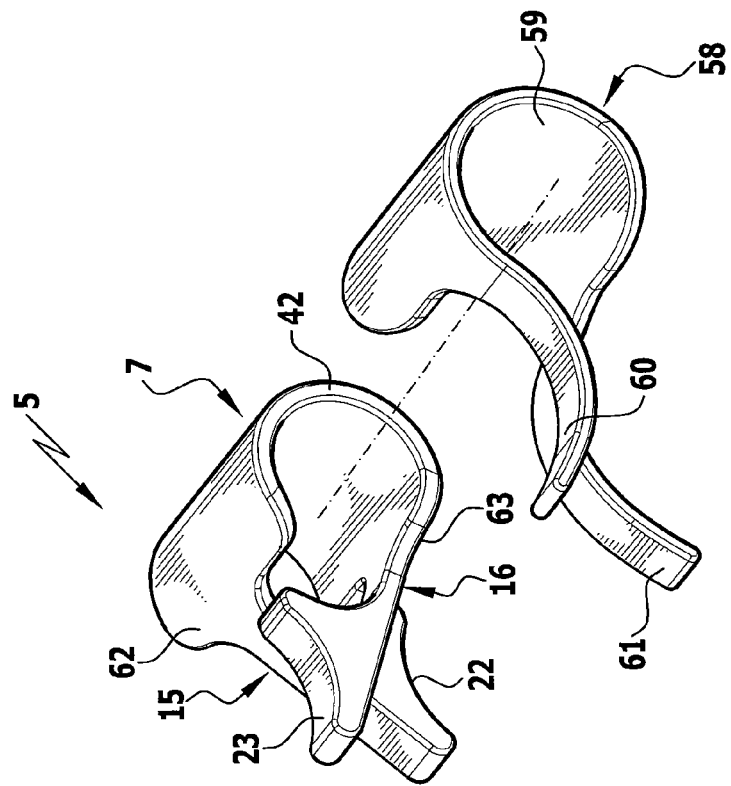
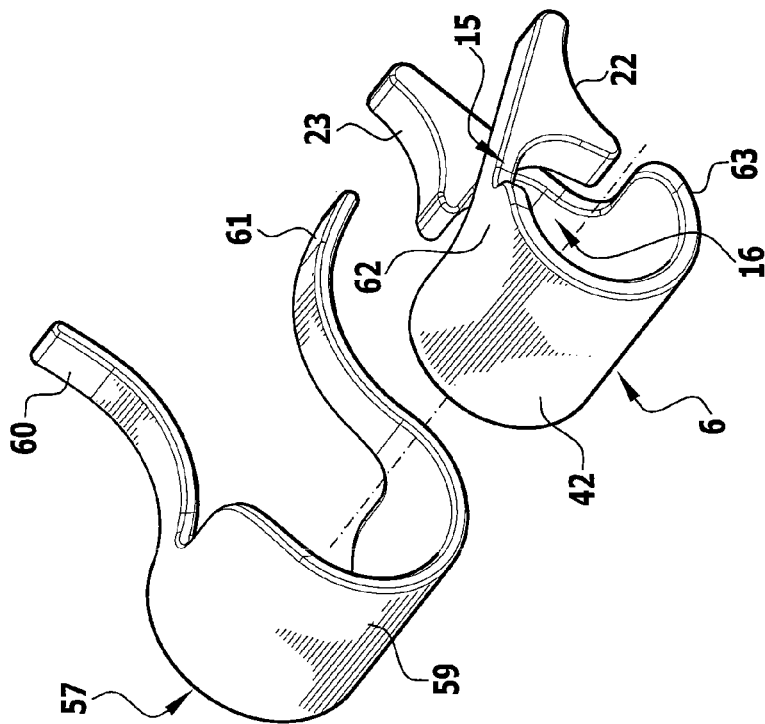

IMPLANT FOR MUTUAL SUPPORT OF THE SPINOUS PROCESSES OF VERTEBRAL BODIES

CROSS-REFERENCE TO RELATED APPLICATIONS

This application claims priority to German Patent Application No. 10 2008 032 685.2, filed on Jul. 4, 2008, which is incorporated herein by reference in its entirety.

FIELD OF THE INVENTION

The invention relates to an implant for mutual support of the spinous processes of two adjacent vertebral bodies with at least one upper support surface for the spinous process of an upper vertebral body and at least one lower support surface for the spinous process of a lower vertebral body, the spacing between which can be increased.

BACKGROUND OF THE INVENTION

Implants for mutual support of the spinous processes of vertebral bodies are inserted into the interstice between the spinous processes of adjacent vertebral bodies and after insertion are then changed in such a way that the support surfaces increase their spacing from one another, so that the spinous processes resting on the support surfaces are thus pushed apart to some extent, e.g. to stabilise the adjacent vertebral bodies or to ease the pressure on the intervertebral space and partially also to pivot the vertebral bodies relative to one another.

It is essential for the insertion that the implants have as low a structural height as possible to enable the implants to be positioned through small access openings, while the spacing of the support surfaces must be increased after insertion to allow the desired distance between the spinous processes to be attained.

SUMMARY OF THE INVENTION

It is an object of the invention to configure an implant of the type described above so that with a relatively simple construction the implantation and the adjustment of the spacing of the support surfaces from one another can be achieved as simply as possible.

This object is achieved according to the invention with an implant of the above-described type in that the implant comprises two implant components, each of which has at least two adjacent support arms, which are joined to one another at one end by means of a bridge and can be spread apart at their free ends, and at least one of which support arms forms one of the support surfaces, that with the free ends of their support arms both implant components are directed towards the free ends of the support arms of the respective other implant component, and that both implant components have slide faces for the support arms of the respective other implant component, against which the support arms of the respective other implant component abut and which are arranged and shaped such that as the two implant components approach one another, the support arms slide on the slide faces of the respective other implant component, and are pivoted thereby, so that the spacing of the upper and lower support surfaces is thereby increased.

Thus, in the implant according to the invention two implant components are pushed towards one another, and thus the support arms of one respective implant component slide onto the slide faces of the respective other implant component and are pivoted or spread apart such that the support surfaces are thus moved away from one another, i.e. the support spacing between the spinous processes is increased. In this way, the implant can be implanted with a low structural height, in which case the two implant components are at a relatively large distance from one another. After implantation the two implant components are pushed towards one another and this necessarily causes the spacing of the support surfaces to increase and the spinous processes abutting against the support surfaces to thus be pressed apart.

It is favourable if the support surfaces are concavely curved, so that when the spinous process is supported in the centre portion of a support surface, this rises at its edge regions on both sides of the spinous process. This shaping also causes the spinous processes to be centred within the support surface and thus simplifies the insertion of the implant.

It is fundamentally possible that only one support arm of an implant component respectively bears a support surface, whereby one support surface is provided on each implant component. In a preferred embodiment, however, it is provided that each implant component has a respective support surface on its two support arms, so that each implant component forms an upper and a lower support surface. In this way, the support is respectively achieved on each spinous process by means of two adjacent support surfaces, wherein respectively one support surface is arranged on one implant component and the other support surface is arranged on the other implant component.

It can be provided that at least one support arm of an implant component is divided into two adjacent support arm sections by a longitudinal slot starting at its free end. It could also be said that each support arm is formed by a pair of adjacent support arms or even by a larger number of individual support arms lying next to one another.

In this case, it is advantageous if support arms or support arm sections of one implant component are arranged in the longitudinal slot between two support arm sections of the other implant component. Thus, in this case, the support arms or support arm sections of the two implant components mesh into one another in the manner of a comb.

In a first preferred embodiment, it is provided that the implant components are configured substantially in a U shape with adjacent support arms, which when the implant components approach one another slide with their inner surfaces on the slide faces of the other implant component and are thus pivoted apart.

In this case, it is favourable if at least one support arm bears a support surface on its outer surface.

In another preferred embodiment, it is provided that the support arms of one implant component run inclined relative to one another, starting from the bridge connecting them, that they cross over one another and that the support arms slide on the slide faces of the other implant component with their outer surfaces and are thus inclined even more steeply relative to one another, wherein as a result of the crossover of the support arms the free ends of the support arms are moved away from one another. Therefore, while in the above-described embodiment the support arms are pivoted apart over their entire length, and thus increase the spacing of the support surfaces, the increase of the spacing of the support surfaces in the last described embodiment is achieved by a more pronounced crossover of the support arms and thus by an increase of the spacing of the support arms in the region of their free ends.

It can also be provided here that at least one support arm bears a support surface on its inner surface.

In the case of the crossed embodiment it is favourable if the outer surface of a support arm of one implant component forms the slide face for a support arm of the other implant component. As a result, the support arms thus slide on one another, the outer surface of the support arms thus respectively forming the slide face, while the inner surface, which is pivoted outwards during sliding, then bears the support surface.

It is particularly advantageous if both implant components of an implant are configured identically. As a result, the implant can be particularly simple to produce. The requirement for this is that the two implant components are mirror-inverted, so that support arms of one implant component can respectively slide on slide faces of the other implant component.

In particular, the implant components are configured in one piece.

In another preferred embodiment it is provided that an implant component consists of two individual parts, which are connected to one another in a hinge-like manner in the region of the bridge.

In particular, on their ends abutting one another both individual parts can respectively bear a locating bead, which run next to one another and are jointly embraced by a clamp and are thereby held next to one another.

It is favourable if the implant component is made from an elastically deformable material.

In a special embodiment it is provided that the implant component has a thickened area in the region of the bridge.

In a further embodiment it can be provided that a core filling the interior of the implant component is fitted between the two support arms and the bridge.

In a preferred embodiment, in the region of the bridge the implant component has at least one through opening for a tie bar pushing the two implant components towards one another. By means of this tie bar the spacing of the implant components can be reduced and this then causes an increase in the spacing of the support surfaces.

In this case, it is favourable if at least one tie bar, which clamps the two implant components against one another, engages through the implant components.

In another preferred embodiment it is provided that a tie bar, which has end pieces abutting externally against the bridges of the two implant components and thus clamps the two implant components against one another, is arranged on one side or on both sides laterally next to the implant components.

In a special embodiment, the tie bar can be encased on the outside by a covering. As a result, the tie bar is shielded from its surroundings, so that an undesirable contact with surrounding tissue can be avoided.

For example, the covering can be in the form of a cover strip.

It is favourable if the tie bar has alternating projections and recessed areas and if a locking element, which can engage between adjacent projections, is disposed on the implant. In this way, after the implant components have been pushed together by engagement of the locking element, the two implant components can be fixed in the position where they are close to one another and are clamped against one another.

This fixture is achieved very simply by the locking element being shifted out of a non-engaged position into an engaged position.

In a particularly preferred embodiment, it is provided that the locking element has an opening for the tie bar with two adjacent regions, a first region of which is so large that the tie bar can be pushed freely in axial direction through this first region with its projections, whereas the second region is only so large that a section of the tie bar lying between adjacent projections can be inserted into it, while a section bearing a projection cannot. Thus, a displacement of the locking element relative to the tie bar is sufficient to bring the locking element out of a release position, in which the tie bar is displaceable through the opening, into a locking position, in which the tie bar is fixed to be axially non-displaceable relative to the locking element.

The projections can be configured in particular as peripheral ribs of the tie bars.

It is favourable if the locking element can pivot around an axis running parallel to the longitudinal axis of the tie bar. Thus, the locking element can be pivoted from the release position into the locking position and vice versa solely by such a pivoting movement.

In a preferred embodiment, it is provided that the locking element can be fixed in a position, in which it engages between adjacent projections of the tie bar, i.e. in its locking position.

In order to fix the locking element in position a cap can be provided, for example, which can be attached to the locking element and a holding element, which is arranged adjacent to this and is held on the tie bar, to engage around the locking element and the holding element. In particular, attachment can be achieved by an elastic snap-on arrangement, so that the locking element and holding element can thus be fixed in a simple manner so that they are non-displaceable relative to one another.

It can be provided that the holding element and the locking element are disposed on one another to be able to pivot relative to one another, e.g. by means of a pivot pin on one of the two parts, which engages into a locating recess of the other part.

In another embodiment it is provided that the implant is arranged in a casing surrounding it, which can be removed at one side from the implant. As a result of this, the insertion of the implant is simplified, parts of the implant that possibly project elastically from it can thus firstly be held in folded form, so that the structural size of the implant is small and contact with surrounding tissue parts is additionally avoided. The casing is removed only after insertion, so that parts of the implant can then be pivoted out or extended.

According to a particularly preferred embodiment it is provided that lateral abutment elements for the spinous process resting on the support surface are arranged on the implant next to the support surfaces. These abutment elements abut laterally against the spinous process resting on the support surface and thus fasten the implant relative to the spinous process.

It is advantageous in this if the abutment elements are respectively part of the implant components.

However, in other embodiments it can also be provided that the abutment elements are separate parts, which are respectively held on an implant component.

It is particularly favourable if the abutment elements are movable or deformable by the relative movement of the two implant components from a starting position, in which they project little or not at all from the implant components, into an end position, in which they project to a greater extent from the implant component. In this way, when the two implant components are pushed together not only is the spacing of the support surfaces increased, but at the same time the abutment elements are also moved out of the starting position into the end position, in which they are laterally supported on the spinous process. However, during implantation, the abutment elements do not project, or project only slightly, beyond the contour of the implant and therefore do not hinder insertion.

In a first preferred embodiment it is provided that an abutment element is formed by a support arm or a support arm section of the implant component, which does not bear a support surface. Therefore, in these embodiments there are support arms of different types, namely support arms that form or bear a support surface and also support arms that form an abutment element.

It is favourable in this case if the support arm or support arm section forming an abutment element is more flexible in configuration than the arm section bearing the support surface.

In another preferred embodiment it is provided that each implant component is surrounded by a U-shaped clamp, which abuts against the outer surface of the implant component and bears webs, which form the abutment elements and are respectively directed towards the other implant component and which abut against slide faces of the other implant component or the clamp held on this, and thus move from the starting position into the end position as the implant components approach one another. This is basically a similar configuration to that in the case of implant components, in which the support arms are displaced as the implant components approach one another, and in this configuration a similar displacement also occurs in the case of the webs, which the U-shaped clamp bears that surrounds the implant component on the outside.

In a further preferred embodiment it is provided that clamping elements, which clamp the two implant components arranged between the clamping elements as they approach one another, are applied respectively against the outer surface of the bridge of the two implant components, and that the clamping elements abut against the outer surface of the bridge with webs forming the abutment elements, which during the approach slide on the outer surface of the bridge and thus move from the starting position into the end position. Thus, in this case the bridges of the implant components form the slide faces for the webs of the clamping elements, which are thus bent outwards when pushed together and form the abutment elements.

In another embodiment it is provided that the abutment elements are held in a wedge fit between the support arms of one implant component and the slide face of the other implant component. In this position the abutment elements are inserted and are then fastened in this position as a result of the implant components being clamped together.

It is favourable in this case if the abutment elements are bent to opposite sides on opposite ends, so that the two ends then form corresponding abutment elements on opposite sides of the implant.

In particular, the abutment elements can be in the form of bands. It is favourable if at least one abutment element has a longitudinal slot. This then results in two web-like sections running parallel to one another on the abutment element.

In this case, it can be provided in particular that a part of an implant component projects into the longitudinal slot and abuts against the side edges of the longitudinal slot. As a result, the abutment element is guided relative to the implant component in the case of a longitudinal displacement, since the part of the implant component projecting into the longitudinal slot acts as a guide element.

In a particular configuration it is provided that the abutment elements bear a thickened portion on one side, by means of which removal of the abutment element between the support arms of one implant component and the abutment surface of the other implant component into the end position is restricted.

A particularly advantageous configuration is one in which it is provided that the abutment elements abut flat against the support arms in the starting position. This results in a particularly low structural height of the entire implant.

In a further preferred embodiment it is provided that a coil spring is inserted into the interior of an implant component between the bridge and the portion of the support arms on the bridge side and with its ends projects out of the interior through openings of the support arms, which form the abutment elements. These resilient ends can be bent over during implantation, so that they do not hinder the insertion. After insertion of the implant these free ends are released and pivot out, and then form the abutment elements abutting against the spinous process.

In a further preferred embodiment the abutment element is displaceably disposed in a guide means of the implant component, projects out of the implant component at one end and at the other end is held on an end piece, which abuts against the outer surface of the implant component. In addition, a tension element is provided, which brings the end pieces closer to one another, thus clamps the implant components against one another and at the same time displaces the abutment element in the guide means out of the starting position into the end position. Thus, in this case the relative displacement of the two implant components is also used to simultaneously displace the abutment element from the starting position into the end position.

In this case, the guide means can be formed by openings in the bridge and in a support arm, through which the abutment element projects.

The following description of preferred embodiments of the invention serves as more detailed explanation in association with the drawings.

BRIEF DESCRIPTION OF THE DRAWINGS

FIG. 28 is an exploded view of the implant of FIG. 27;

DETAILED DESCRIPTION OF EXEMPLARY EMBODIMENTS OF THE INVENTION

Figure 1:
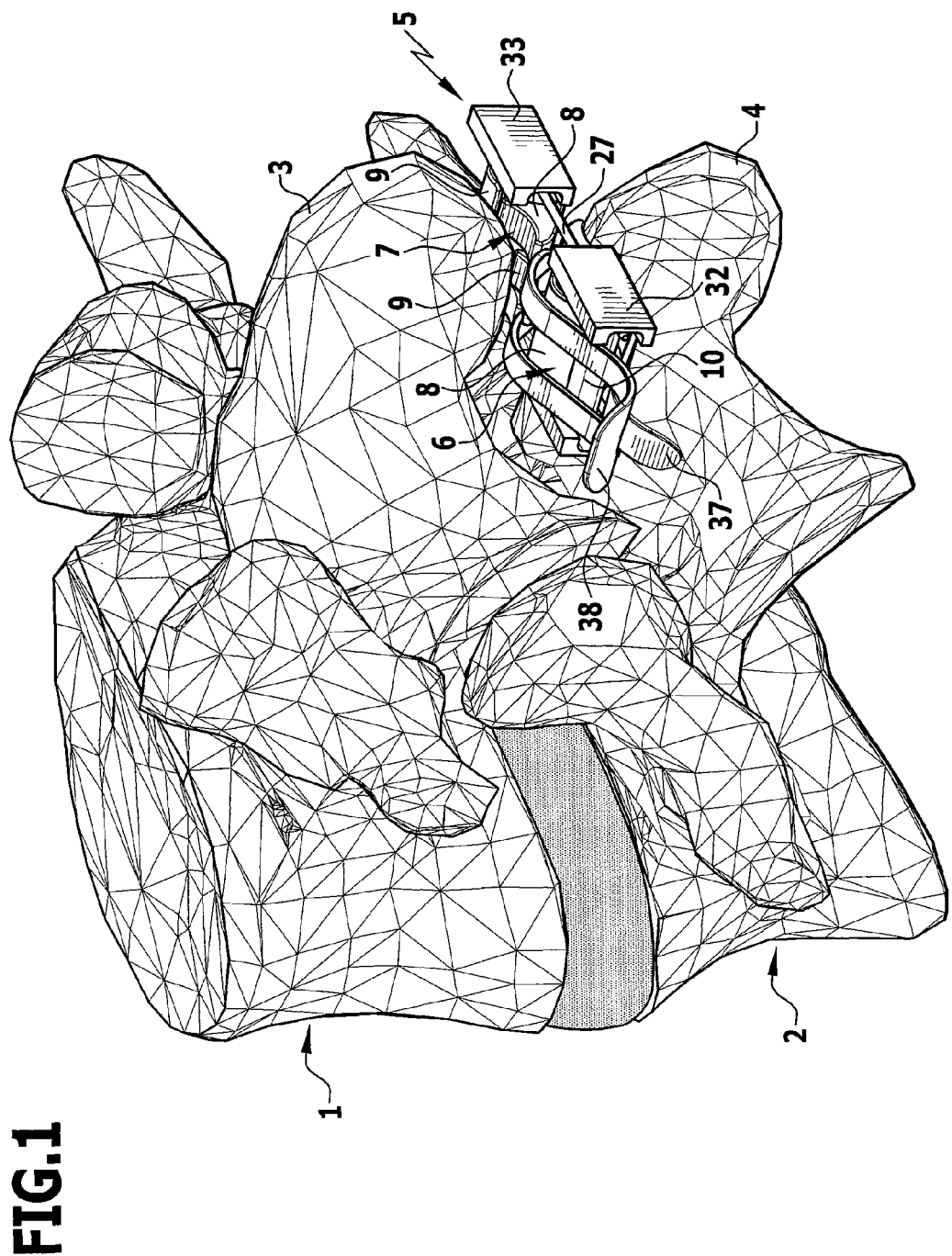
FIG. 1 is a perspective view of two adjacent vertebral bodies with an implant inserted between the spinous processes of the vertebral bodies before the two implant components are pushed together and before the lateral abutment elements are raised.
Figure 2:
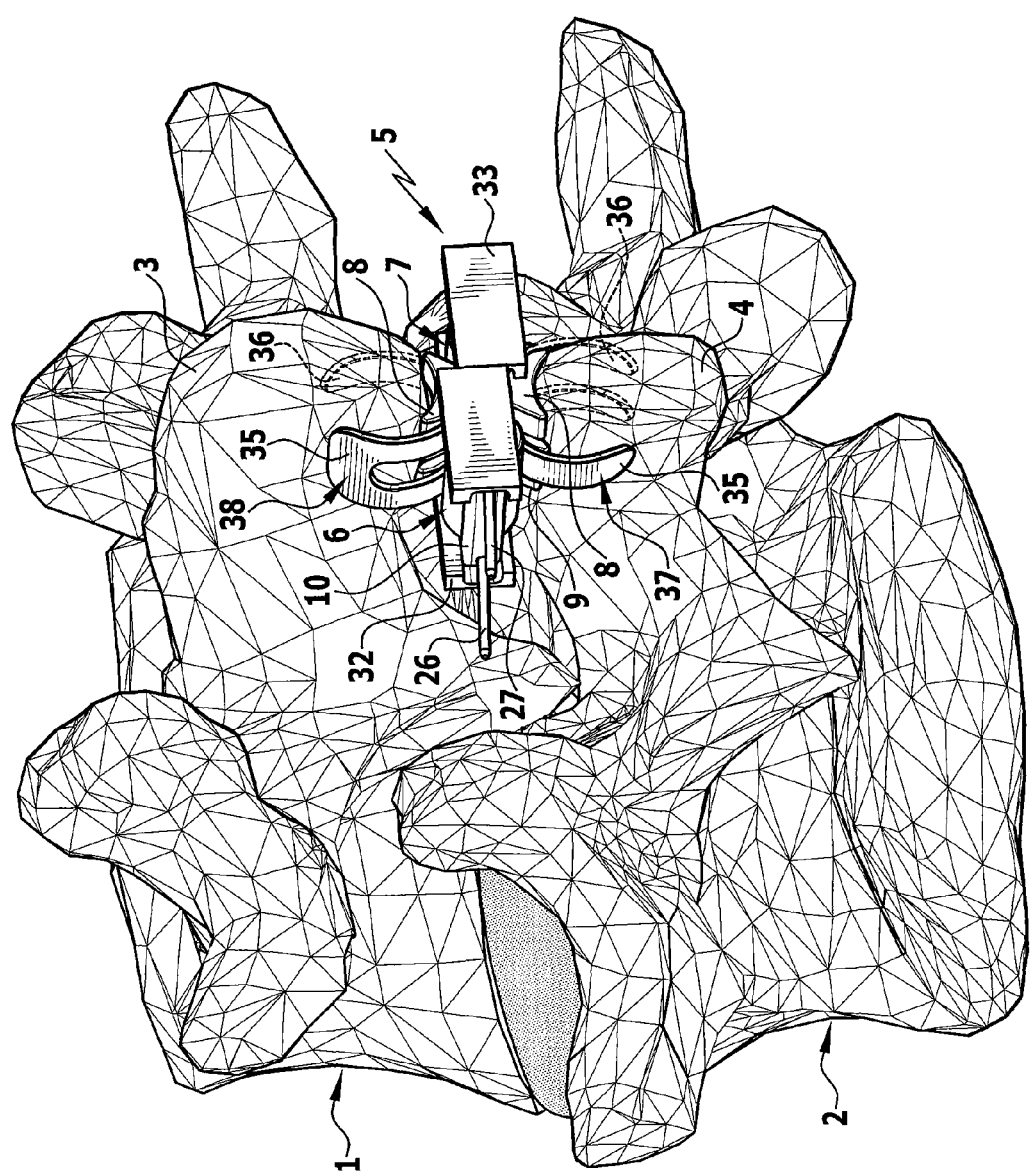
FIG. 2 is a view similar to FIG. 1 after the two implant components are pushed together and after the lateral abutment elements are raised.
Figure 3:
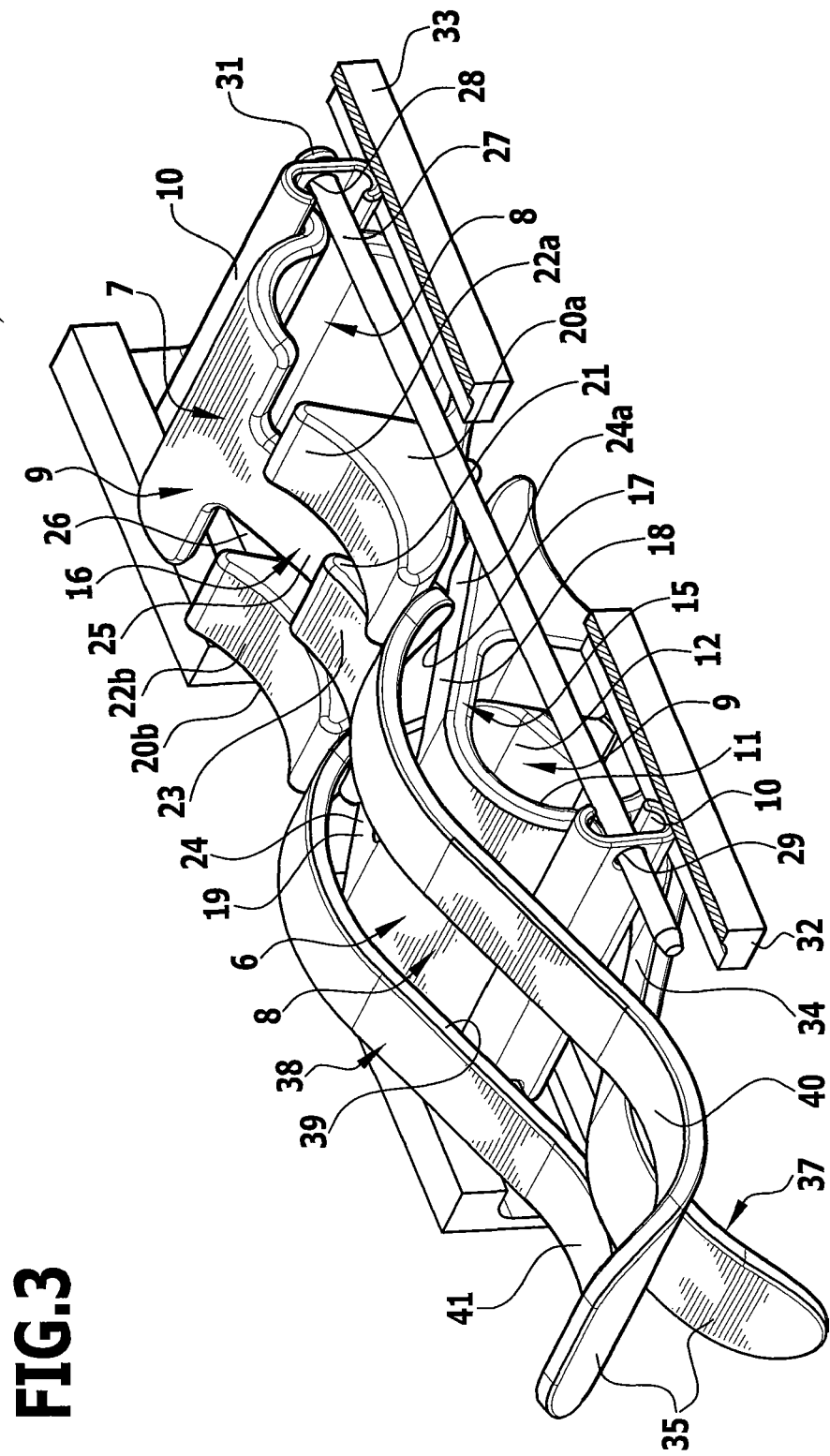
FIG. 3 is a perspective view of the implant of FIGS. 1 and 2 before the implant components are pushed together and before insertion of the lateral abutment elements.
Figure 4:
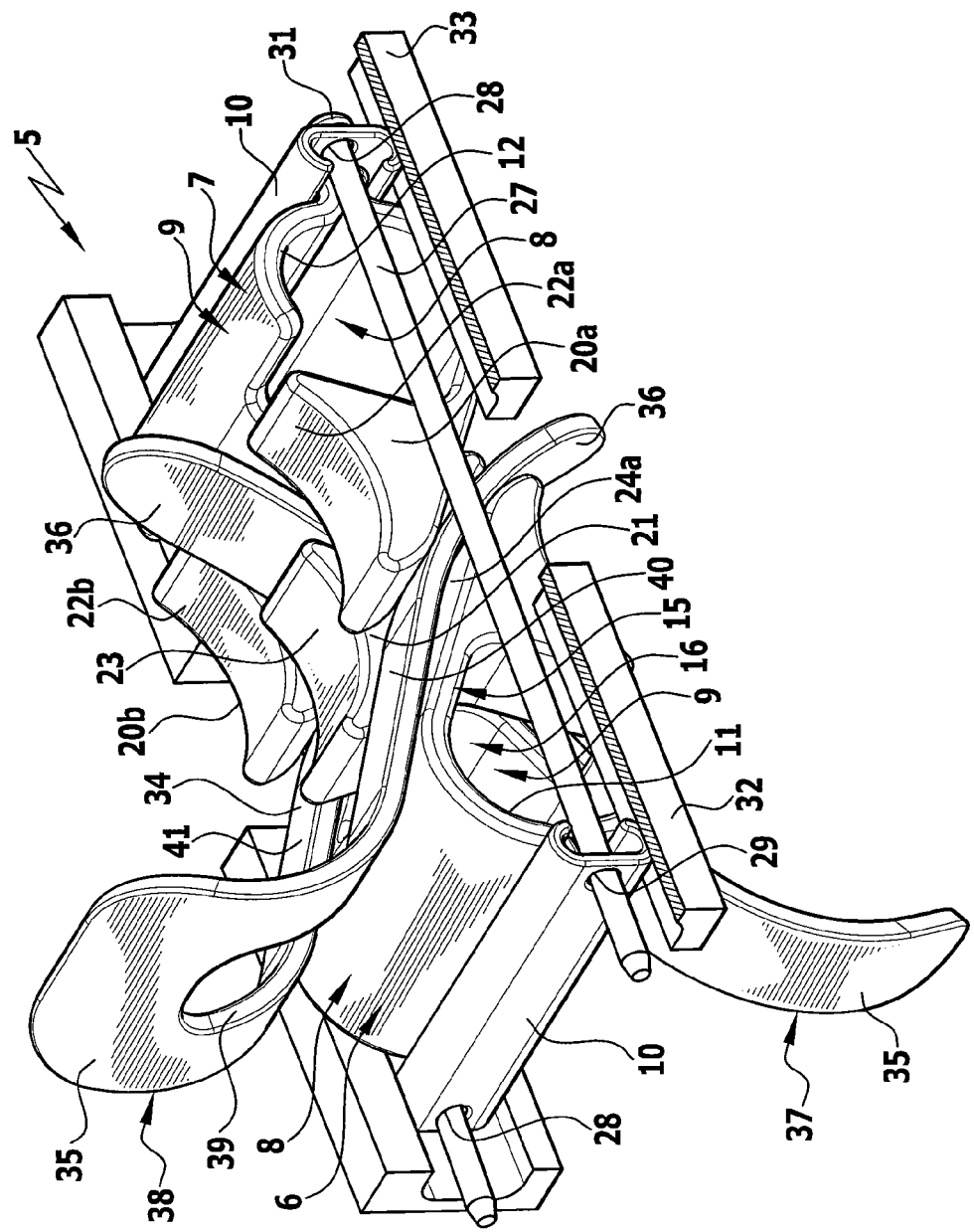
FIG. 4 is a view similar to FIG. 3 with the implant components partially pushed together and with the abutment elements inserted, but not yet fully raised.
Figure 5:
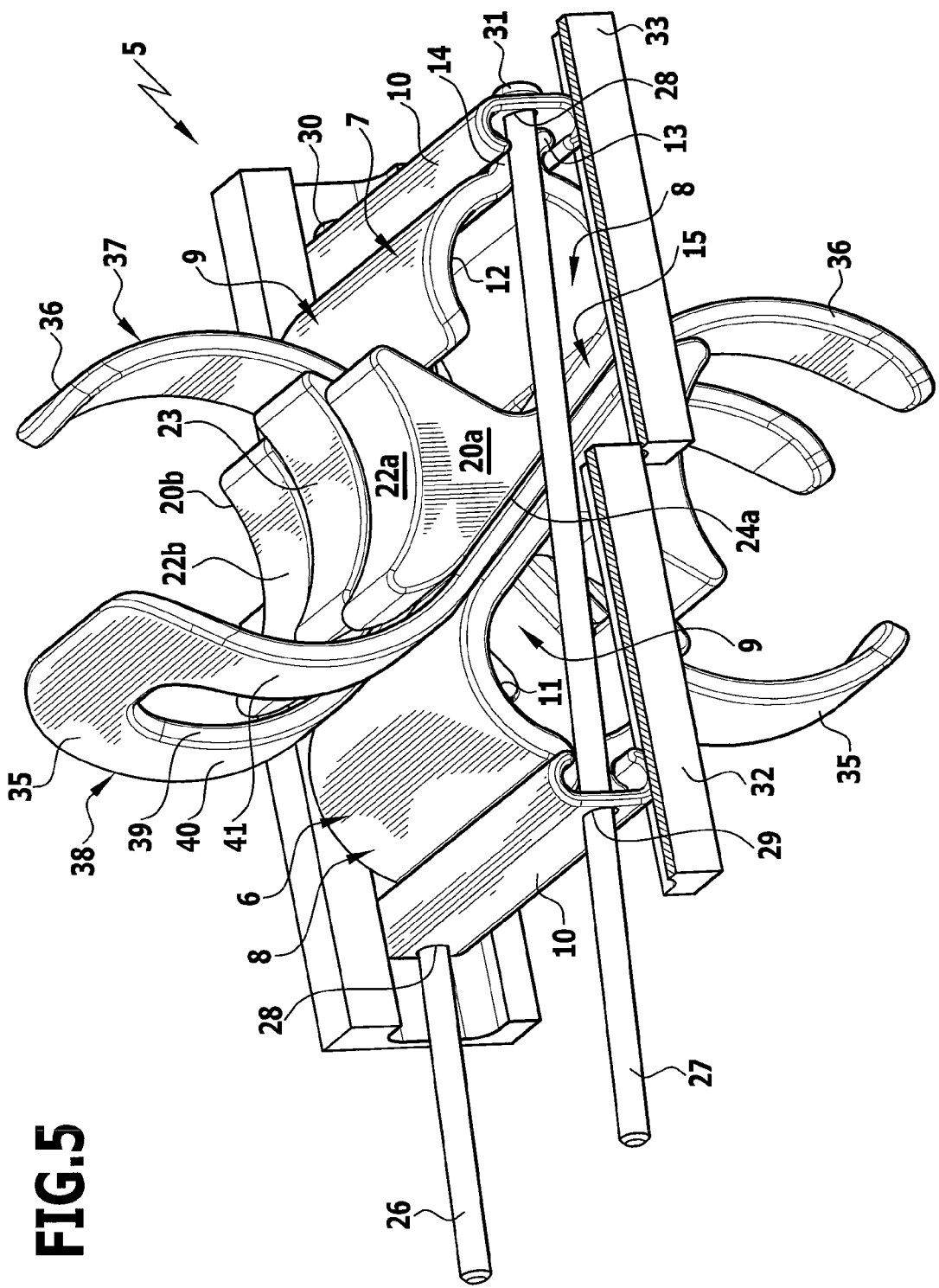
FIG. 5 is a view similar to FIG. 4 with the implant components fully pushed together and abutment elements raised.
Figure 6:
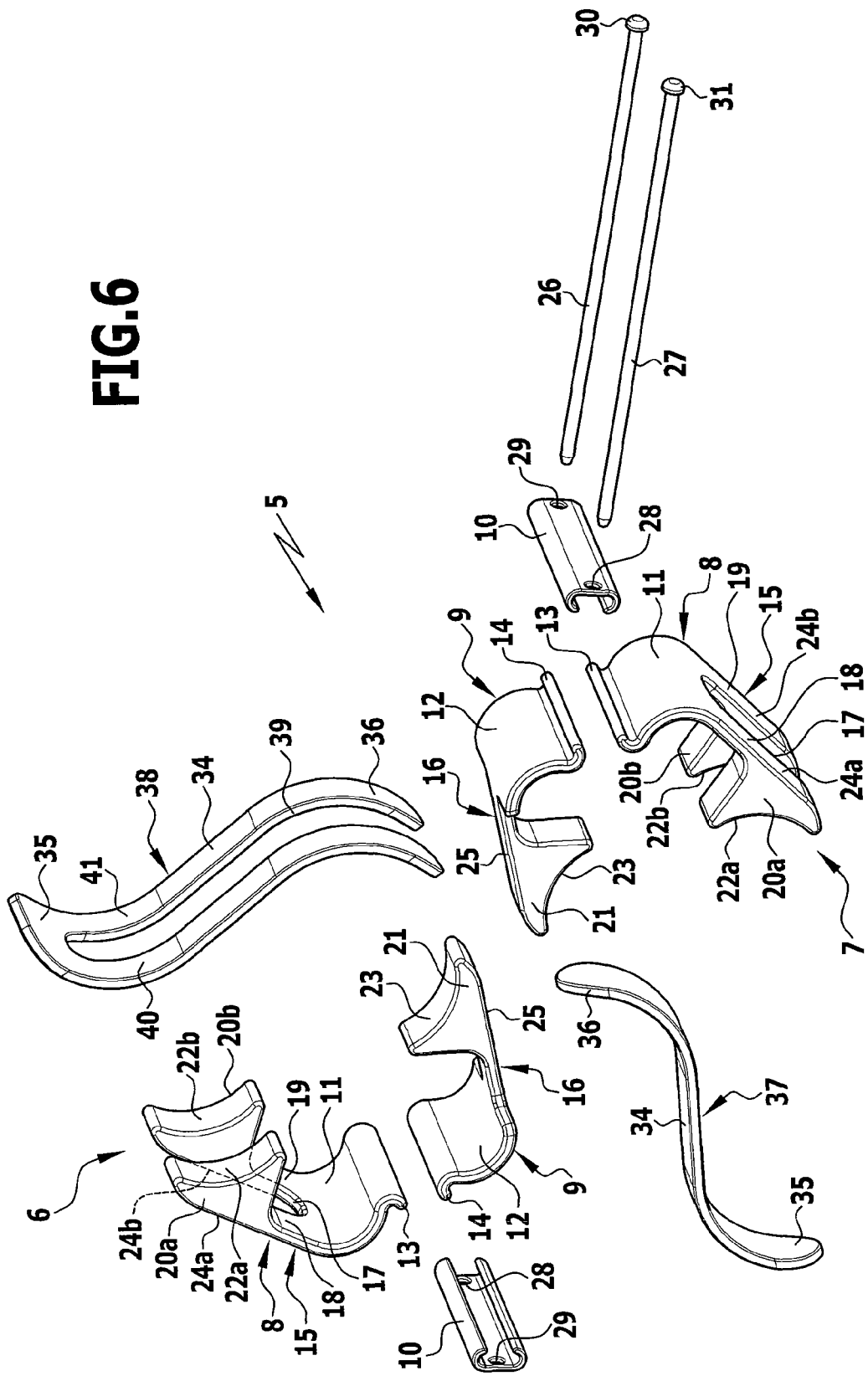
FIG. 6 is an exploded representation of the implant of FIG. 3.

FIGS. 1 and 2 are perspective views of two adjacent vertebral bodies 1, 2, between the spinous processes 3, 4 of which an implant 5 is inserted. This is supported against both adjacent spinous processes 3, 4 and acts as spacer element there between the two spinous processes 3, 4, so that the spacing of the two spinous processes 3, 4 can be adjusted by changing the height of the implant 5 and can then be maintained by the implant 5.

Different structures of the implant 5 can be selected and different embodiments of such an implant 5 are described below on the basis of FIGS. 3 to 53. What all implants have in common is the capability that the implant can be inserted into the interstice between two spinous processes 3, 4 with low structural height and after insertion can then increase its structural height, so that the desired spacing of the spinous processes 3, 4 can be adjusted and maintained.

In a first preferred exemplary embodiment, which is shown in FIGS. 1 to 6, the implant 5 comprises two implant components 6, 7, which are configured identically in this case and only one of which is described in more detail below. This implant component consists of two separate structural parts 8, 9, which are held together by means of a C-shaped clamp 10. On the ends of the structural parts 8, 9 facing one another, both structural parts 8, 9 have a band-like, bent section 11 or 12, which terminates at the end of the structural parts 8, 9 in a flange 13, 14 bent sharply in the opposite direction. This flange can be additionally thickened in a bead shape. The C-shaped clamp 10 engages around and behind the two flanges 13, 14, so that a connection of the two structural parts 8, 9 occurs in this region that also allows the structural parts 8, 9 to pivot relative to one another, and thus constitutes a hinge-like connection.

The two sections 11, 12 merge into support arms 15, 16 at their end opposite the flanges 13 and 14 respectively, wherein on one section 11 the support arm 15 extends over the entire width of the section 11 and is divided into two adjacent support arm sections 18, 19 by a longitudinal slot 17 extending from the free end of the structural part 8 to the beginning of section 11. In the case of the other structural part 9, the support arm 16 is narrower than section 12 and is arranged in the centre thereof. In this case, the width of the support arm 16 is equal to or smaller than the width of the longitudinal slot 17 on the other structural part, so that the support arm 16 can penetrate into the longitudinal slot 17 between the two support arm sections 18, 19.

On their facing inner surfaces in the region of their free ends, both the support arm 16 and the two support arm sections 18, 19 bear a projection 20a, 20b and 21, one side of which is configured as concavely curved support surface 22a, 22b and 23 respectively.

When the two structural parts 8, 9 are held together by the clamp 10, the support arms 15 and 16 cross over one another. In this case, the support arm 16 penetrates into the longitudinal slot 17 between the two support arm sections 18, 19 of the other structural part. The support surfaces 22a, 22b and 23 thus each face outwards on the opposite side of the structural part. The two identically configured implant components 6, 7 are pushed towards one another with the free ends of their support arms 15, 16 directed towards one another so that the respective outer faces of the support arms of one implant component abut against the outer faces of the support arms of the respective other implant component, and slide on one another as the two implant components 6, 7 approach one another. In the exemplary embodiment shown in FIGS. 1 to 6, these outer faces are substantially plane and therefore run inclined as a result of the crossover of the support arms 15, 16, the outer faces of the support arms 15, 16 of an implant component in this case being arranged approximately in a V shape towards the free end. At the free ends the outer faces 24a, 24b are bent down slightly in order to facilitate the sliding as the implant components 6, 7 initially approach one another.

When the two implant components 6, 7 are pushed together and the support arms 15, 16 are slid onto one another, the support arms 15, 16 cross over to a greater extent, so that the free ends of the support arms 15, 16, and thus the outwardly facing support surfaces 22a and 22b on one side and 23 on the other, are moved away from one another, i.e. the spacing of the outwardly directed support surfaces facing opposite sides of the implant component is increased. In this case, the support surfaces 22a and 22b of one implant component and the support surface 23 of the other implant component then lie directly adjacent to one another, the support surface 23 of the other implant component thus being located between the support surfaces 22a and 22b of one implant component, so that the three support surfaces jointly form a trough-shaped locating face for a spinous process, which is supported on these adjacent support surfaces.

The further the two implant components 6, 7 are pushed towards one another, the larger the spacing of the support surfaces on opposite sides of the implant component can be adjusted, and therefore the larger the structural height of the implant and the spacing of the spinous processes supported on the implant.

To push the implant components 6, 7 towards one another in the described manner, tie bars 26, 27 are arranged on both sides next to the implant components in the form of thin bars that pass through the openings 28, 29, which are located at the ends of the two clamps 10. These clamps thus hold the two structural parts of an implant component together, while also acting as end pieces, and when these approach one another the two implant components 6, 7 are pushed towards one another.

Both tie bars 26, 27 have a thickened head 30 and 31 respectively at one end that restricts the penetration depth into the openings of one clamp, and on the opposite end the opposite clamp of the implant is freely displaceable and can be displaced there by means of an instrument (not shown in the drawing) towards the other clamp, so that the two implant components are thus pushed towards one another. When the desired penetration depth is reached, the displaceable clamp can be fastened in place by suitable means, and these means are not shown in the drawing. For example, this can be a clamping operation, a deformation operation or the like, or the spacing is fixed by attaching a stop to the tie bar.

In the exemplary embodiment shown in FIGS. 1 to 6, the tie bars 26, 27 are covered on the outside by a respective C-shaped cover strip 32, 33, so that the tie bars are protected, while an undesirable contact with surrounding tissue can also be avoided.

In the exemplary embodiment of FIGS. 1 to 6, band-like abutment elements are additionally inserted into the implant, i.e. a band-like abutment element 37, which is rectilinear in the central section 34 and bent to opposite sides in the end sections 35, 36 adjoining on both sides, said abutment element being substantially identical in configuration to a second abutment element 38, which is, however, wider than the abutment element 37 and has a longitudinal slot 39 running from one end almost to the other end, so that this wider abutment element 38 is divided into two adjacent webs 40, 41. The width of the longitudinal slot 39 is equal to or larger than the width of the narrower abutment element 37, so that this can penetrate into the longitudinal slot 39.

The narrower abutment element 37 is inserted between the outer faces of the central support arms 16 of the two implant components, the two webs 40 and 41 between the outer faces of the support arm sections 18, 19 of the two implant components, so that the end sections 35, 36 of the two abutment elements 37, 38 bent in opposite directions directly next to the support surfaces 22a, 22b and 23 project substantially transversely to the displacement plane of the two implant components and thus abut laterally against the spinous processes 3, 4, which rest on the support surfaces 22a, 22b and 23 when the implant is inserted. As a result, the implant is also reliably secured against sliding transversely relative to the spinous processes, in which case the two abutment elements 37, 38 are held between the two implant components in a wedge fit and are thus secured against any further displacement.

During the implantation of the implant the abutment elements are not yet inserted, so that the implant can be inserted easily through a relatively small access opening because of its small structural height. The abutment elements 37, 38 are only inserted between the outer faces of the support arms when the implant is inserted. However, this insertion occurs before the implant components are pushed together and thus before the spacing of the support surfaces is increased, so that the abutment element can be freely displaced between the outer faces of the support arms, as is shown by way of FIGS. 3, 4 and 5.

The described implant can be made from metal or a sterilisable biocompatible plastic material. A very simple structure results, since both implant components are identical in structure. The implant can be inserted in preassembled state, i.e. with implant components held together by the two tie bars 26, 27, but still not pushed together to such an extent that the support surfaces are substantially moved away from one another.

In the case of the implant of FIGS. 7 to 9, a very similar structure is selected, and therefore corresponding parts have the same reference numerals—as is also the case in the exemplary embodiments described below. In contrast to the exemplary embodiment of FIGS. 1 to 6, the implant components in the exemplary embodiment of FIGS. 7 to 9 and in all the other exemplary embodiments described below is not configured from two structural parts, but in one piece. Therefore, the support arms 15 and 16 of each implant component are connected to one another by means of a band-like, single-part bridge section 42, and therefore a clamp is no longer necessary to hold together individual parts of an implant component. Therefore, all that is necessary to push the two implant components together is to provide end pieces 43, 44 on the outer surface of the bridge sections 42, these simply consisting of webs running transversely to the longitudinal direction of the band-shaped bridge sections 42, one of which webs being connected in one piece to the two tie bars 26, 27, whereas the other has openings 28, 29, through which the tie bars 26, 27 pass. To fasten the end piece 44 supporting the tie bars 26, 27 on the implant, projections 45 running parallel to this end piece 44 can be moulded on the tie bars 26, 27, which abut against the inner surface of the bridge sections 42, so that the tie bars 26 and 27 and these projections 45 engage around the side edges of the bridge sections 42.

In the embodiment described below the two implant components can be displaced towards one another in the same manner. For increased clarity in the following exemplary embodiments the end pieces 43, 44 and the tie bars 26, 27 have been partially omitted and will not be described separately.

Figure 7:
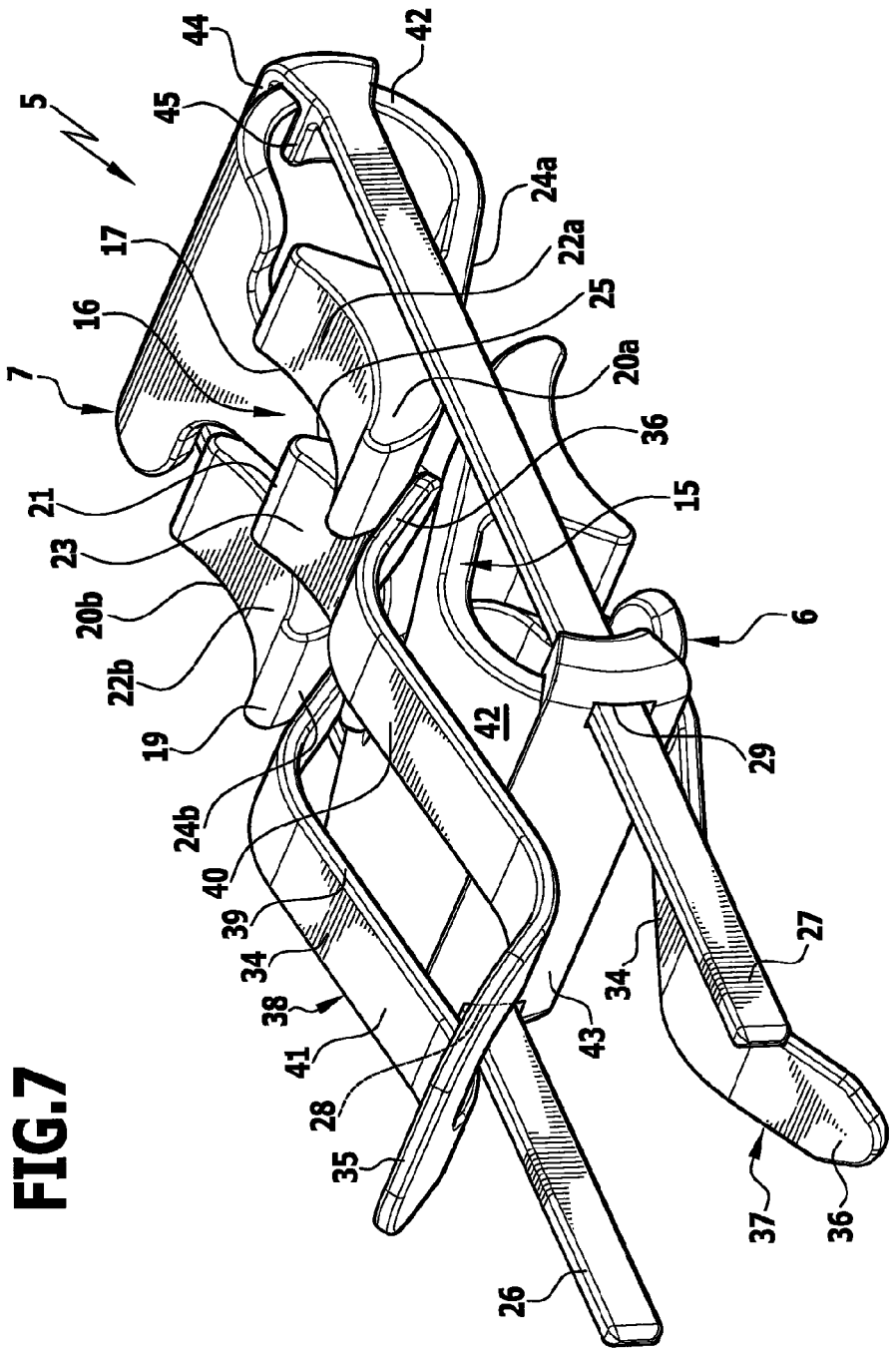
FIG. 7 is a view similar to FIG. 3 with a further preferred embodiment of an implant.
Figure 8:
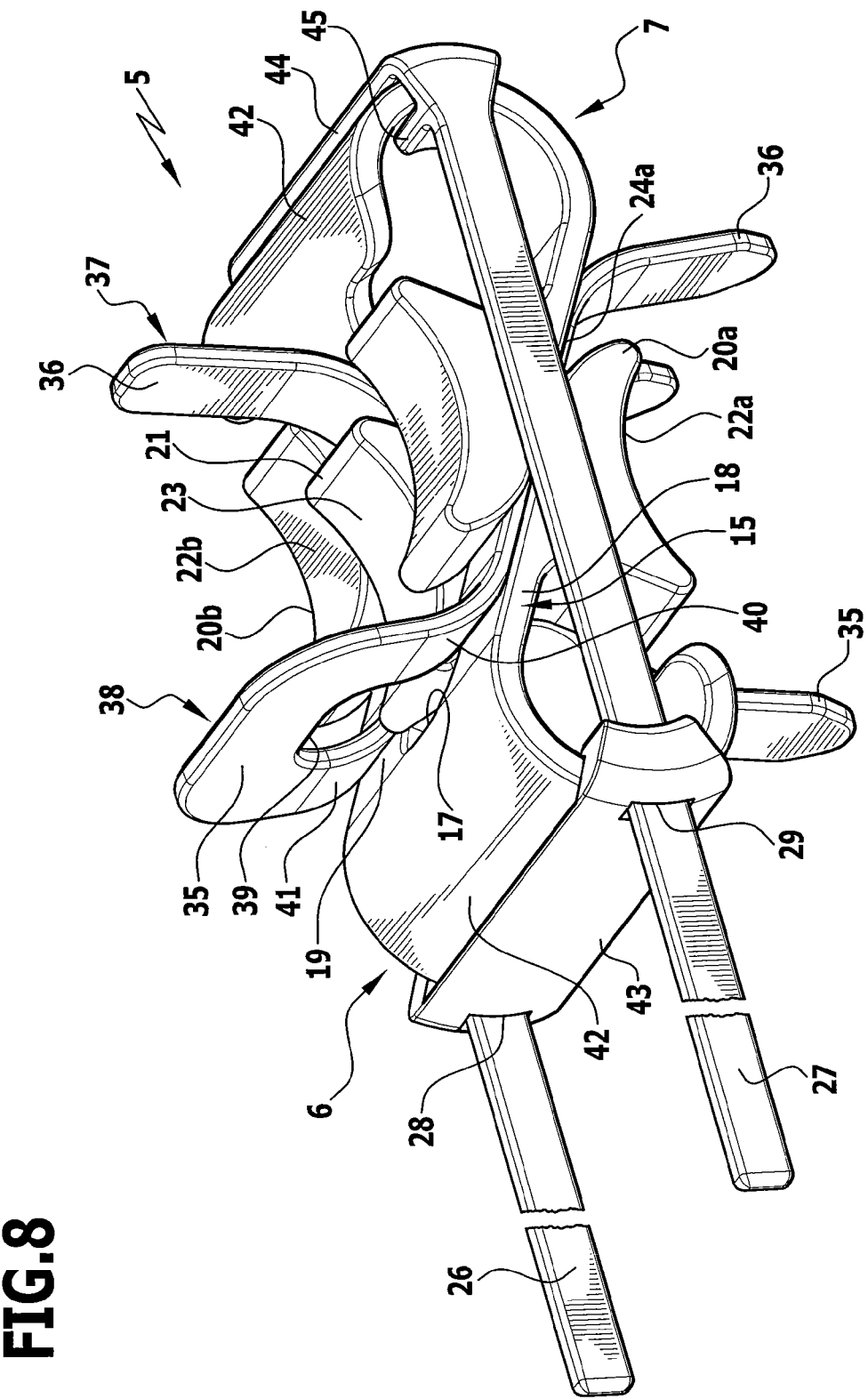
FIG. 8 is a view similar to FIG. 7 with the implant components pushed together and abutment elements raised.
Figure 9:
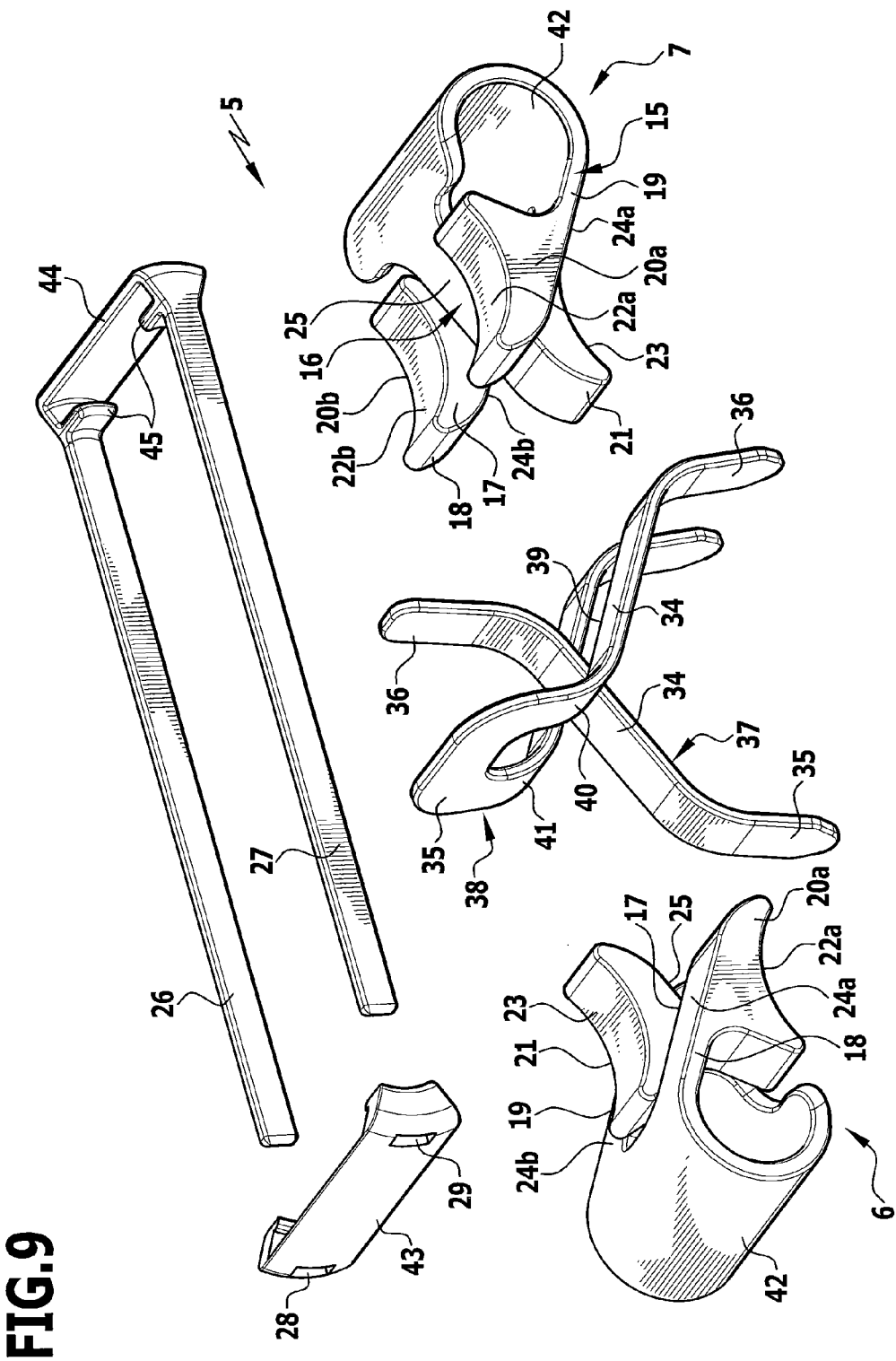
FIG. 9 is an exploded representation of the implant of FIGS. 7 and 8.
Figure 10:
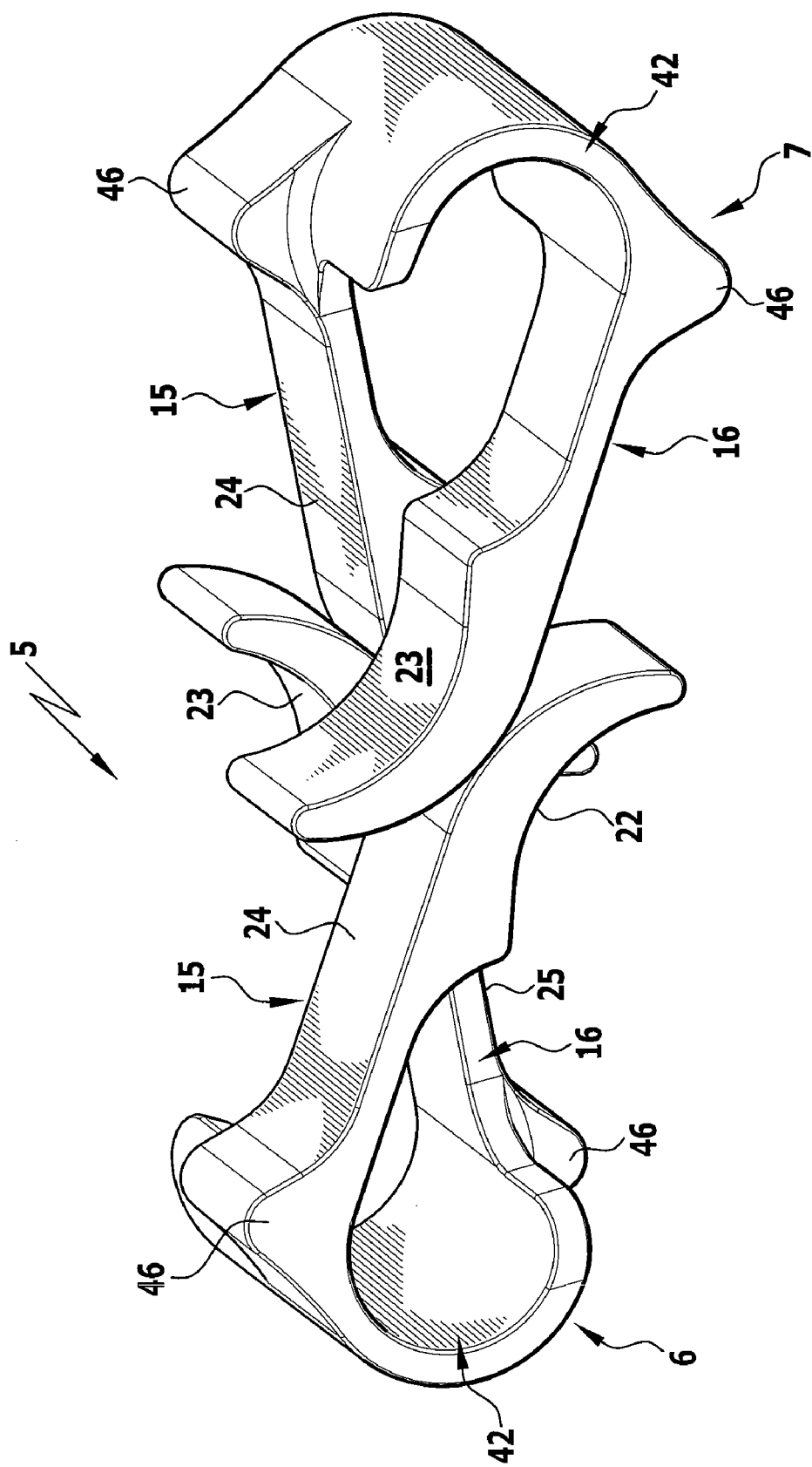
FIG. 10 is a perspective view of an implant with two implant components as the two implant components begin to approach one another.
Figure 11:
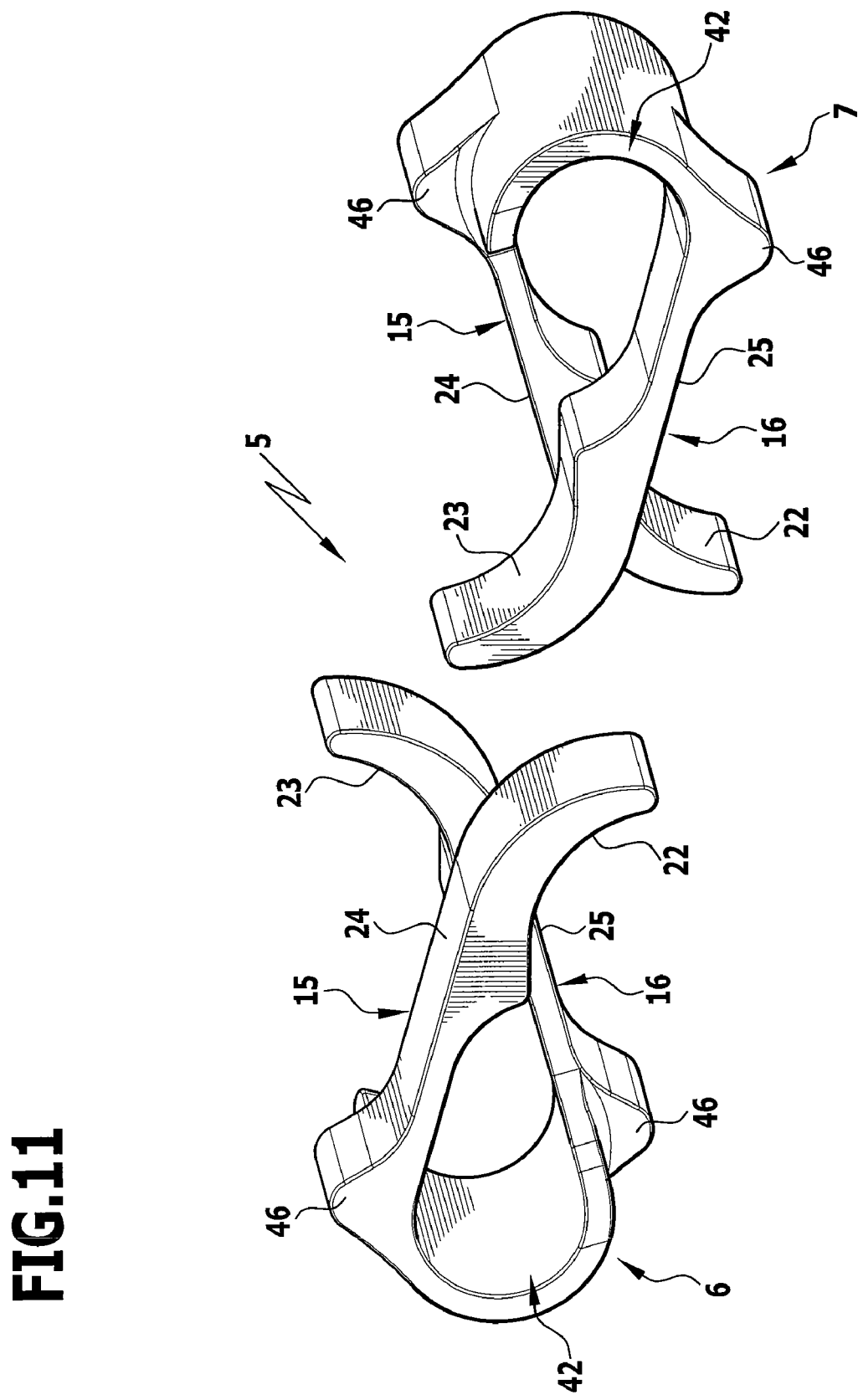
FIG. 11 is a view of the two implant components of the implant of FIG. 10 before they are pushed together.

The implant components of the implant of FIGS. 10 and 11 are similar in structure to those in the exemplary embodiment of FIGS. 7 to 9, but these implant components only have two single-part support arms 15, 16, which are arranged laterally offset on the bridge section 42 so that they lie adjacent to one another, i.e. no support arm slotted in the longitudinal direction is provided in this case, as in the exemplary embodiment of FIGS. 7 to 9. Moreover, in this exemplary embodiment, the slightly thickened ends of the support arms themselves form the support surfaces 22, 23, these support arms 15, 16 being bent to a greater extent in the region of the free ends than is the case in the exemplary embodiment of FIGS. 7 to 9, so that sliding into place is simplified in any case as they are pushed together.

The outer faces of the support arms 15, 16 are also plane in the central region, but a respective raised section 46 adjoins this plane region and causes the bent end of the support arms to be bent to a much greater extent when this raised section 46 is reached than along the sloping plane outer faces of the support arms 15, 16. This restricts the pushing together, while achieving a particularly large change in the spacing of the support surfaces as they are pushed further together, i.e. the surgeon feels an increased resistance as they are pushed together and can therefore assess how far the implant components have been pushed together.

Figure 12:
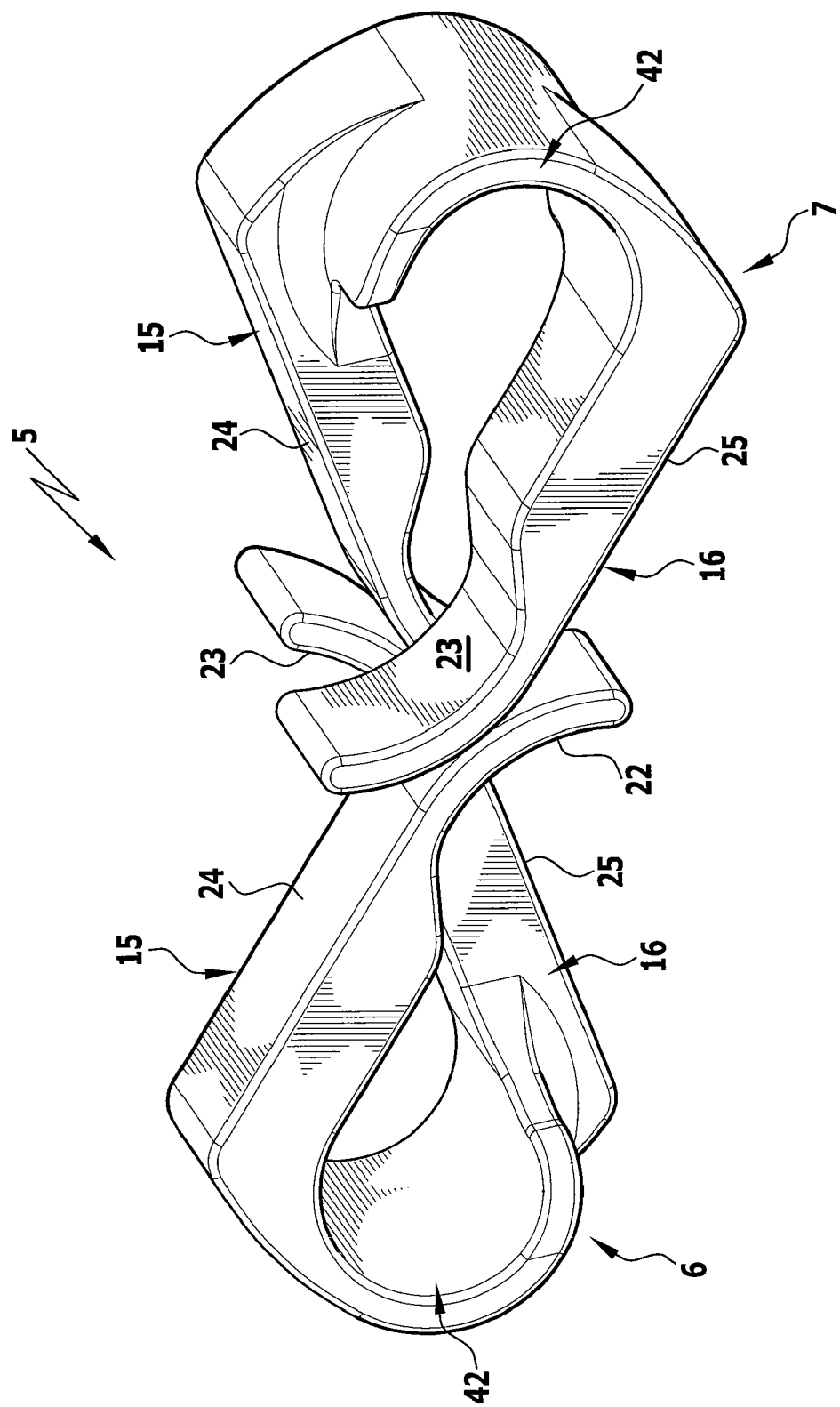
FIG. 12 is a perspective view similar to FIG. 10 in the case of a further preferred exemplary embodiment of an implant.
Figure 13:
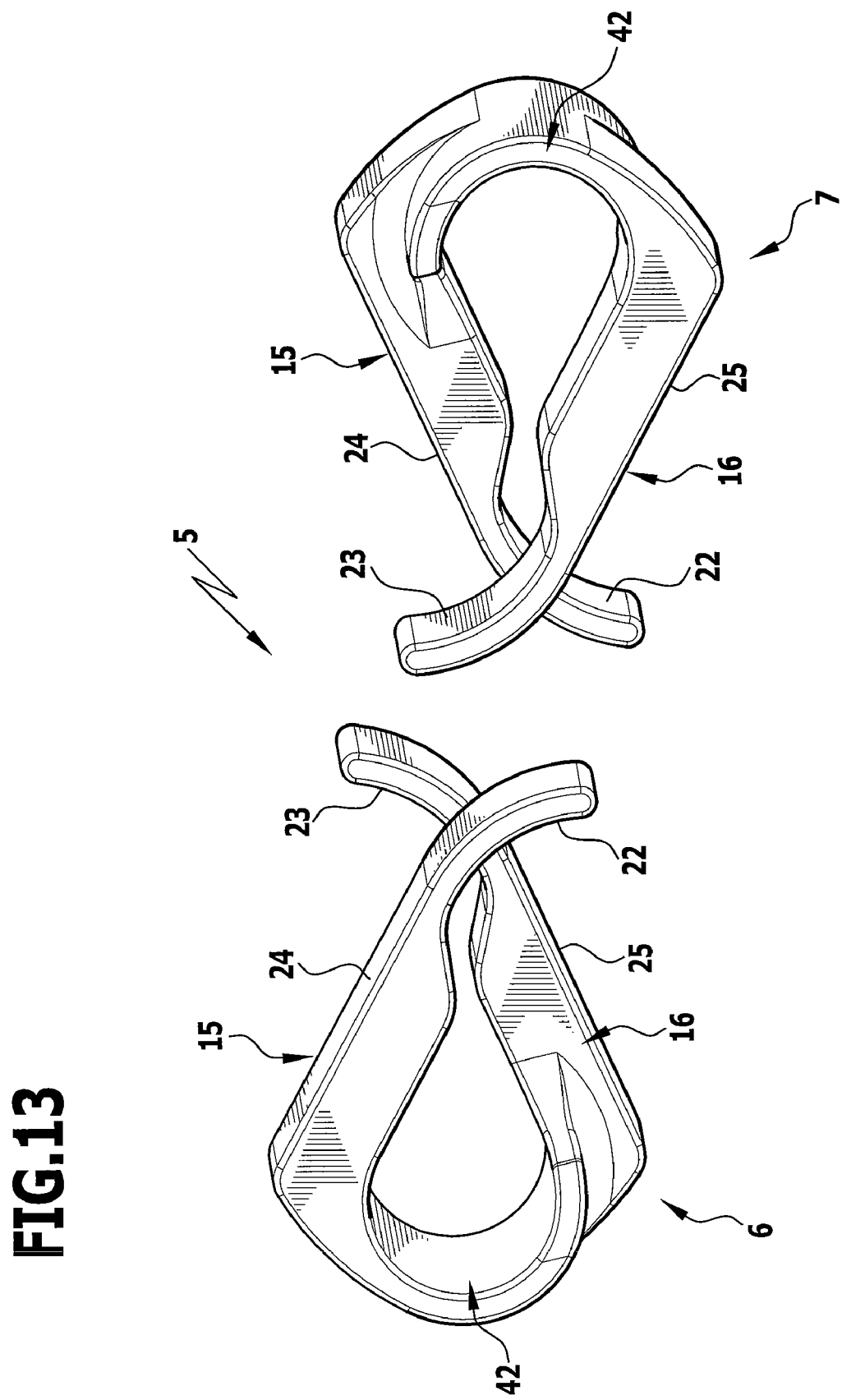
FIG. 13 is a perspective view of the implant components of FIG. 12 before being pushed together.

In the exemplary embodiment of FIGS. 12 and 13, the implant components are very similar in configuration to those of the exemplary embodiment of FIGS. 10 and 11, but the support arms are thickened, wherein the support surfaces 22, 23 are moulded directly into these thickened support arms. Moreover, in this exemplary embodiment the raised sections 46 on the outer faces are absent.

Figure 14:
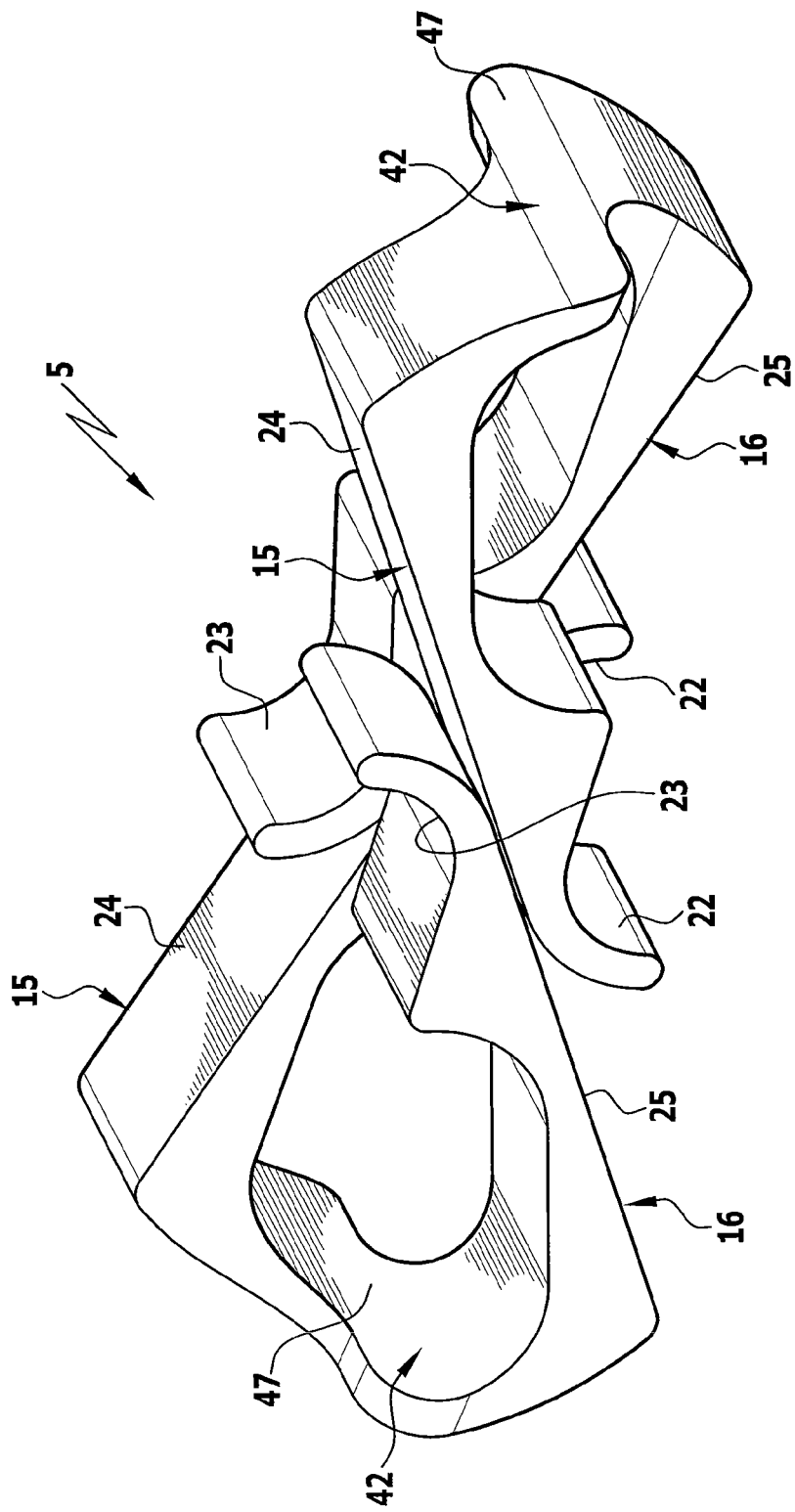
FIG. 14 is a view similar to FIG. 10 in the case of a further preferred exemplary embodiment of an implant.
Figure 15:
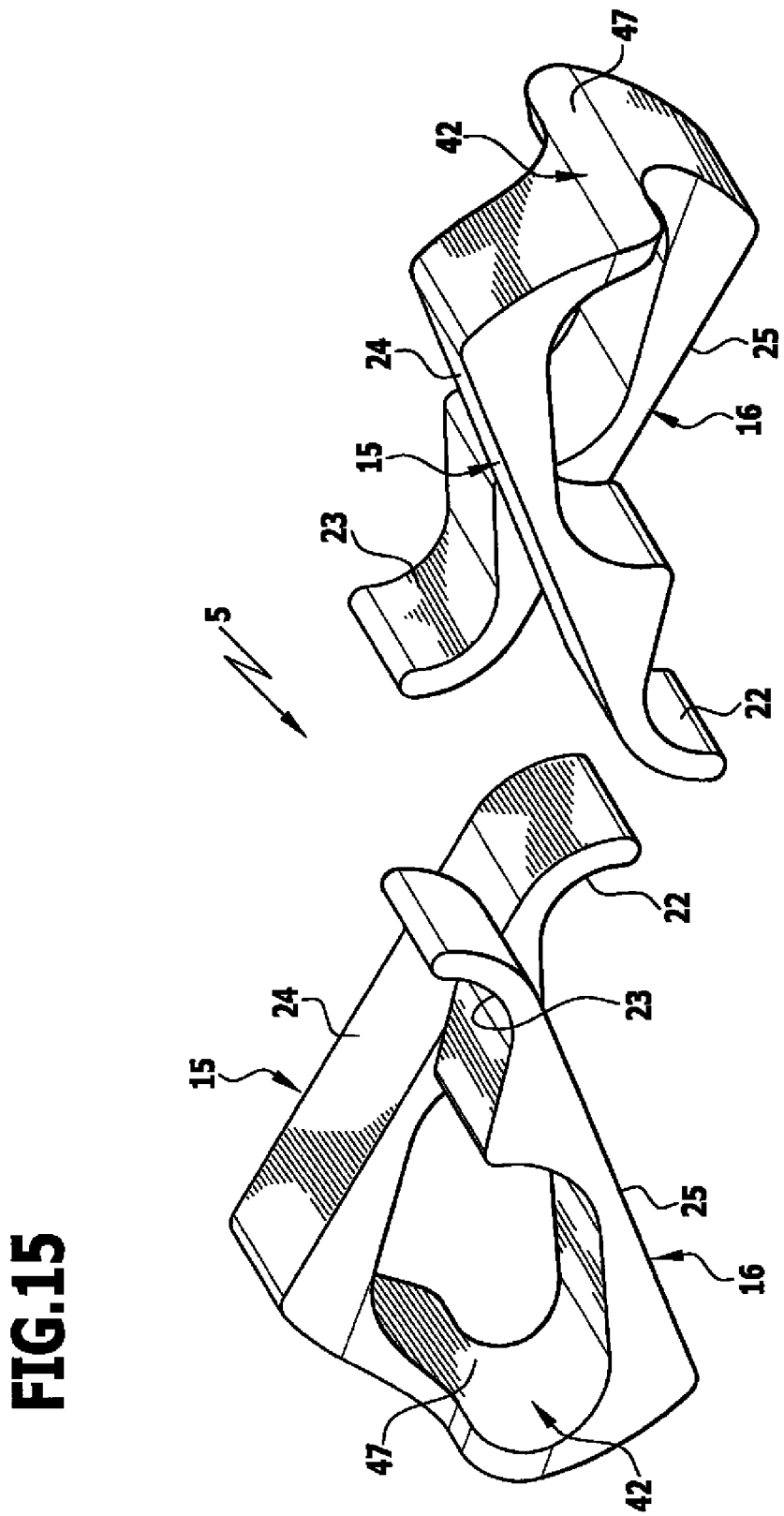
FIG. 15 is a perspective view of the implant components of FIG. 14 before they are pushed together.

In the exemplary embodiment of FIGS. 14 and 15, a similar configuration is selected to that in the exemplary embodiment of FIGS. 10 and 11. The band-like bridge section 42 in this exemplary embodiment is narrow in a similar way to the adjoining support arms, i.e. only a very narrow connection region 47 results, by means of which the adjacent support arms are connected to one another. The raised sections 46 are also absent in this exemplary embodiment.

Figure 16:
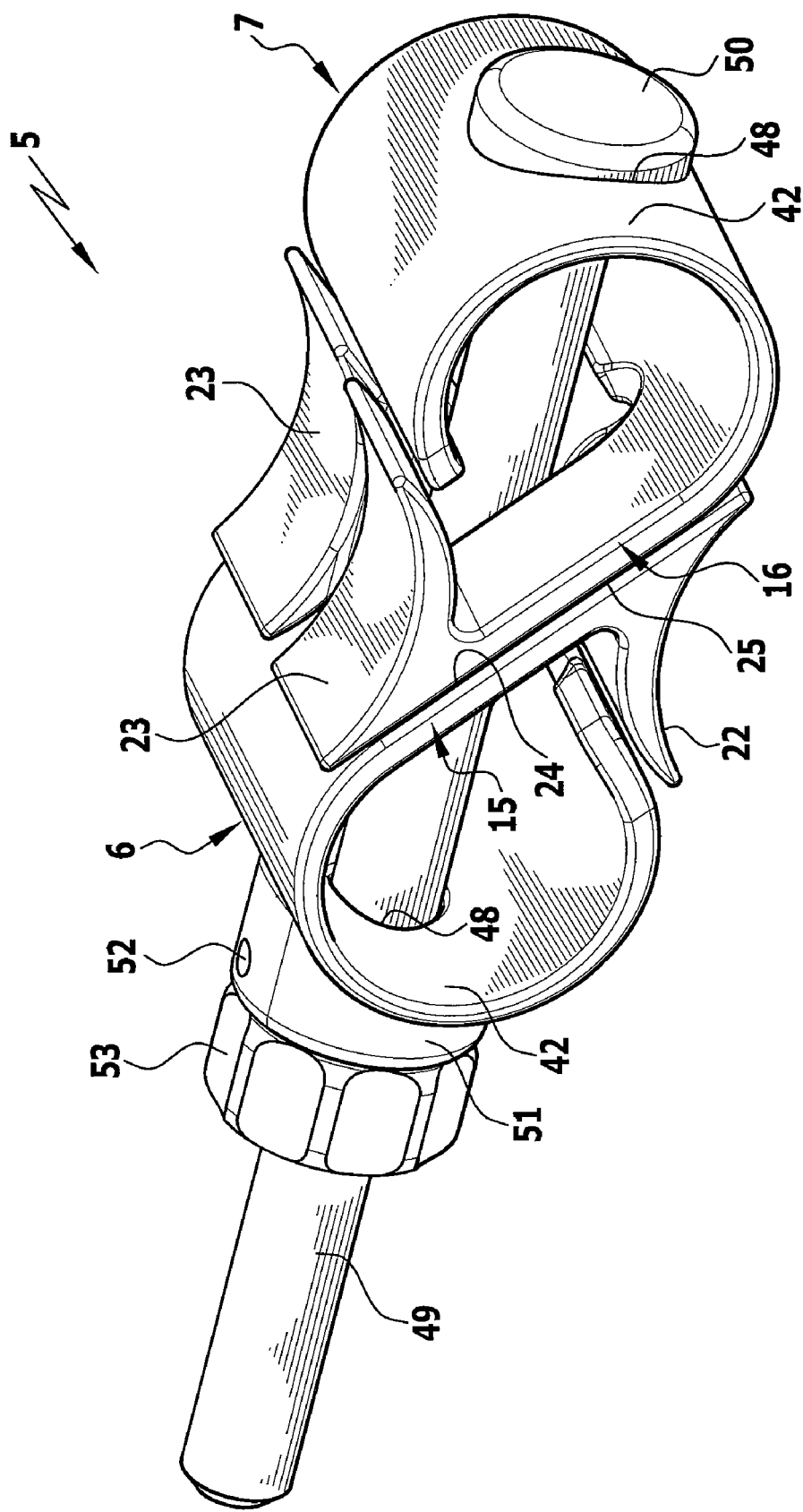
FIG. 16 is a perspective view of a further preferred exemplary embodiment of an implant with a tie bar passing through the implant components.
Figure 17:
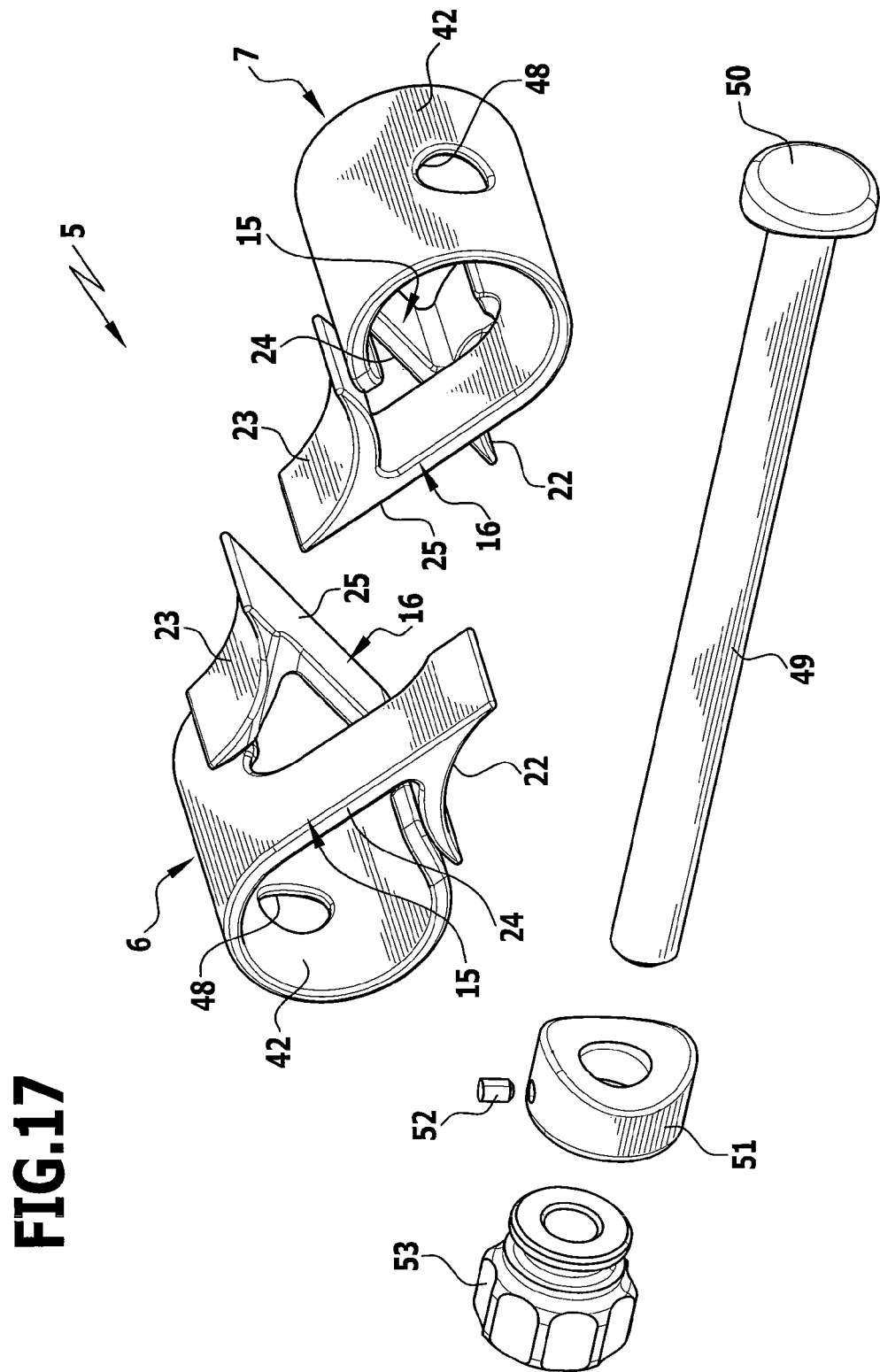
FIG. 17 is an exploded view of the implant of FIG. 16.

In the exemplary embodiment of FIGS. 16 and 17, the two implant components are similar in configuration to those in the exemplary embodiment of FIGS. 10 and 11, wherein the support arms as well as the band-like bridge section 42 are configured as thin webs, which bear outwardly protruding projections 20, 21 at their end with corresponding support surfaces 22 and 23 respectively. In this regard a configuration similar to that in the exemplary embodiment of FIGS. 1 to 6 results, but each implant component has only two adjacent support arms.

A respective through opening 48 is arranged in the web-shaped bridge section 42 in both implant components, and projecting through these openings 48 is a single tie bar 49, which passes between the two support arms 15 and 16 of the implant components and thus passes centrally through the two implant components. The tie bar 49 abuts against an implant component with a thickened head 50, and a holding sleeve 51 is slid onto the opposite end that can be fixed along the tie bar 49 by means of a screw 52 screwed into a threaded hole of the holding sleeve 51. In addition, a grip part 53 is slid onto the tie bar 49, with which the holding sleeve 51 can be pushed against the head 50 so long as the screw 52 has not yet been tightened. As a result, the two implant components can be pushed towards one another, so that the support surfaces 22 and 23 are extended upwards and downwards by the support arms 15, 16 sliding onto one another in the described manner.

Figure 18:
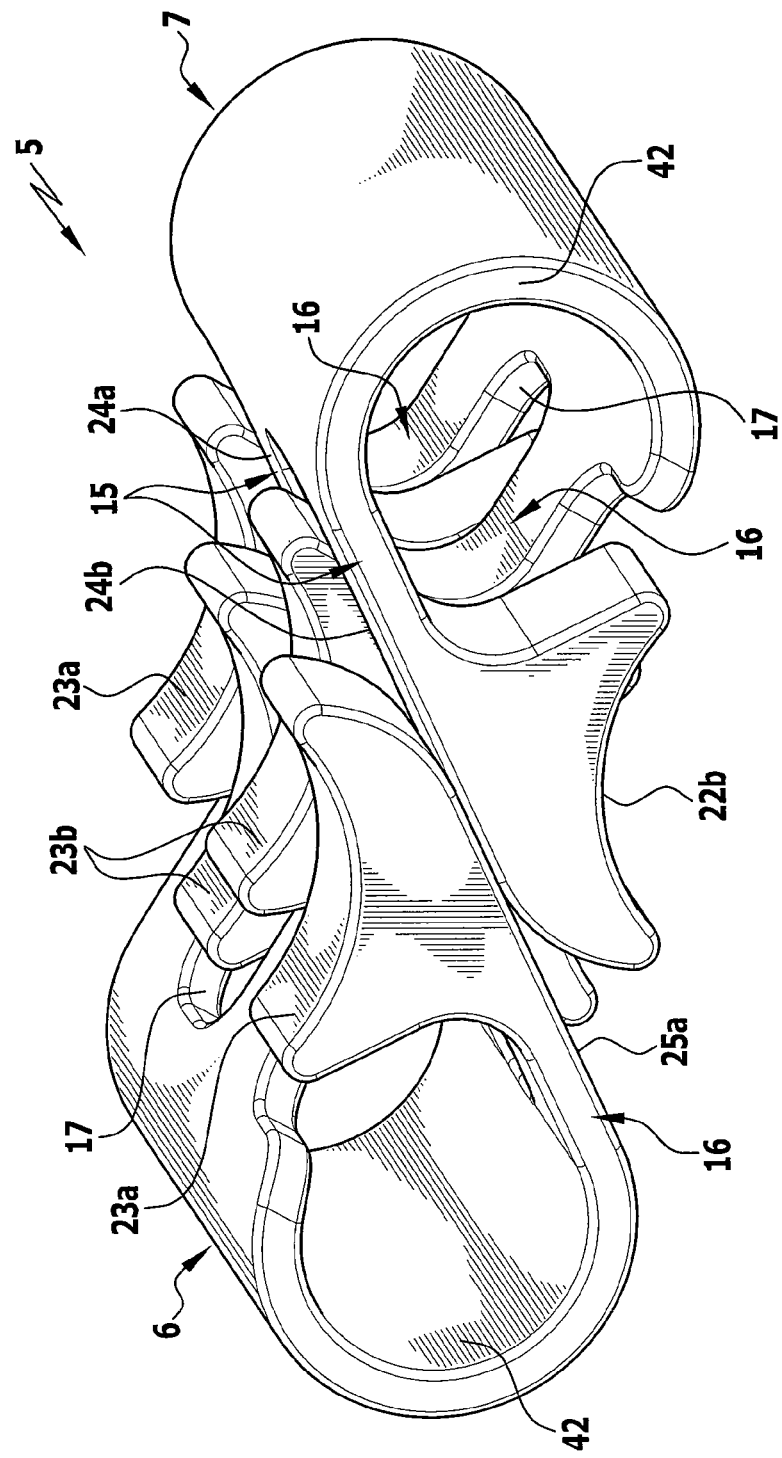
FIG. 18 is a perspective view of a further preferred exemplary embodiment of an implant with the implant components pushed together having support arms respectively configured in pairs.
Figure 19:
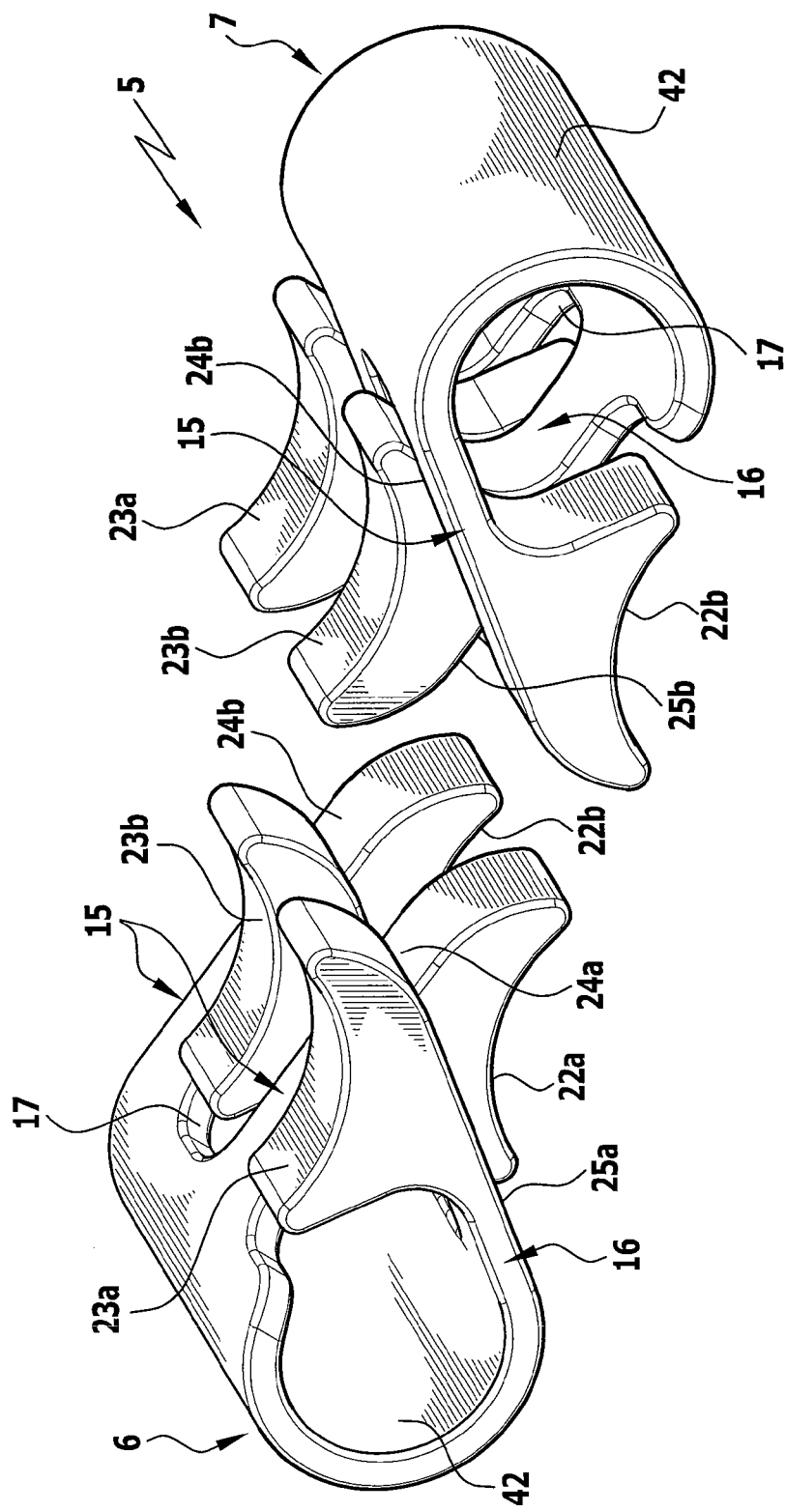
FIG. 19 is a perspective view of the implant components of the implant of FIG. 18 before being pushed together.

In the exemplary embodiment of FIGS. 18 and 19 a similar configuration is selected to that in the exemplary embodiment of FIGS. 7 to 9, but the two support arms 15, 16 of an implant component are respectively divided into adjacent support arm sections 18, 19 by a longitudinal slot 17, i.e. all the support surfaces are also respectively configured in duplicate, wherein the individual support arm sections and support surfaces of the two implant components intermesh in the manner of a comb.

Figure 20:
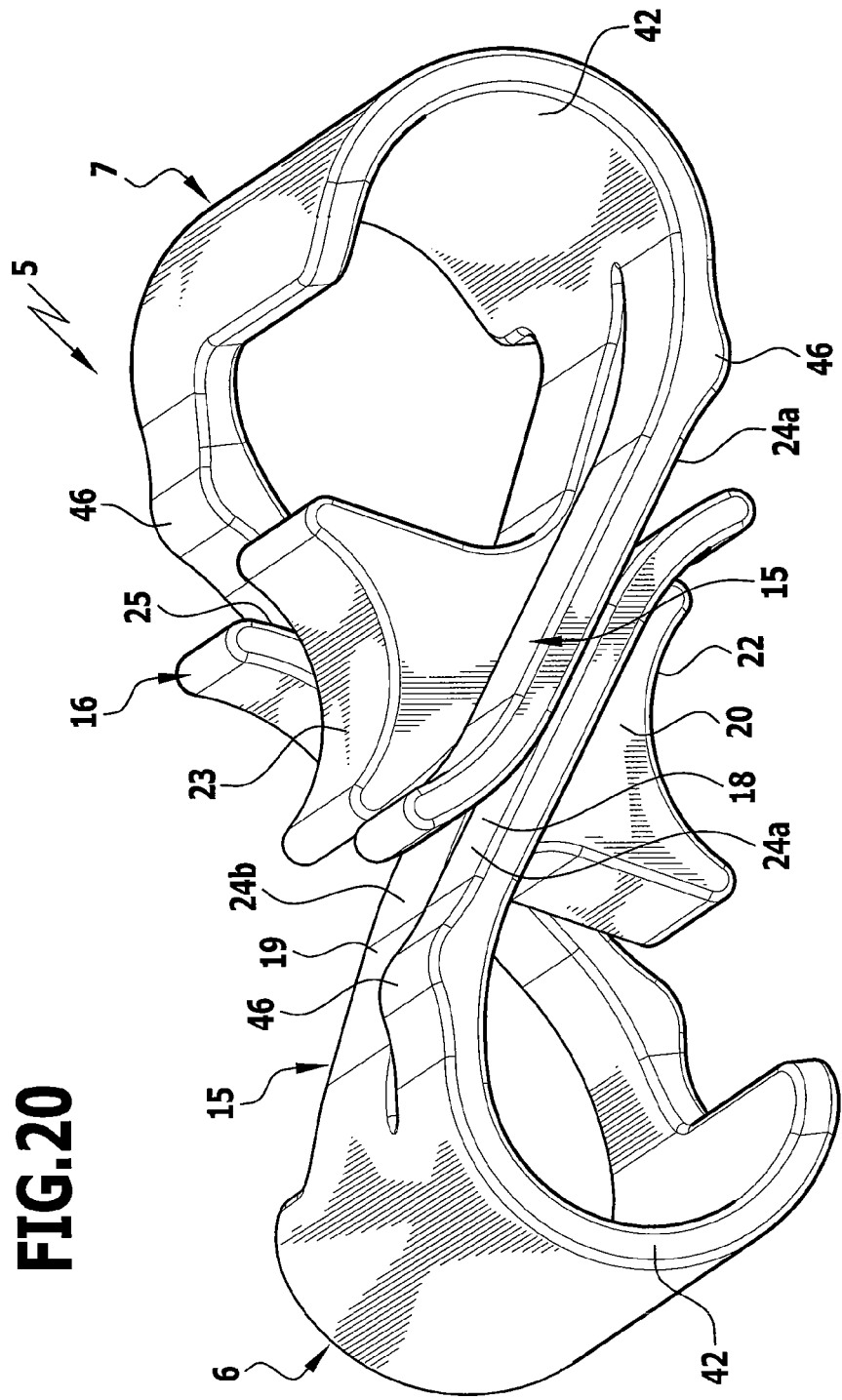
FIG. 20 is a perspective view similar to FIG. 18 in the case of a further preferred exemplary embodiment of an implant with differently configured support arms.
Figure 21:
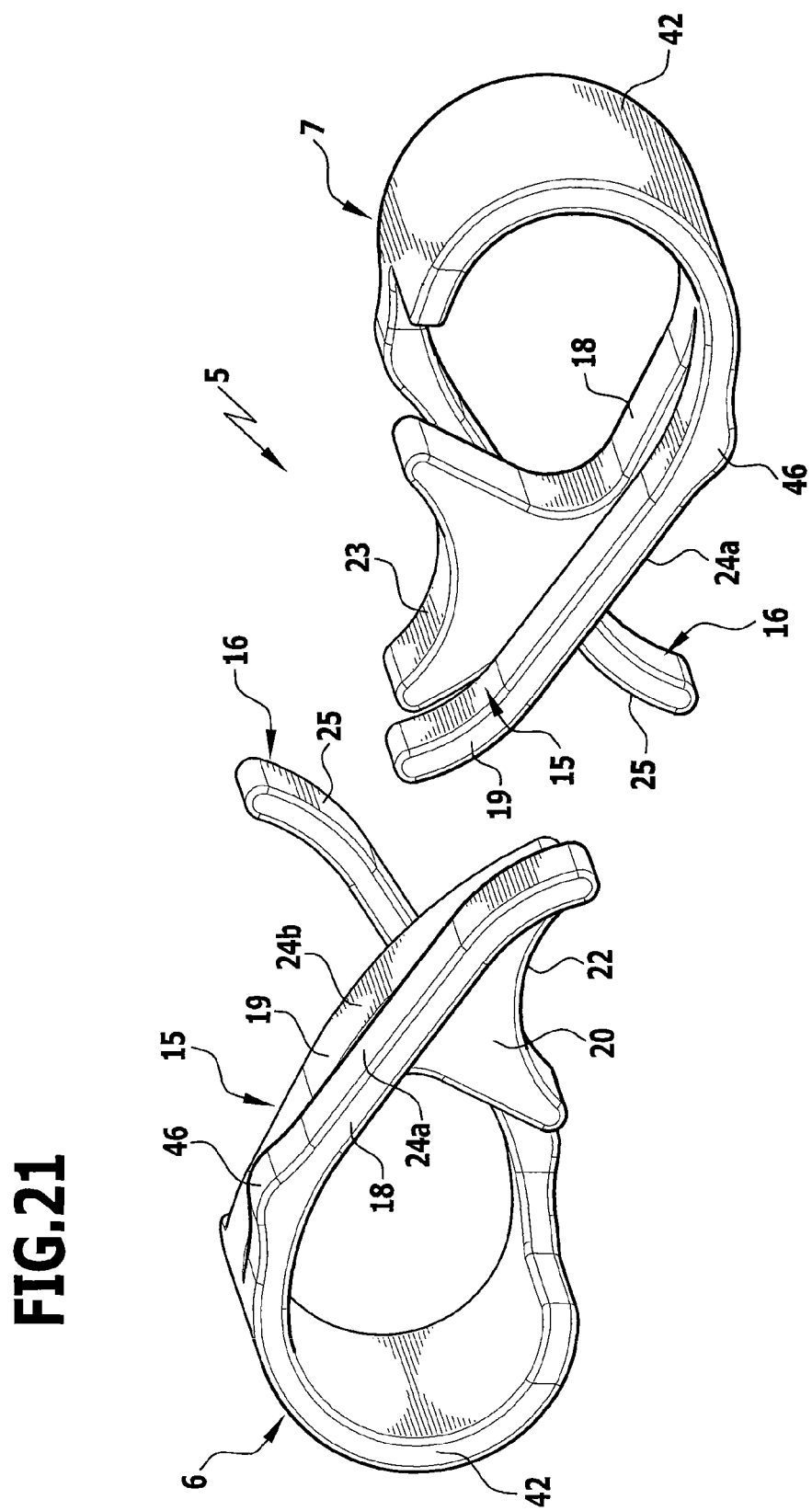
FIG. 21 is a perspective view of the implant components of the implant in FIG. 20 before being pushed together.

In the exemplary embodiment of FIGS. 20 and 21, each implant component has a support arm 15 slotted in the longitudinal direction and a support arm 16 that is not divided, wherein the two support arm sections 18, 19 of the slotted support arm 15 lie directly adjacent to one another. In a similar manner to that in the exemplary embodiment of FIGS. 1 to 9, the support arm section 19 of the divided support arm 15 located on the inside bears a projection 20 with a support surface 22, but this is the only projection with a support surface of this type on the implant component. The support arm section 18 and the second support arm 16 are not provided with such a projection and such a support surface. The support arm section 18 and the support arm 16 are configured as a thin web over the entire length, the thickness of said web corresponding to about the thickness of the web-shaped bridge section 42. The support arm section 19 with the projection 20 and the support surface 22 is located in the centre between the support arm section 18 and the support arm 16, wherein the two support arms 16 and the support arm section 18 located on the outside are identically configured with a substantially plane outer face 24a and 25 respectively, which merge into a raised section 46 in a similar manner to that in the exemplary embodiment of FIGS. 10 and 11. In the same way as has been explained in the other exemplary embodiments, when the two implant components are pushed together, the support arms slide on one another on their outer faces and thus cross over to a greater extent. This in the same way causes the two support surfaces 22, 23 to be moved away from one another, while also causing the relatively flexible support arm sections 18 and support arm 16 to bend outwards, i.e. relatively strongly as a result of their greater flexibility. The free ends of the support arm 16 and the support arm section 18 are bent up on both sides of the respective support surface 22 and 23, and thus form abutment elements projecting on both sides of the support surfaces, which, in a similar manner to the abutment elements 37 and 38 in the above-described exemplary embodiments, come to abut laterally against the spinous processes and thus secure the implant against lateral displacement. Therefore, in this exemplary embodiment, because of the different configuration of the support arms, the support arms with variably spaced support surfaces as well as the abutment elements for lateral abutment against the spinous processes are connected to form a single structural part, namely the respective implant component 6, 7.

Figure 22:
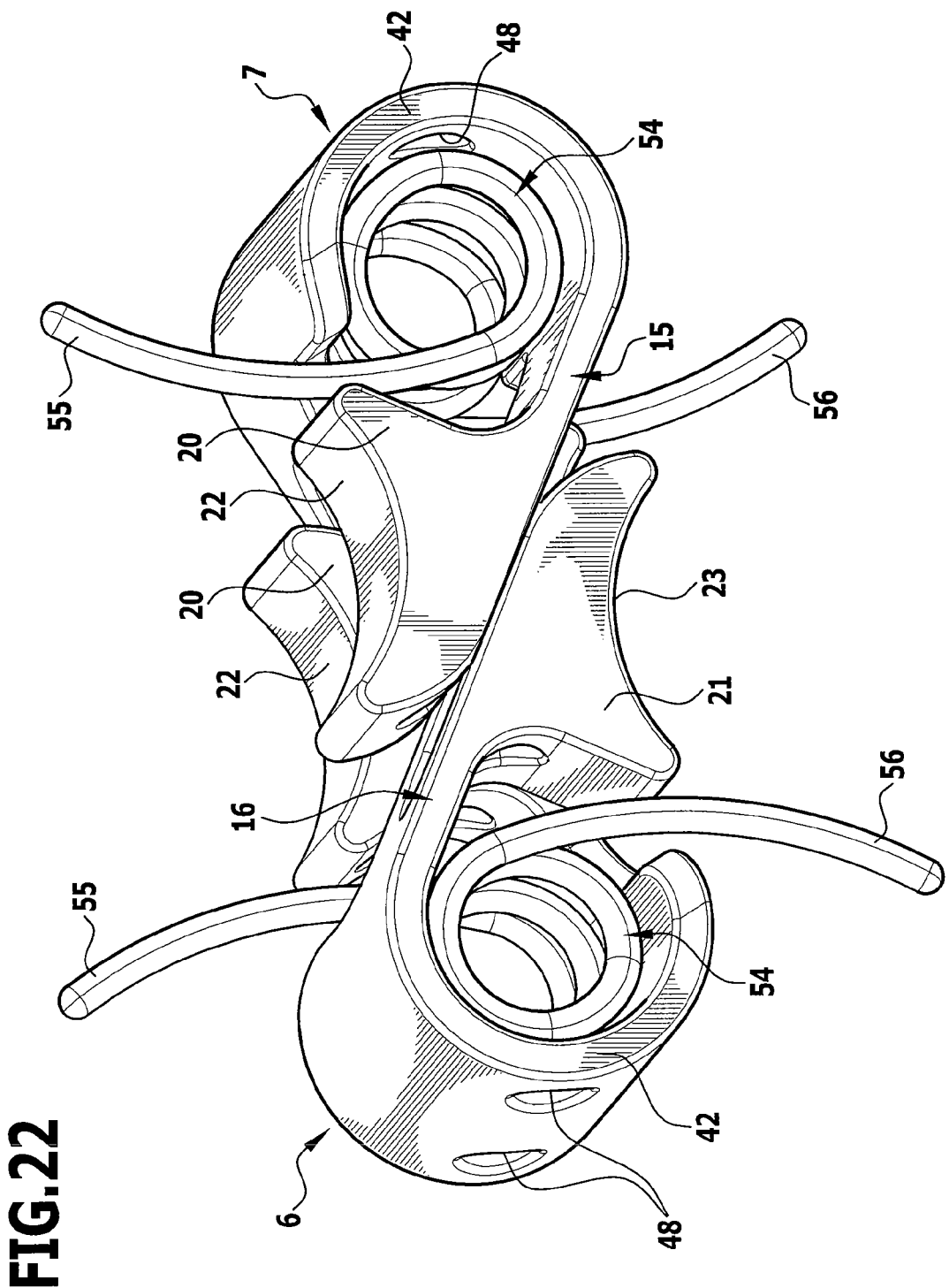
FIG. 22 is a perspective view of a further preferred exemplary embodiment of an implant with implant components pushed together and with abutment elements in the form of coil springs inserted and raised.
Figure 23:
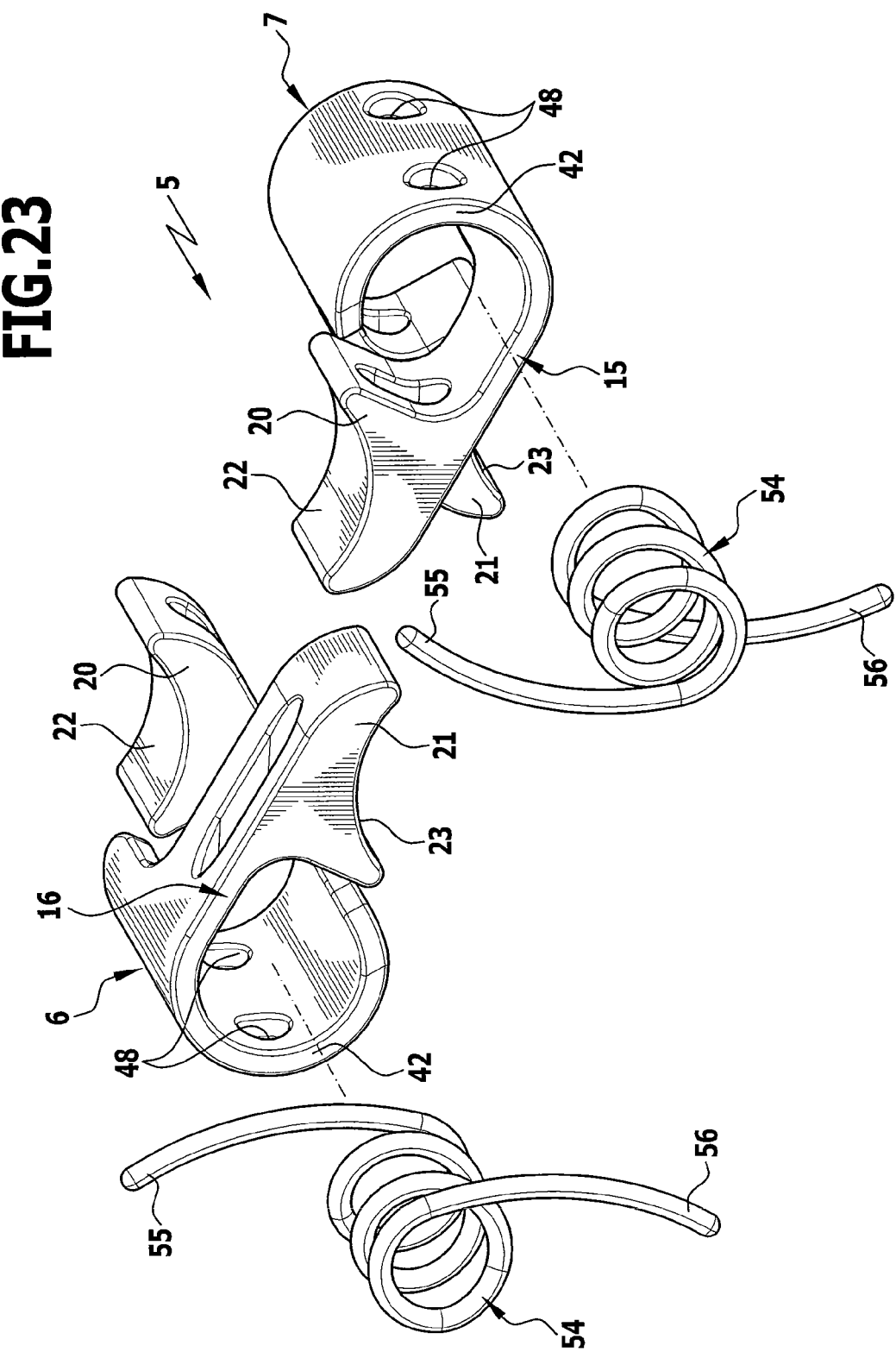
FIG. 23 is an exploded view of the implant of FIG. 23.
Figure 24:
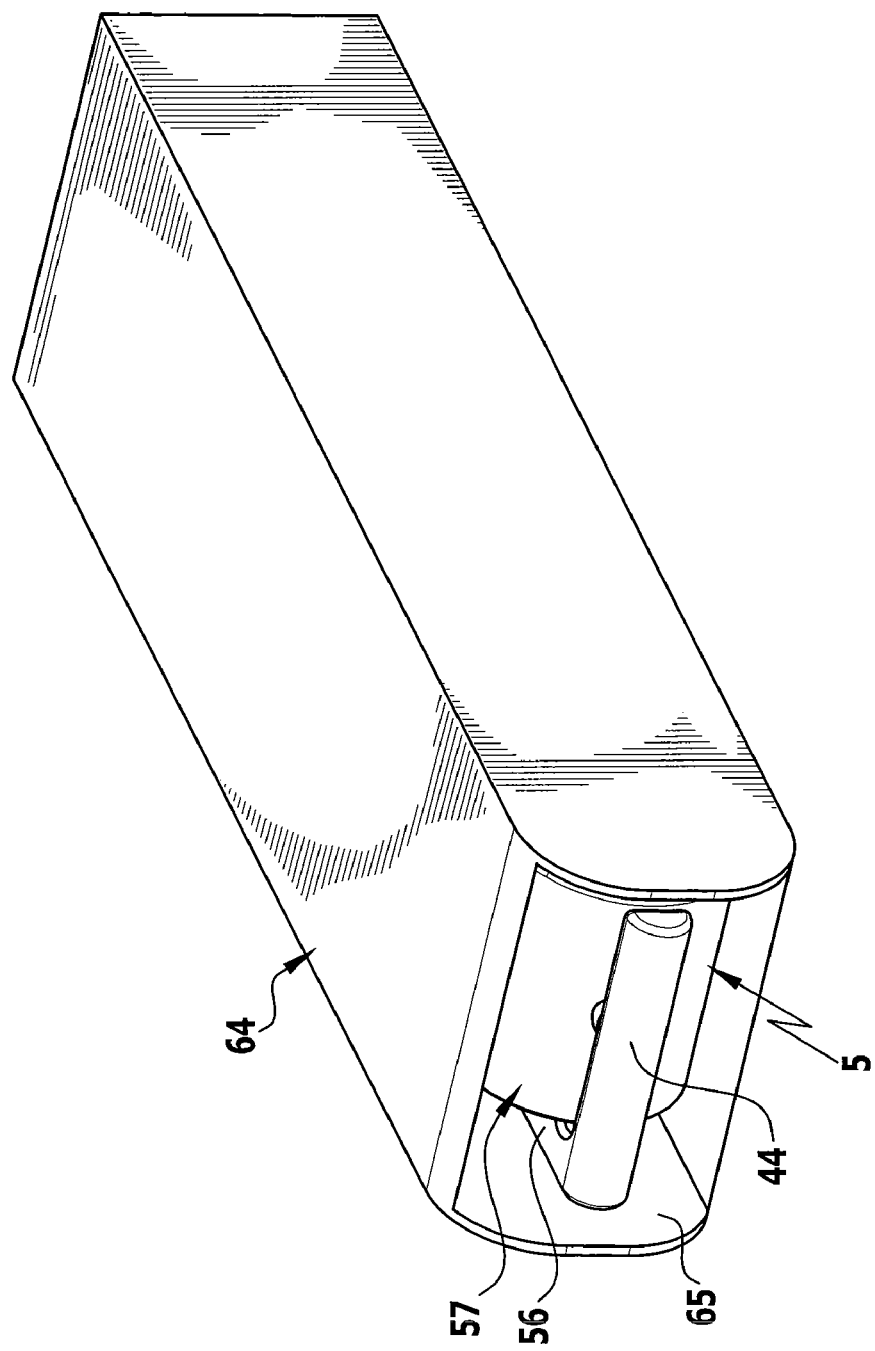
FIG. 24 is a perspective view of a further preferred exemplary embodiment of an implant in an insertion sleeve.

The exemplary embodiment shown in FIGS. 22 and 23 is similar in configuration to the exemplary embodiment of FIGS. 16 and 17. The two implant components bear unslotted support arms 15, 16 respectively with a projection 20, 21 and a support surface 22, 23. In order to shift the implant components 6, 7 towards one another, openings are provided in both implant components, both in the bridge section 42 and in the projections 20, 21 of the support arms 15, 16, through which openings the two adjacent tie bars can be directed, which are not shown separately in the drawing for reasons of clarity.

In addition, a coil spring 54, the longitudinal axis of which runs transversely to the support arms, is inserted into the interior of each implant component 6, 7, i.e. in the area enclosed as far as the crossover point by the bridge section 42 on one side and by the support arms 15, 16 on the other side, so that the coil spring abuts against the inner surface of the bent bridge section 42 with its periphery. The free ends 55, 56 of the coil spring 54 project outwards next to the support arms 15, 16 and project outwards approximately transversely to the longitudinal direction of the support arms, i.e. on both sides of the support surfaces 22, 23. They thus form abutment elements for fixture of the implant on the side faces of the spinous processes. During implantation of the implant the free ends can be bent down as a result of the spring action of the coil spring 54 so that they run approximately in the longitudinal direction of the support arms and do not project outwards, and therefore the structural height remains low and the free ends do not hinder the insertion. As soon as the implant is inserted between the spinous processes, the free ends can be released and then spring into the position shown in FIG. 22, in which they form abutment elements for the spinous process on both sides of the support surface.

In the exemplary embodiment of FIGS. 24 to 28, the two implant components are similar in configuration to those in the exemplary embodiment of FIGS. 22 and 23, only the openings in the bridge section and in the projections for passage of the tie bars are absent.

Each implant component 6, 7 is surrounded by a clamp 57, 58, and these are identical in structure and therefore only one of the two clamps 57 will be described in more detail below. This clamp comprises a web-shaped, curved central section 59, which abuts flat against the curved bridge section 42 of the implant component 6, 7 on the outside and which extends over a circumferential region that is larger than 180°, so that this central section 59 is held on the implant component because it surrounds the bridge section 42 over an angular range of more than 180°. The central section 58 can be able to bend elastically upwards, so that the clamp 57 can be pushed on the bridge section 42 with widening of the central section 59 and in the pushed-on position is fixed in this position by a narrowing of the central section 59.

At its ends the central section 59 bears a substantially strip-shaped, outwardly curved web 60, 61 on both sides, these webs being arranged laterally adjacent to the two support arms 15, 16 of the implant components 6, 7, so that the support surfaces 22, 23 of the implant components 6, 7 lie between these webs 60, 61. The outwardly curved webs 60, 61 of the clamps 57, 58 placed on the implant components 6, 7 abut with their inner surfaces against slide faces 62, 63, which are located on the outside of the bridge sections 42 of the two implant components 6, 7, i.e. directly adjacent to the point of departure of the respective support arm 15, 16 from this bridge section 42. When the two implant components 6, 7 are pushed together, the two webs 60, 61, which in contrast to the support arms 15, 16 do not cross over one another, are thus pivoted outwards and on both sides of the support surfaces 22, 23 form lateral abutment elements, which abut against the side face of the spinous process.

Therefore, in this exemplary embodiment the abutment elements are configured as separate parts, which are arranged on the clamps 57, 58 slid onto the implant components 6, 7 and which are pivoted into their abutment position by sliding on the outer surface of the opposing implant components.

In this way, an implant can be selectively inserted either without these clamps 57, 58 or with these clamps 57, 58. The surgeon can decide at a moment's notice whether the clamps 57, 58 will be attached and abutment elements thus created, or whether this is not necessary.

Figure 25:
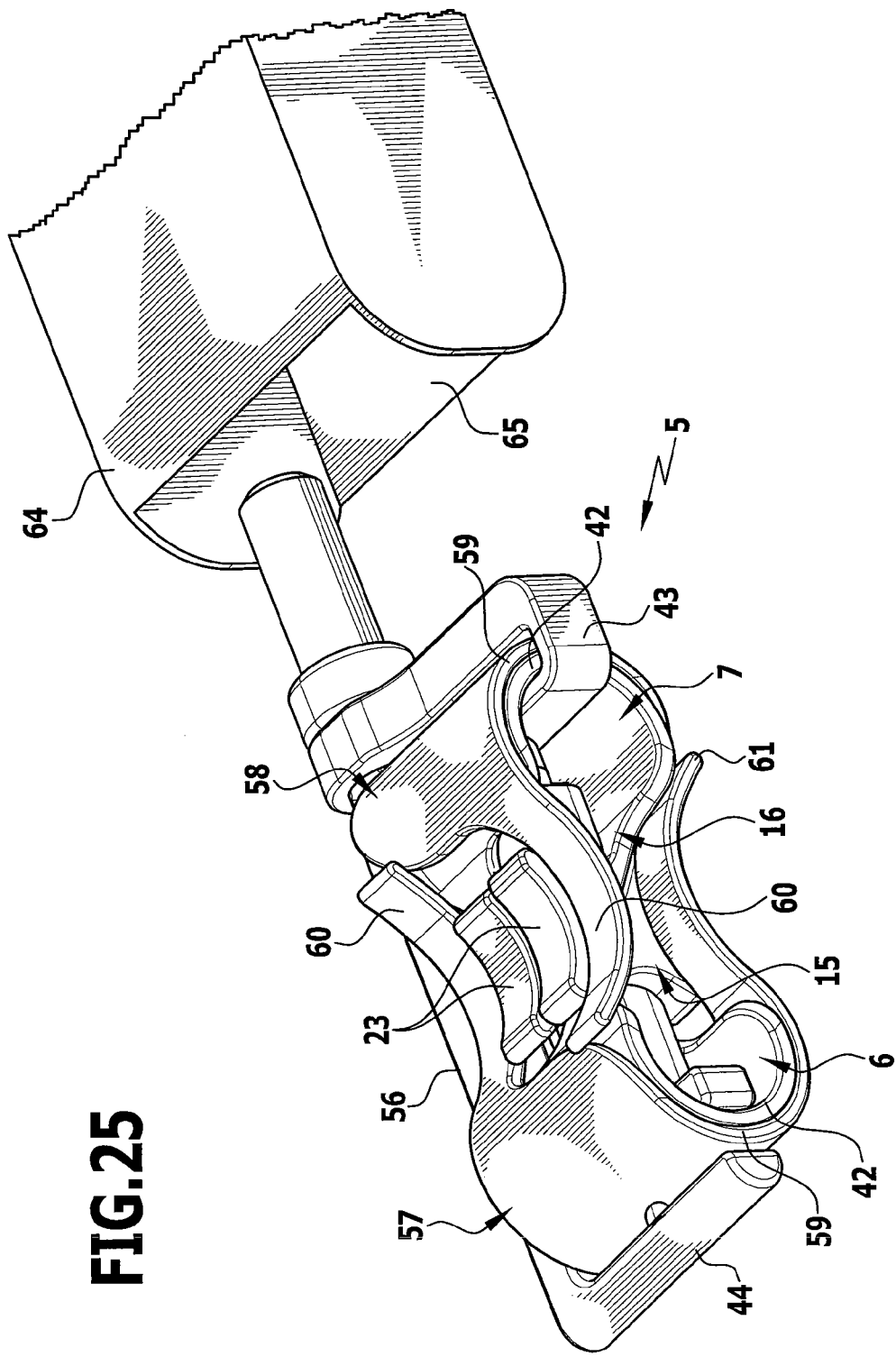
FIG. 25 is a perspective view of the implant of FIG. 24 after removal from the insertion sleeve.
Figure 26:
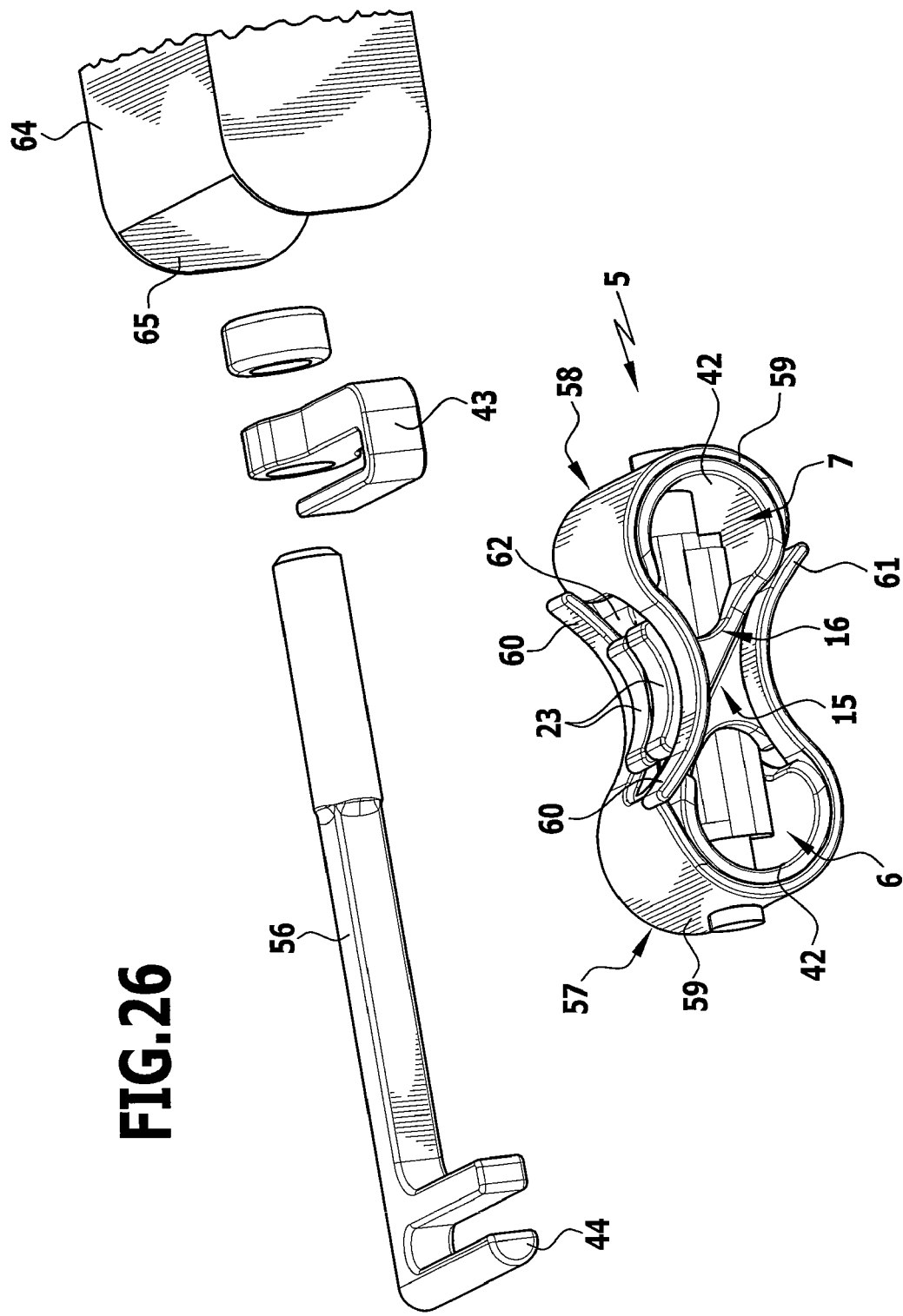
FIG. 26 is an exploded view of the implant of FIGS. 24 and 25.
Figure 27:
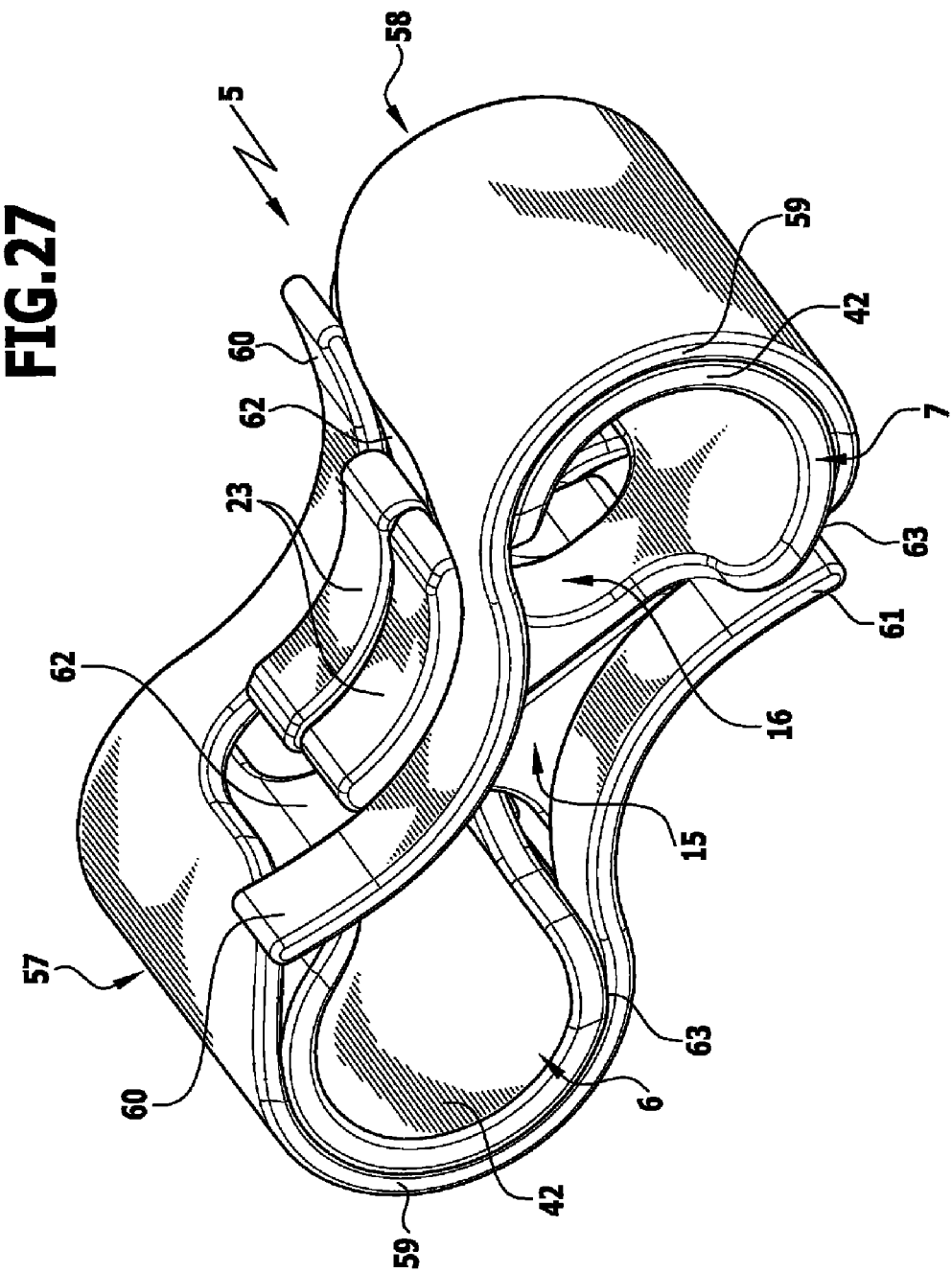
FIG. 27 is a perspective view of a further preferred exemplary embodiment of an implant with clamps with arm-like abutment elements attached to the implant components.

In order to push the implant components together, end pieces 43, 44 can abut against the outer surface of the clamps 57, 58, one of the end pieces being connected in one piece to a tie bar 56, whereas the other is longitudinally displaceable on this tie bar (FIG. 25). In this regard, a construction results that is similar to the construction in the exemplary embodiment of FIGS. 7 to 9 results, with the difference that a tie bar is only arranged on the implant on one side.

In the exemplary embodiment of FIGS. 24 to 28, an elongated, cuboidal casing 64 is additionally shown with an opening 65 on one face, into which the implant of FIGS. 25 to 28 is inserted. In this way, the implant is kept in the casing 64 and can also be implanted in this form. In this case, the casing protects both the implant and the surrounding tissue and can be removed from the implant after its insertion. In this case, in the manner evident from FIG. 25, the implant emerges from the interior of the casing 64 and by bringing the end pieces 43, 44 closer together in the manner described above, can then be brought into the final position, in which the spacing of the support surfaces 22 and 23 is adjusted and in which at the same time the webs 60, 61 are bent outwards.

Figure 29:
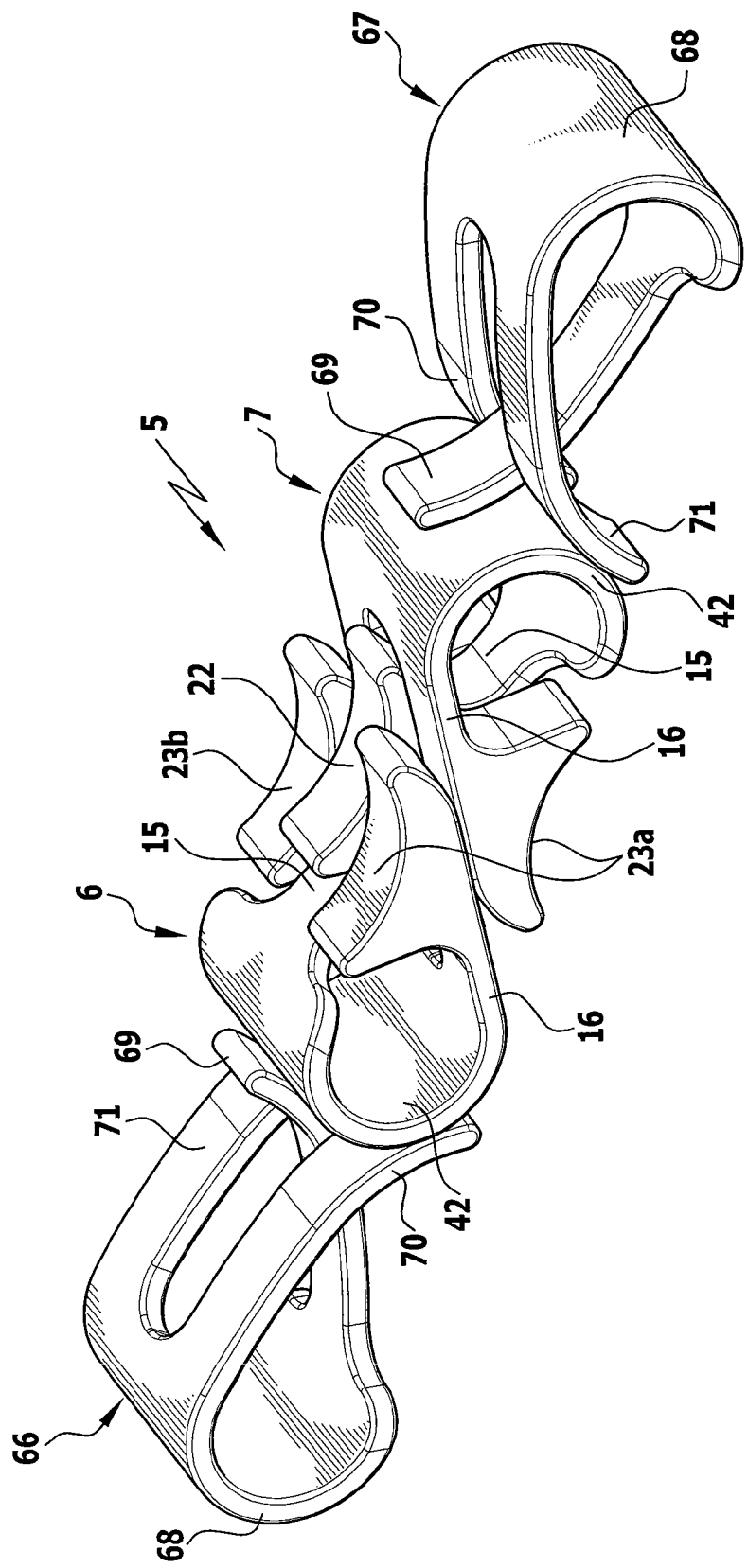
FIG. 29 is a perspective view of a further preferred exemplary embodiment of an implant with clamp-like abutment elements arranged adjacent to the implant components.
Figure 30:
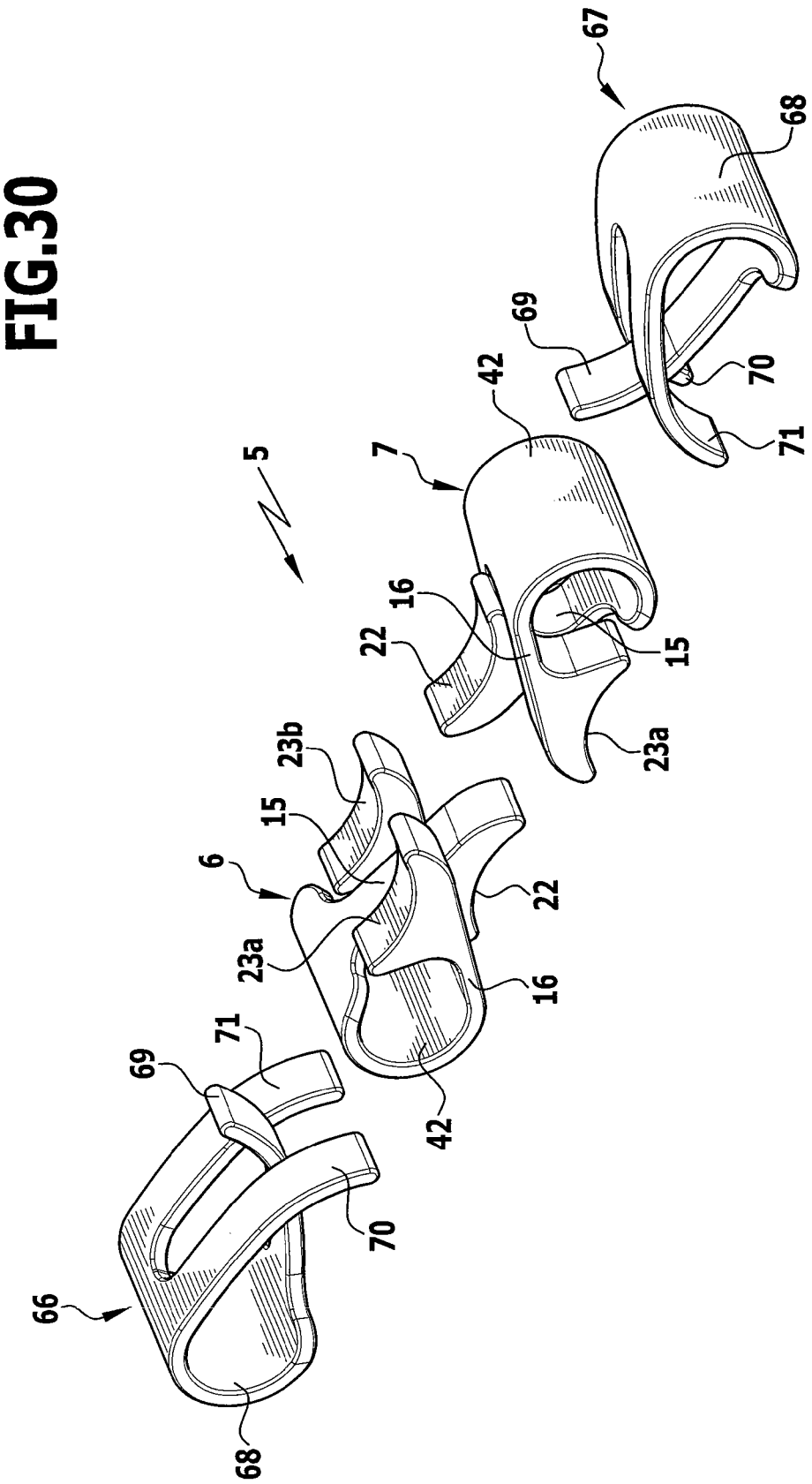
FIG. 30 is an exploded view of the implant of FIG. 29.

In the exemplary embodiment of FIGS. 29 and 30, the implant components 6, 7 are configured as in the exemplary embodiment of FIGS. 7 to 9. In addition to the implant components, similarly configured slide clamps 66, 67 are applied, which are configured identically and of which therefore only slide clamp 66 will be explained in more detail.

This slide clamp 66 is configured in the shape of a band with a curved, band-like bridge section 68, which at one end bears a central substantially rectilinear web 69 and at the other end bears two parallel and spaced webs 70, 71, wherein the central web 69 penetrates into the interstice 72 between the webs 70, 71, so that the webs 79 on one side and webs 70 and 71 on the other side cross over one another. All webs 69, 70, 71 are bent down towards the outside at their free ends and with their respective outer faces abut against the outer surface of the bridge section 42 of a respective implant component 6, 7. Thus, the two implant components 6, 7 are arranged one behind the other and on opposite sides of the slide clamps 66, 67.

By means of elements not visible in the drawing, the slide clamps 66, 67 can be pushed towards one another, and thus push the implant components 6, 7 towards one another, so that the support surfaces 22 and 23 are moved away from one another in the above-described manner, while the relatively flexible webs 69, 70, 71 arranged on the slide clamps 66, 67 also cross over one another to a greater extent and are twisted so that after the pushing together they project upwards and downwards from the implant on both sides of the support surfaces 22, 23 and form abutment elements, which can abut laterally against the spinous processes.

Therefore, it is also possible in the case of this implant to implant the implant either without the slide clamps 66, 67 or additionally with the slide clamps 66, 67. When the slide clamps 66, 67 are used, these form the elements, with which the implant components 6, 7 are pushed towards one another, while the lateral abutment elements are also formed on both sides of the support surfaces. Slide clamps 66, 67 of this type can also be used in other configurations of the implant components 6, 7. The above-described embodiments are distinguished in that the support arms of an implant component cross over one another and the crossover is further reinforced by pushing two implant components together, and hence the support arms are spread at their free ends. Accordingly, the support surfaces are respectively arranged on the inner surfaces of the support arms and are inclined relative to the support arms so that the support surfaces are arranged substantially parallel to one another and parallel to the displacement plane of the implant bodies on the upper side and on the underside of the implant.

In the embodiments described below on the basis of FIGS. 31 to 44, another construction of the implant bodies 6, 7 is selected. However, these are still so similar in configuration that corresponding parts are given the same reference numerals. In contrast to the above-described exemplary embodiments, in these exemplary embodiments the support arms do not cross over one another, but run substantially parallel to one another and parallel to the displacement plane of the implant components, i.e. the implant components 6, 7 largely have the shape of a U, wherein the support arms form approximately parallel running legs and are connected at one end by means of a bridge section 42.

While the support arms in the exemplary embodiments of FIGS. 1 to 30 abut against the outer faces of the support arms of the respective other implant body with their outer faces and thus cross over one another to a greater extent when pushed together, the support arms in the exemplary embodiments of FIGS. 31 to 44 abut against slide faces 72, 73 of the respective other implant component with their inner surfaces. In this case, these slide faces 72, 73 are respectively arranged in the transition region between the bridge section 42 and the support arms 15, 16 of an implant component, i.e. next to the support arms of the implant components bearing the slide face.

Figure 31:
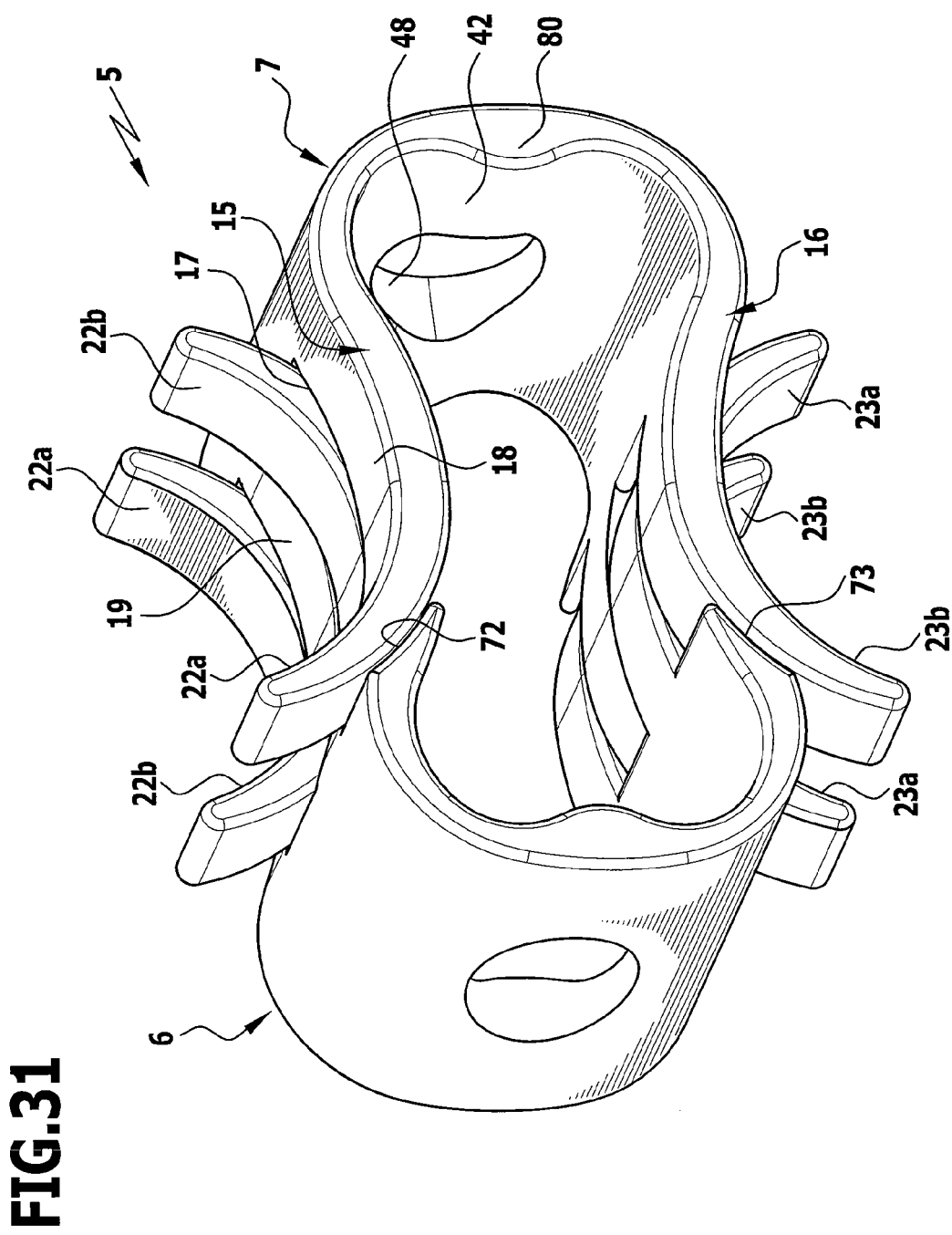
FIG. 31 is a perspective view of a further preferred exemplary embodiment of an implant with support arms, which do not cross one another.
Figure 33:
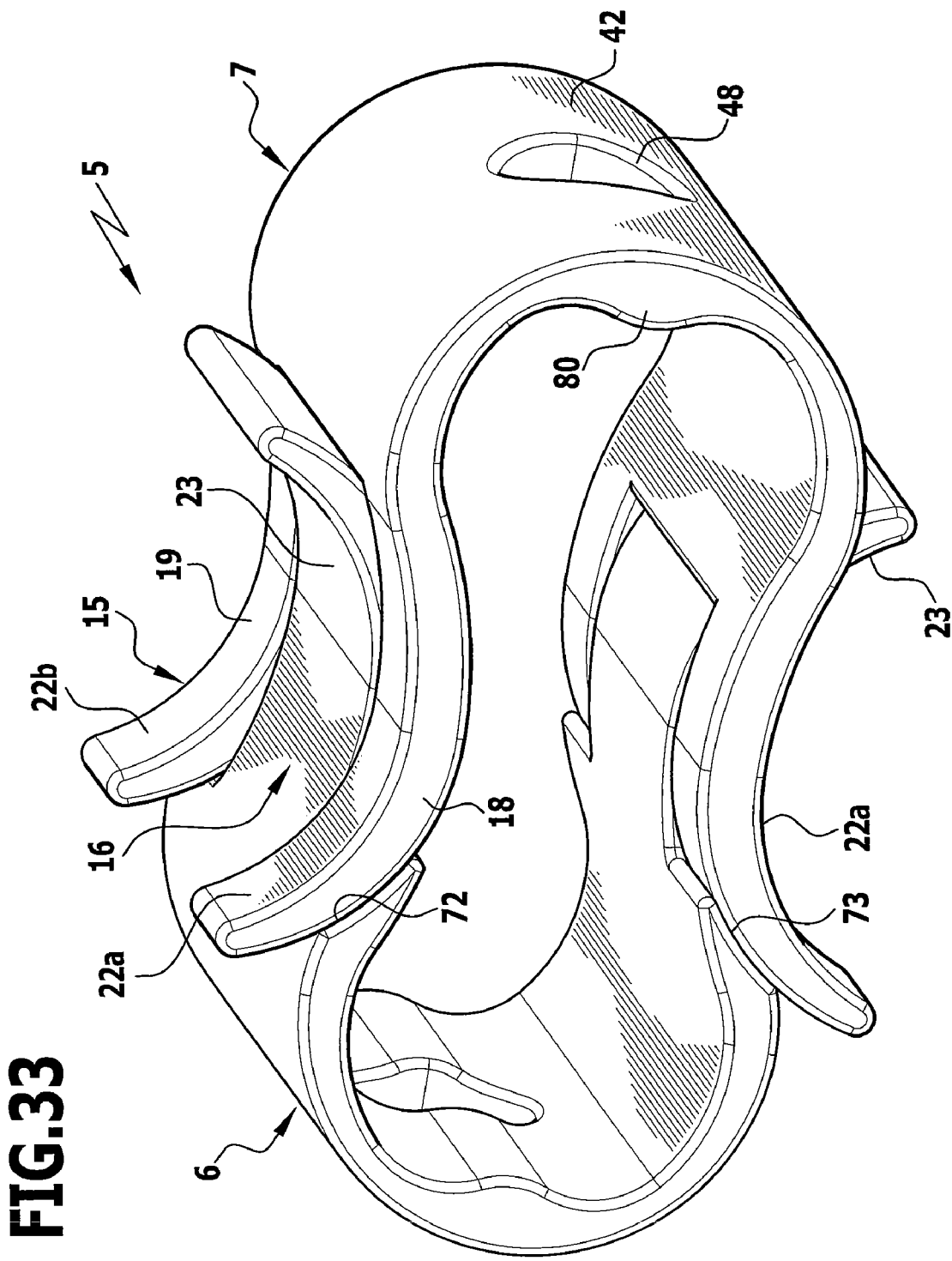
FIG. 33 is a perspective view similar to FIG. 31 of a further preferred embodiment of an implant.

In the exemplary embodiment of FIGS. 31 and 33, the support arms 15, 16 are respectively divided into support arm sections 18, 19 by means of a longitudinal slot 17, so that four support arm sections 18, 19 are respectively arranged overall on the upper side and on the underside of the implant, and these support arm sections intermesh with one another in the manner of a comb, are respectively supported with their inner faces against a slide face 72, 73 of the respective other implant component and are thus bent outwards when the implant components 6, 7 are pushed together, i.e. the support arms 15, 16 of each implant component 6, 7 are pivoted downwards or spread apart on their entire length when the implant components are pushed together, so that the spacing of their outer faces is increased.

In this case, the support arms are concavely curved in all cases, so that concavely curved support surfaces 22, 23 are formed on the outer faces of the support arms as a result of these, wherein the spacing of said support surfaces can be increased by the implant components 6, 7 being pushed together.

Figure 32:
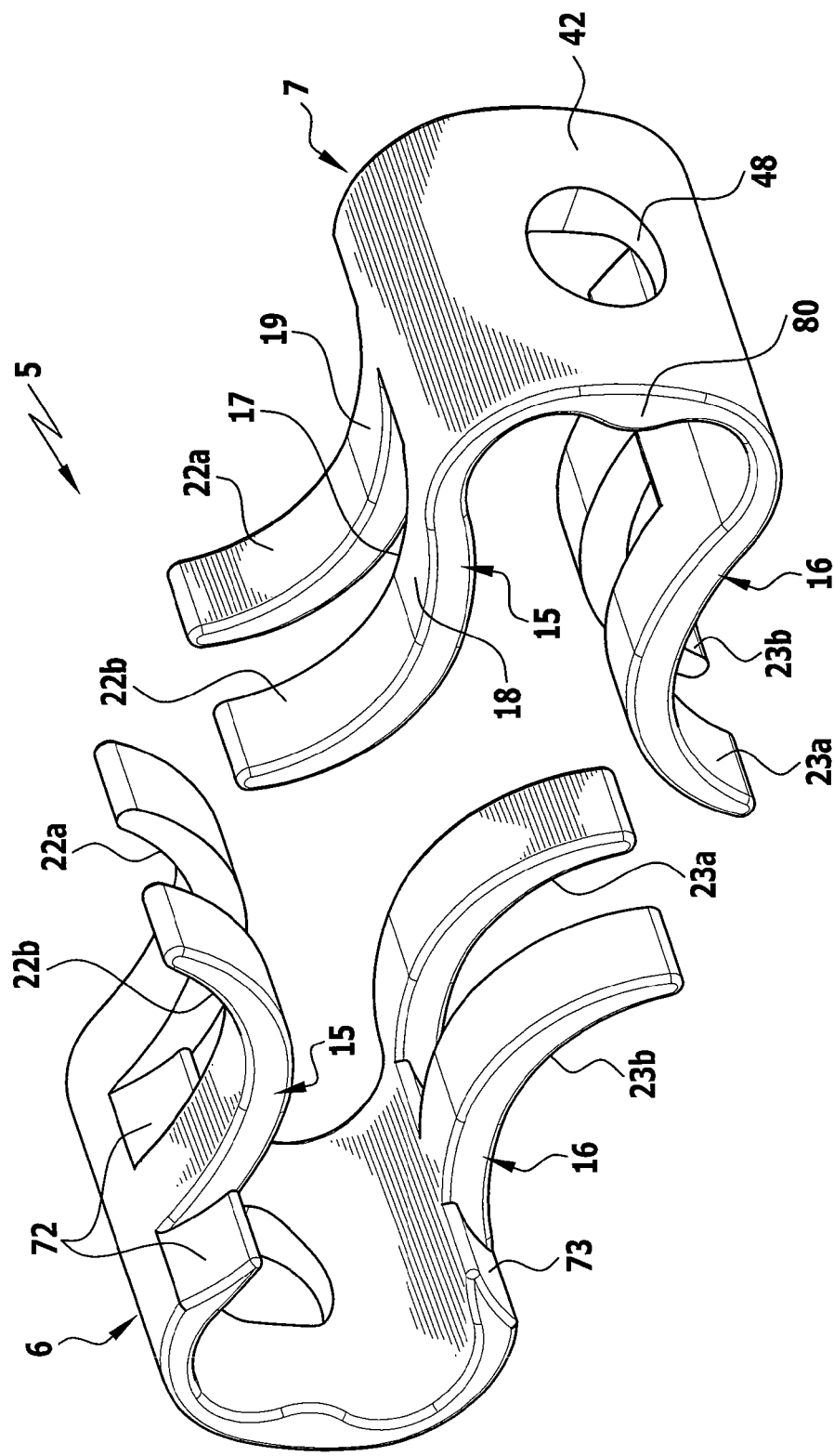
FIG. 32 is an exploded view of the implant components of the implant of FIG. 31.
Figure 34:
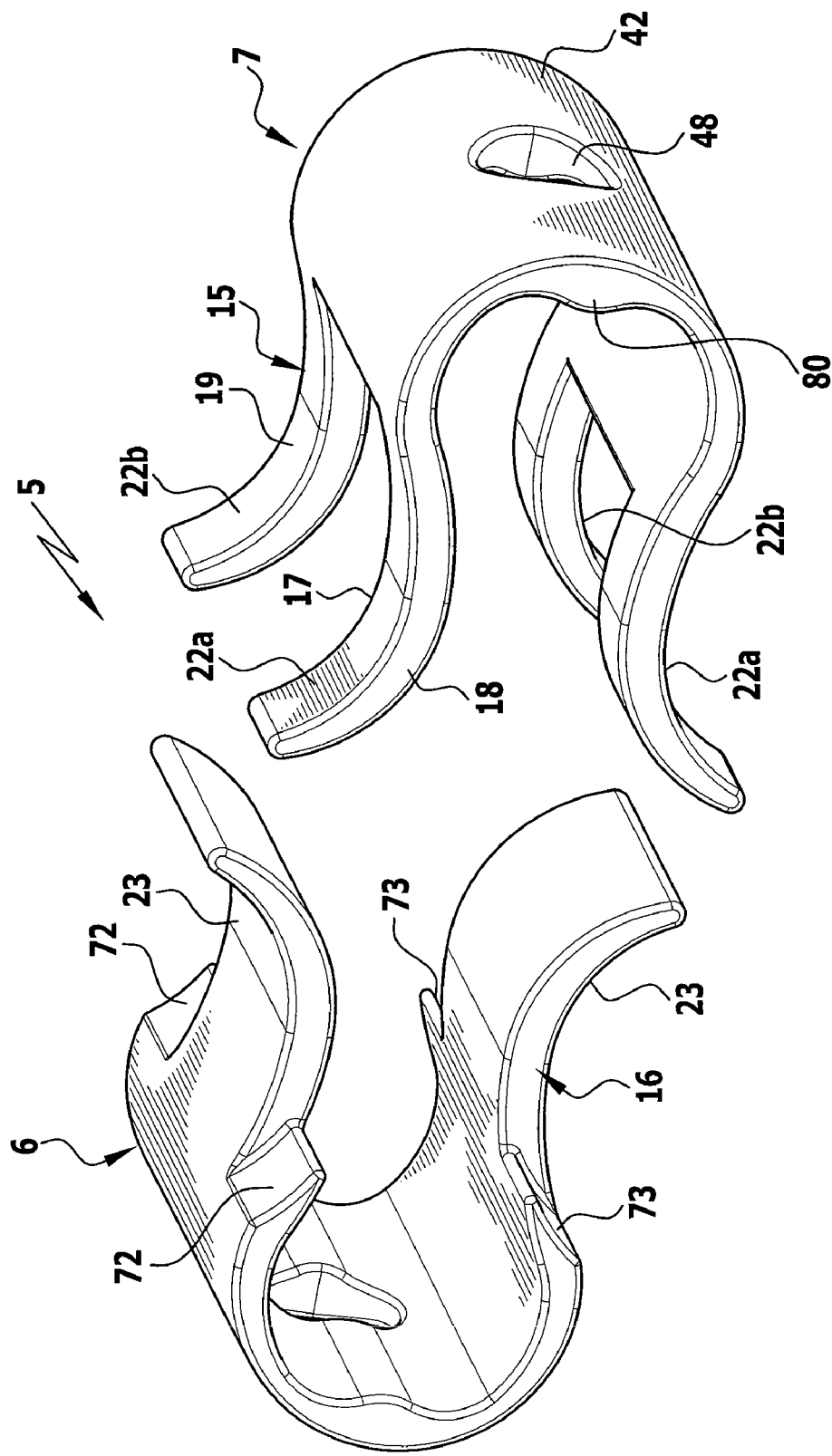
FIG. 34 is an exploded view of the implant of FIG. 33.

While in the exemplary embodiment of FIGS. 31 and 32 the support arms are configured in pairs on the upper side and the underside of both implant components, so that the implant components 6, 7 are configured identically to one another, in the implant of FIGS. 33 and 34 two differently configured implant components 6, 7 are used, namely a first implant component 6, which respectively bears only one central support arm 15 on the upper side and on the underside, and also a second implant component 7, which on the upper side and underside bears two parallel running support arm sections 18, 19, which form a spacing between them and receive the support arm 15 of the other implant component 5 between them.

Figure 35:
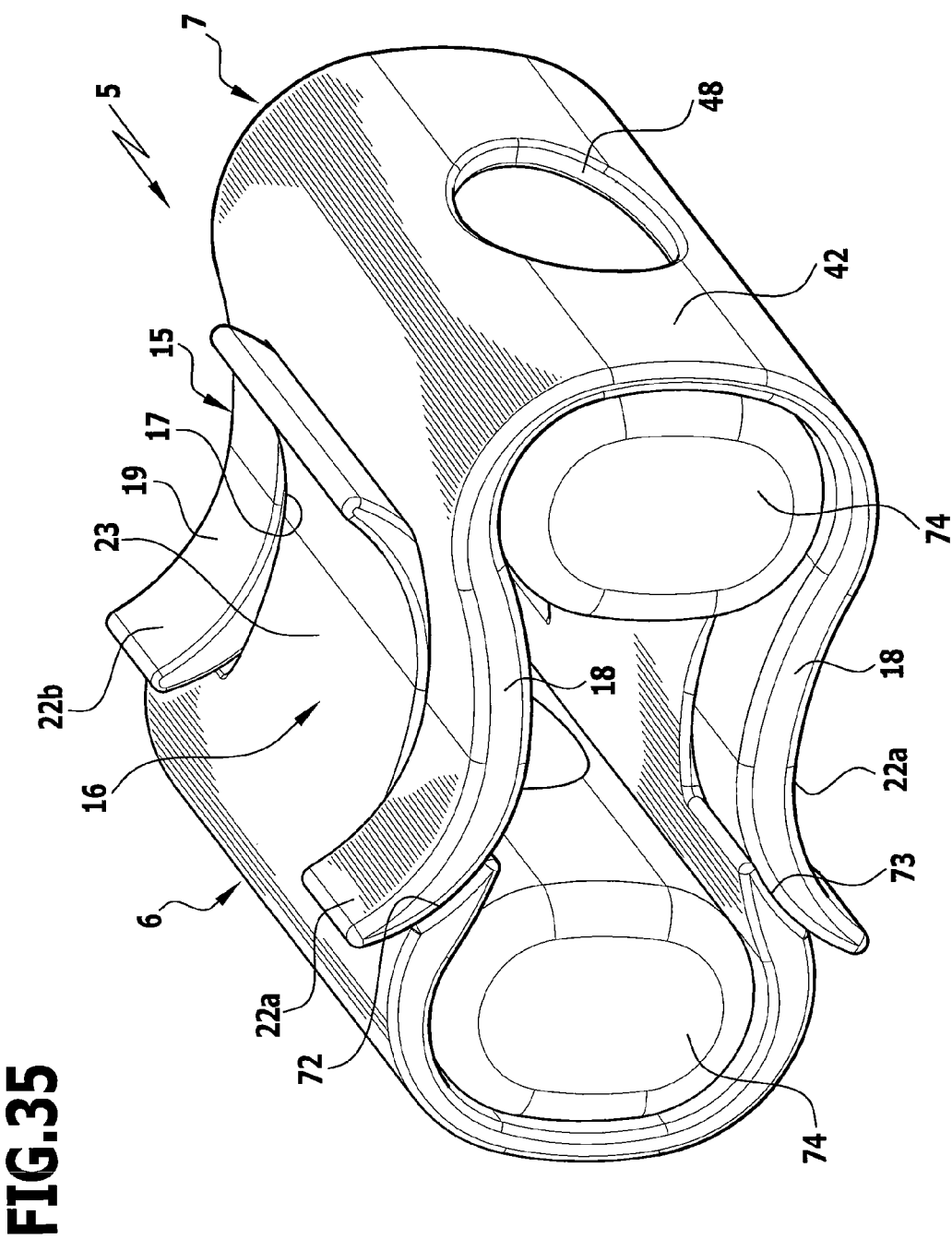
FIG. 35 is a perspective view of an implant similar to FIG. 33 with cores inserted into the interior.
Figure 36:
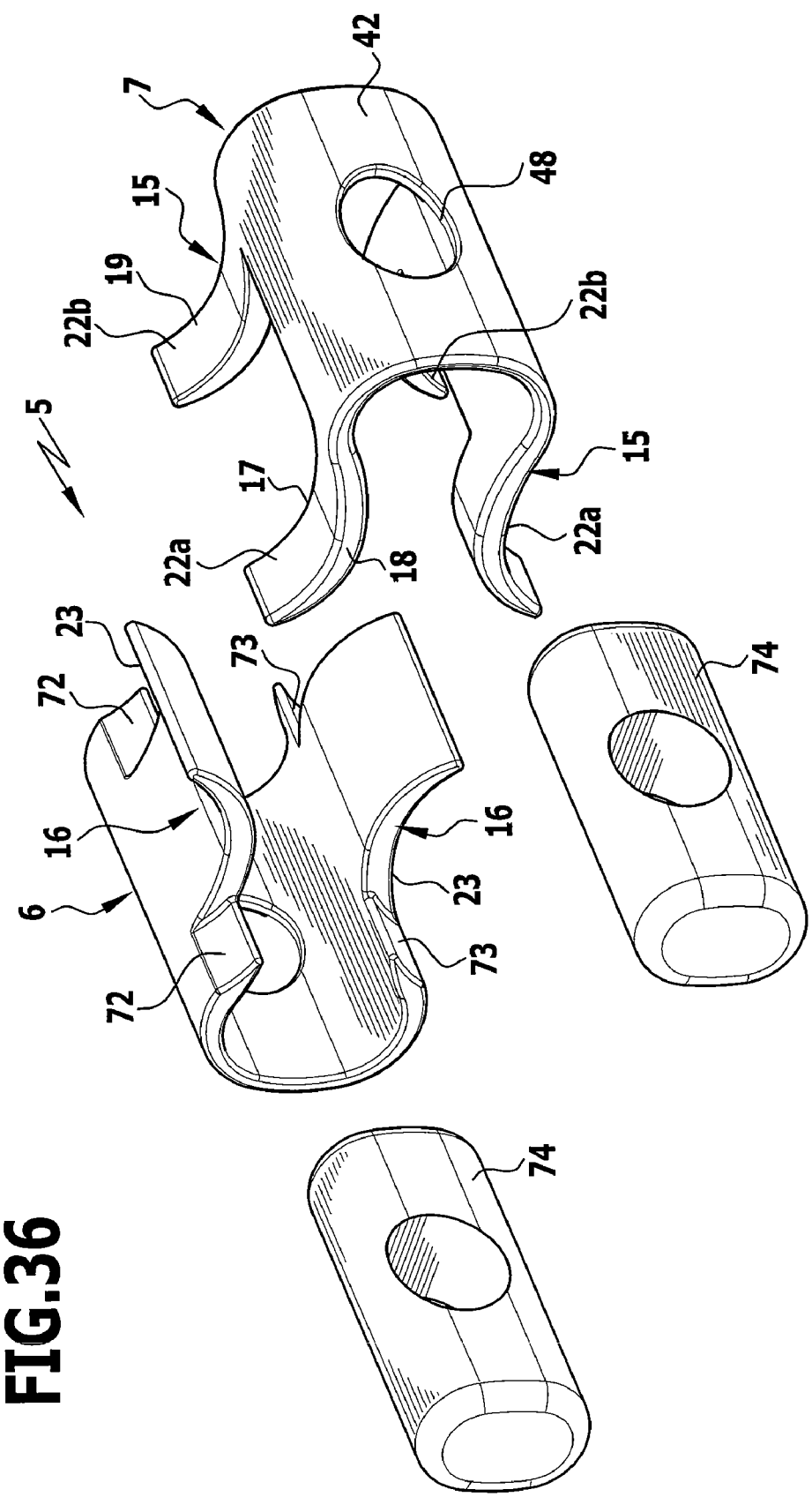
FIG. 36 is an exploded view of the implant of FIG. 35.
Figure 37:
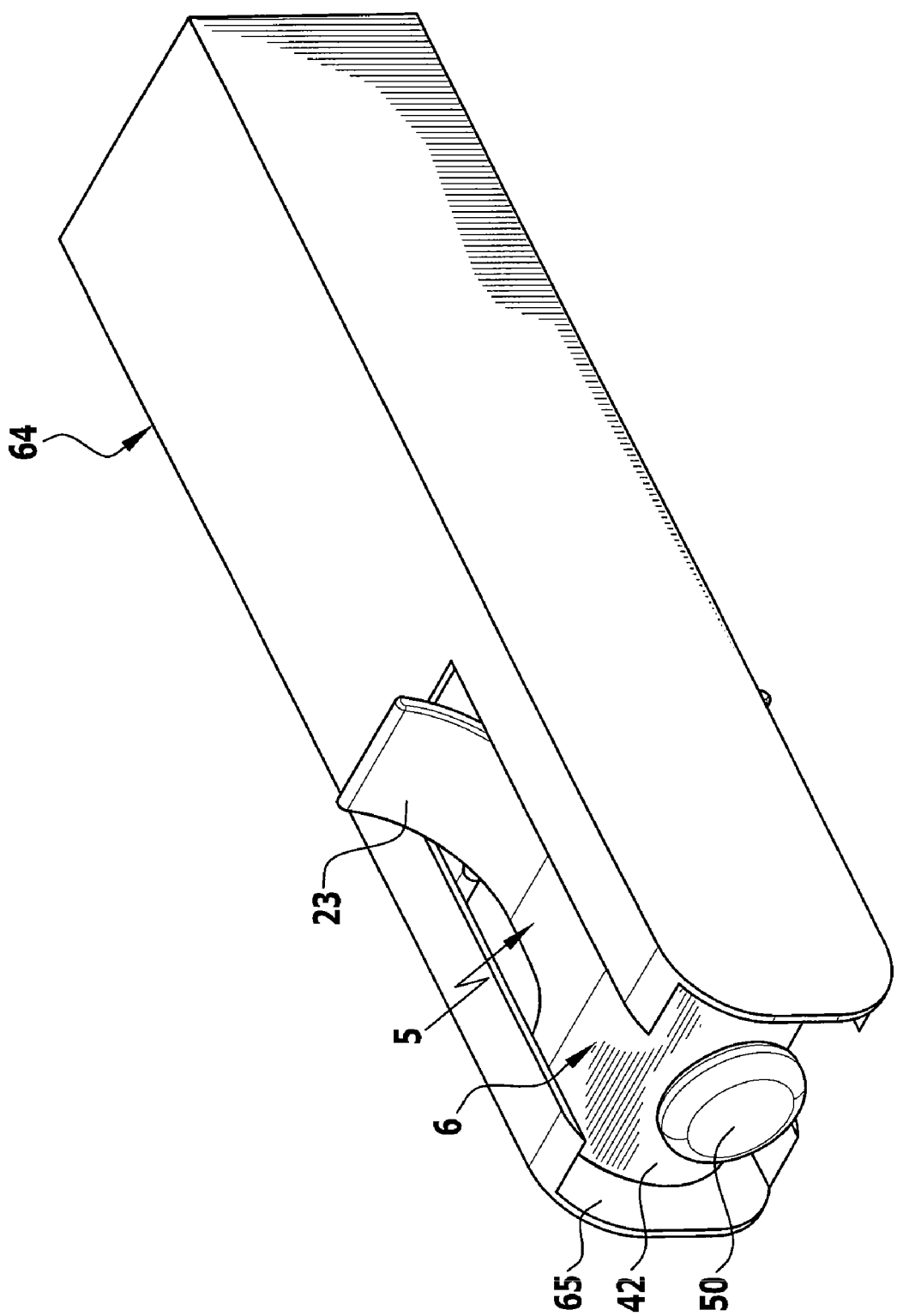
FIG. 37 is a perspective view of a further preferred exemplary embodiment of an implant in an insertion casing.
Figure 38:
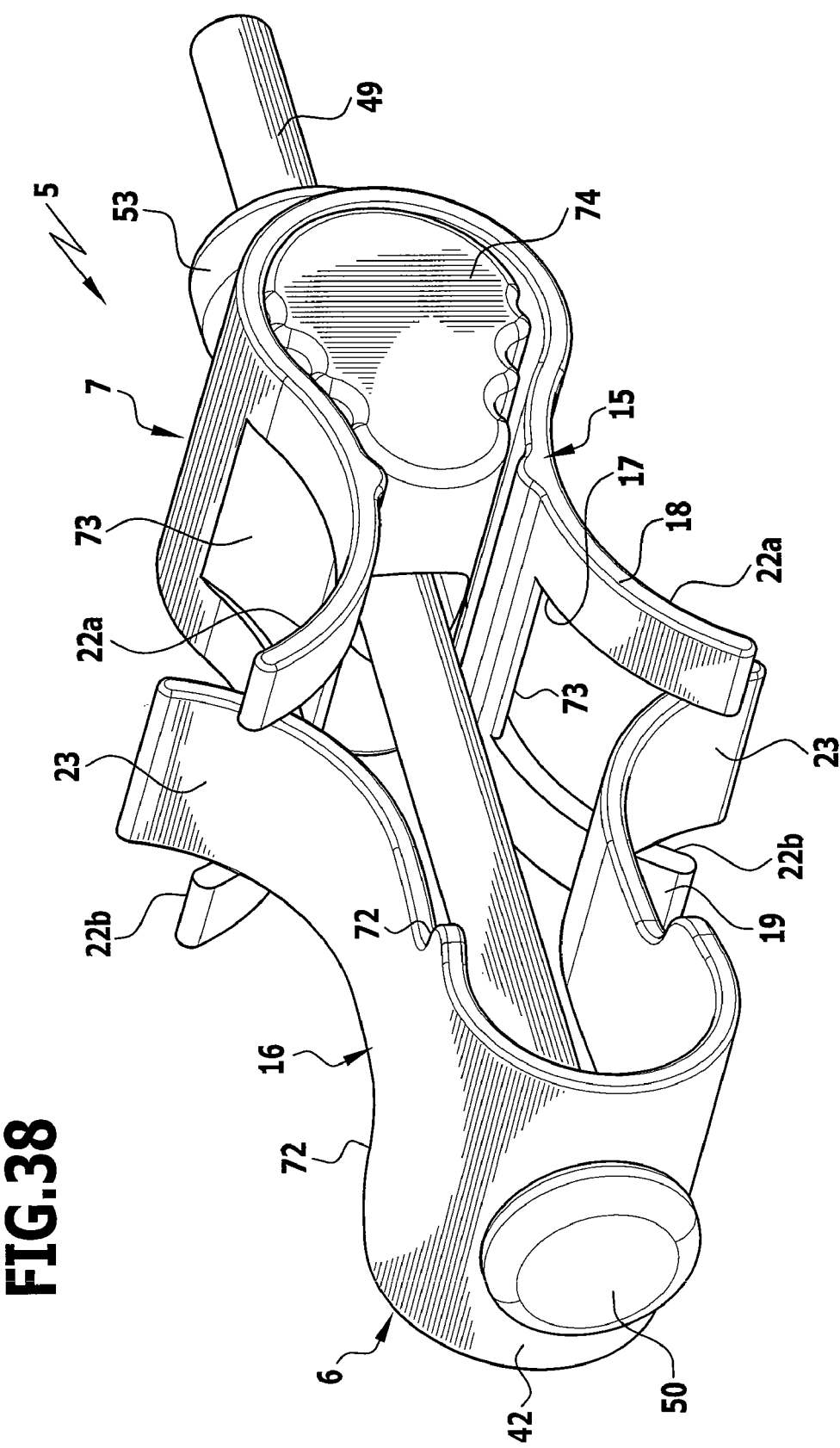
FIG. 38 is a perspective view of the implant of FIG. 37 after removal from the insertion casing.
Figure 39:
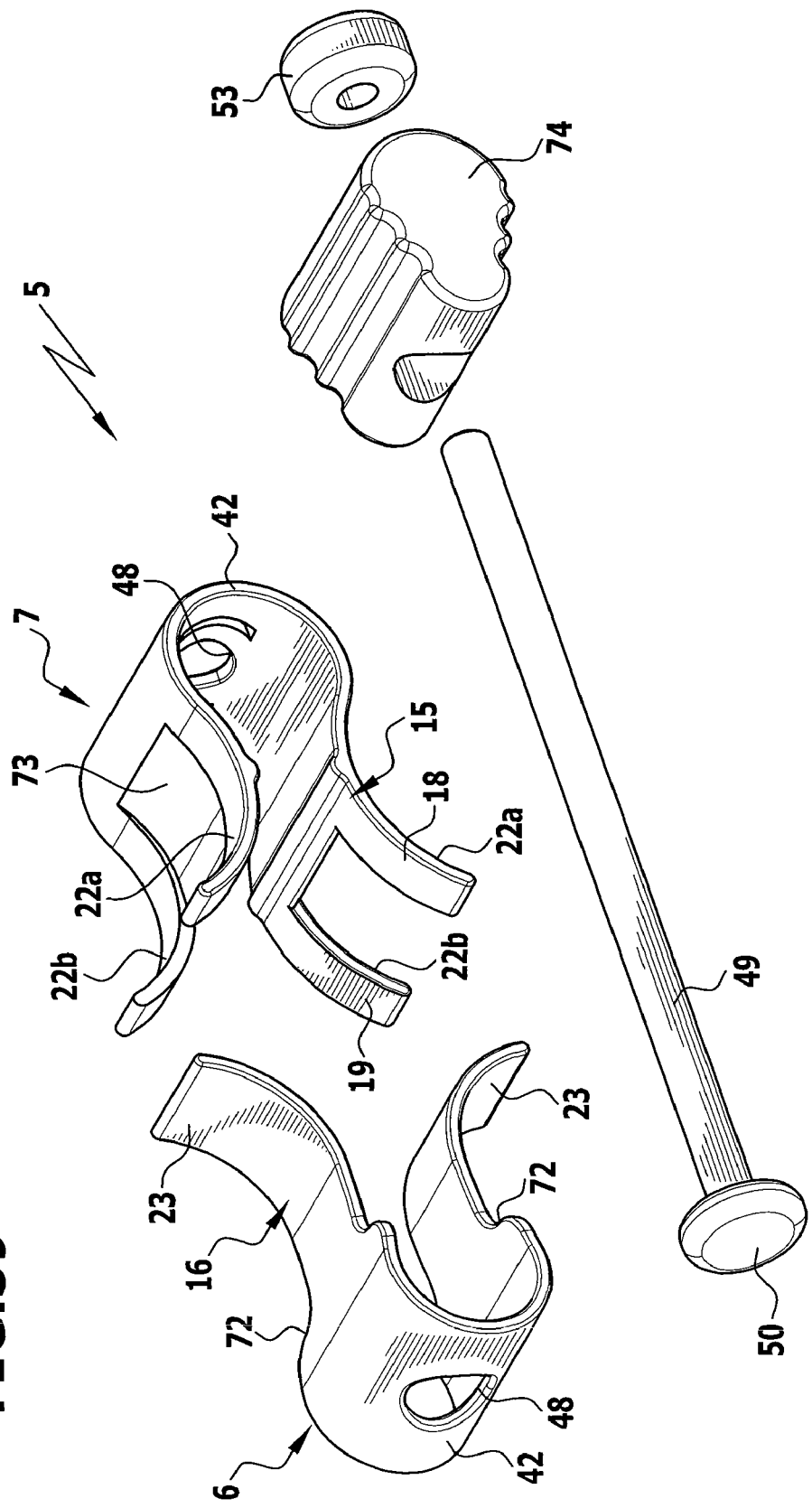
FIG. 39 is an exploded view of the implant of FIG. 38.

A core 74 can be respectively inserted into the interior of the implant components, i.e. into the area enclosed by the bridge section 42, as is shown in FIGS. 35 and 36. Such cores can also be used in all the other exemplary embodiments, possibly also only in one of the two implant components, as is shown in FIGS. 38 and 39. These cores can have a through-hole, through which a tie bar 26 can be directed, with which the two implant components 6, 7 are clamped against one another when in pushed together state.

It is also possible in these exemplary embodiments to arrange the implant in a casing 64 and after insertion remove it from this through an opening 65 of the casing 64. The implant of FIGS. 38 and 39 is shown in such a casing 64 in FIG. 37.

While in the embodiments described thus far the bridge section 42 is curved largely continuously or is configured in two parts, other cross-sectional forms can also be used. In the exemplary embodiment of FIGS. 40 and 41, for example, which otherwise largely corresponds to that of FIGS. 34 and 35, the bridge section 3 has plane faces 75, 76, 77, which run substantially perpendicularly to one another and are respectively connected to one another by means of a rounded edge region 78, 79.

In all embodiments, the bridge section 42 can be reinforced, e.g. by an increase of the wall thickness. In the exemplary embodiments of FIGS. 31 to 33 and also 40 and 41, this is achieved by a projection 80 on the inner surface of the bridge section 42. This reinforcement of the wall is particularly advantageous when an opening 48 for a tie bar is provided in the bridge section 42, and thus the stability in this region is assured in spite of this opening.

Figure 40:
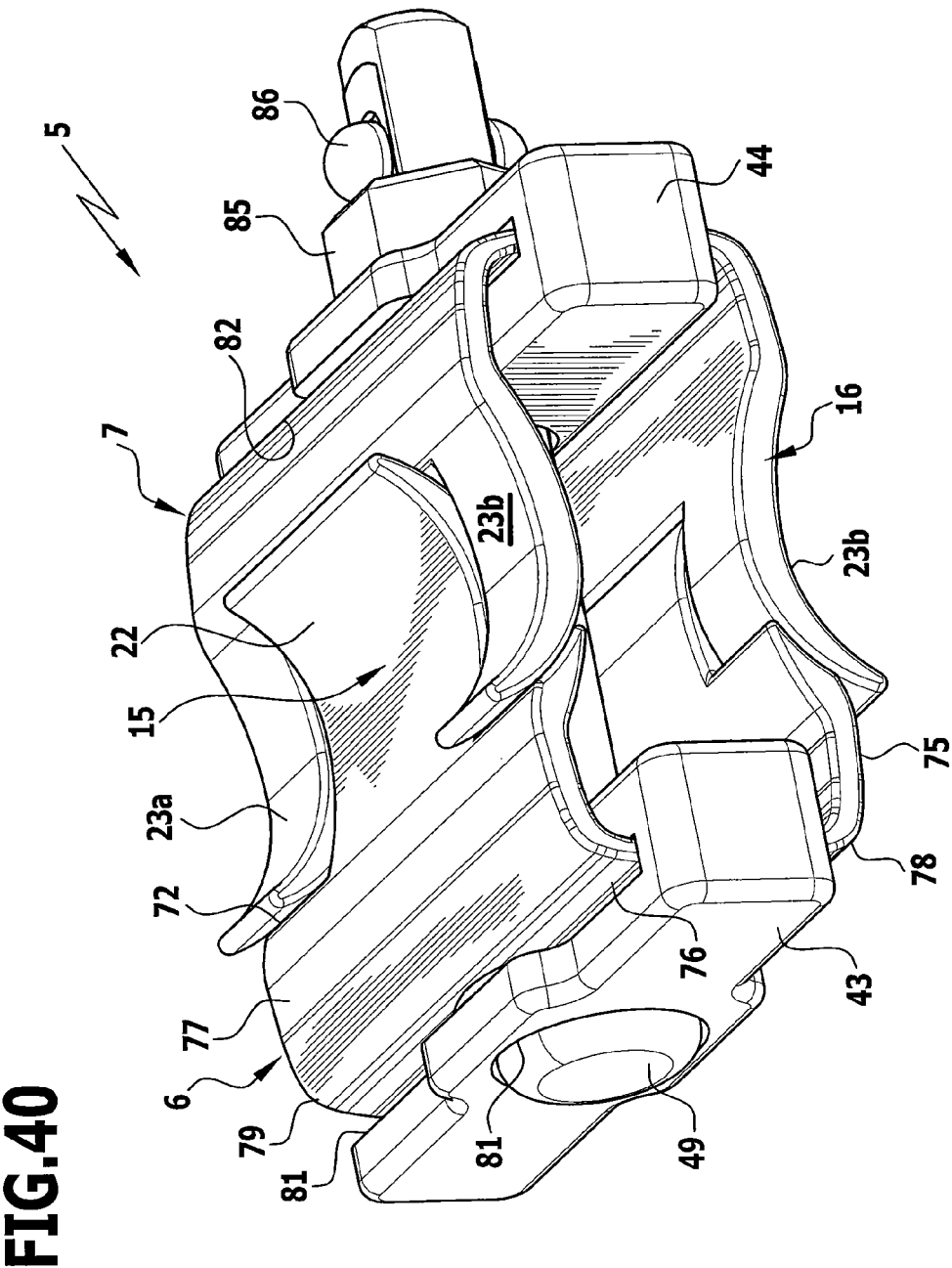
FIG. 40 is a perspective view of a further preferred embodiment of an implant.
Figure 41:
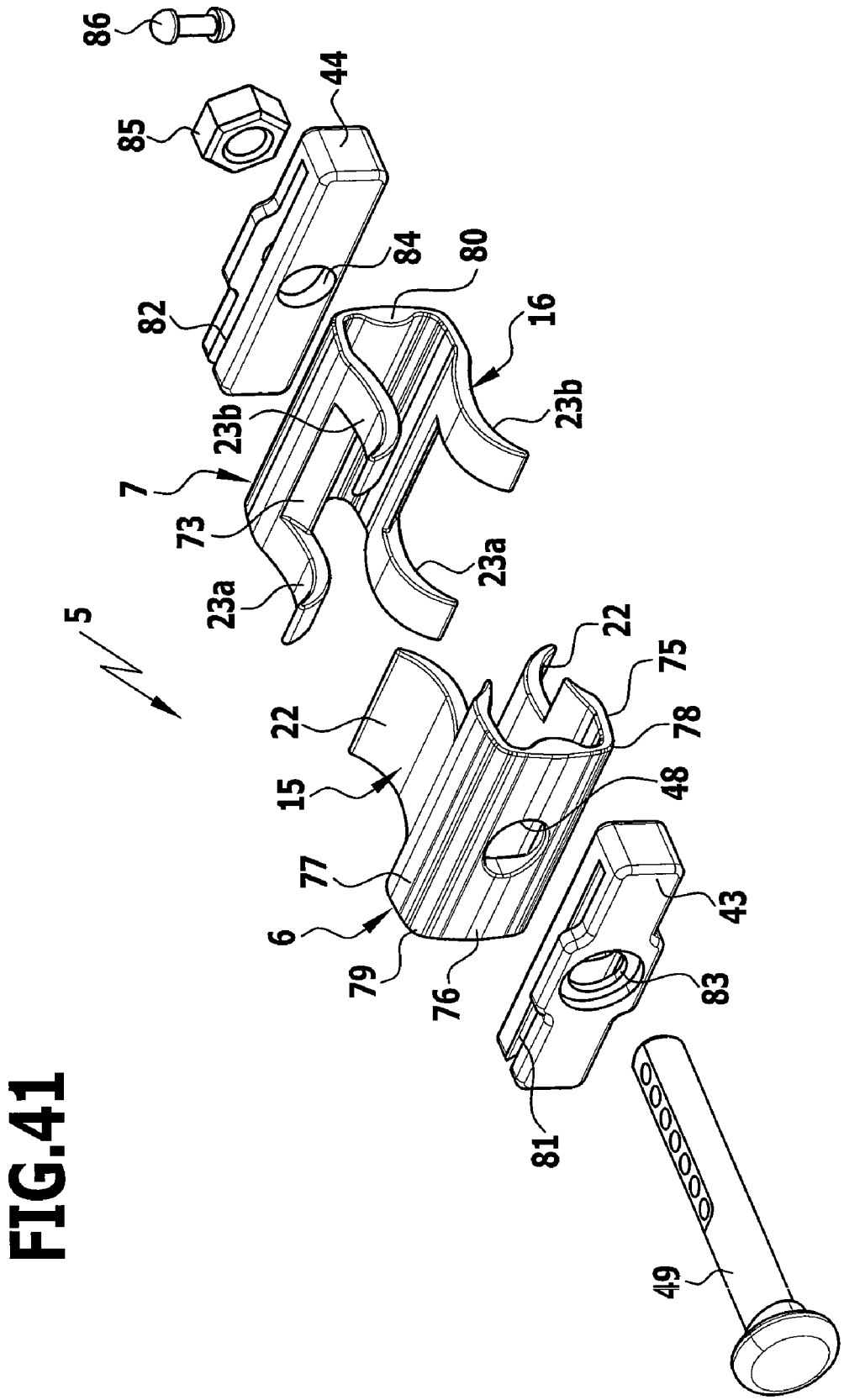
FIG. 41 is an exploded view of the implant of FIG. 40.

In the exemplary embodiment of FIGS. 40 and 41, the two implant components 6, 7 are clamped together by means of a tie bar 49, which acts on the outer surfaces of the implant components by means of bar-shaped end pieces 43, 44. In this case, these end pieces 43, 44 are fork-shaped with a longitudinal slot 81, 82 open from one side, and are slid laterally onto the implant components 6, 7 so that the bridge section 42 penetrates into the longitudinal slots 81 and 82 respectively, and this results in the end pieces 43 and 44 being reliably secured on the respective implant components 6, 7. In this case, the tie bar 49 engages through openings 83, 84 in the end pieces 43 and 44 respectively, and additionally through openings 48 in the two implant components 6, 7, and after they are clamped together, the position of the implant components 6, 7 is fixed by securing a nut 85 on the tie bar 49 in axial direction by a pin 86 passing through the tie bar 49.

Figure 42:
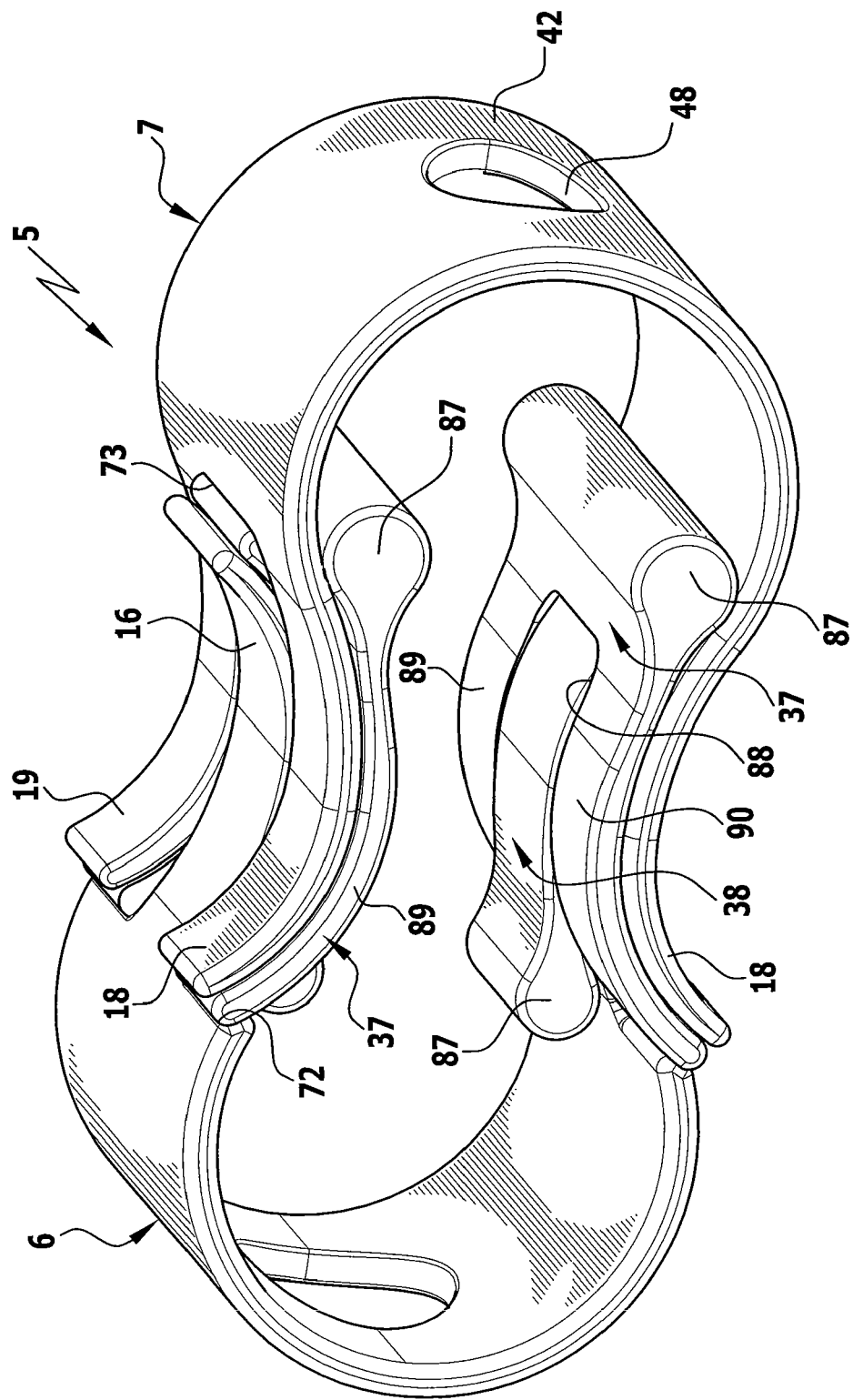
FIG. 42 is a perspective view of a further preferred exemplary embodiment of an implant with abutment elements abutting flat against the support arms.
Figure 43:
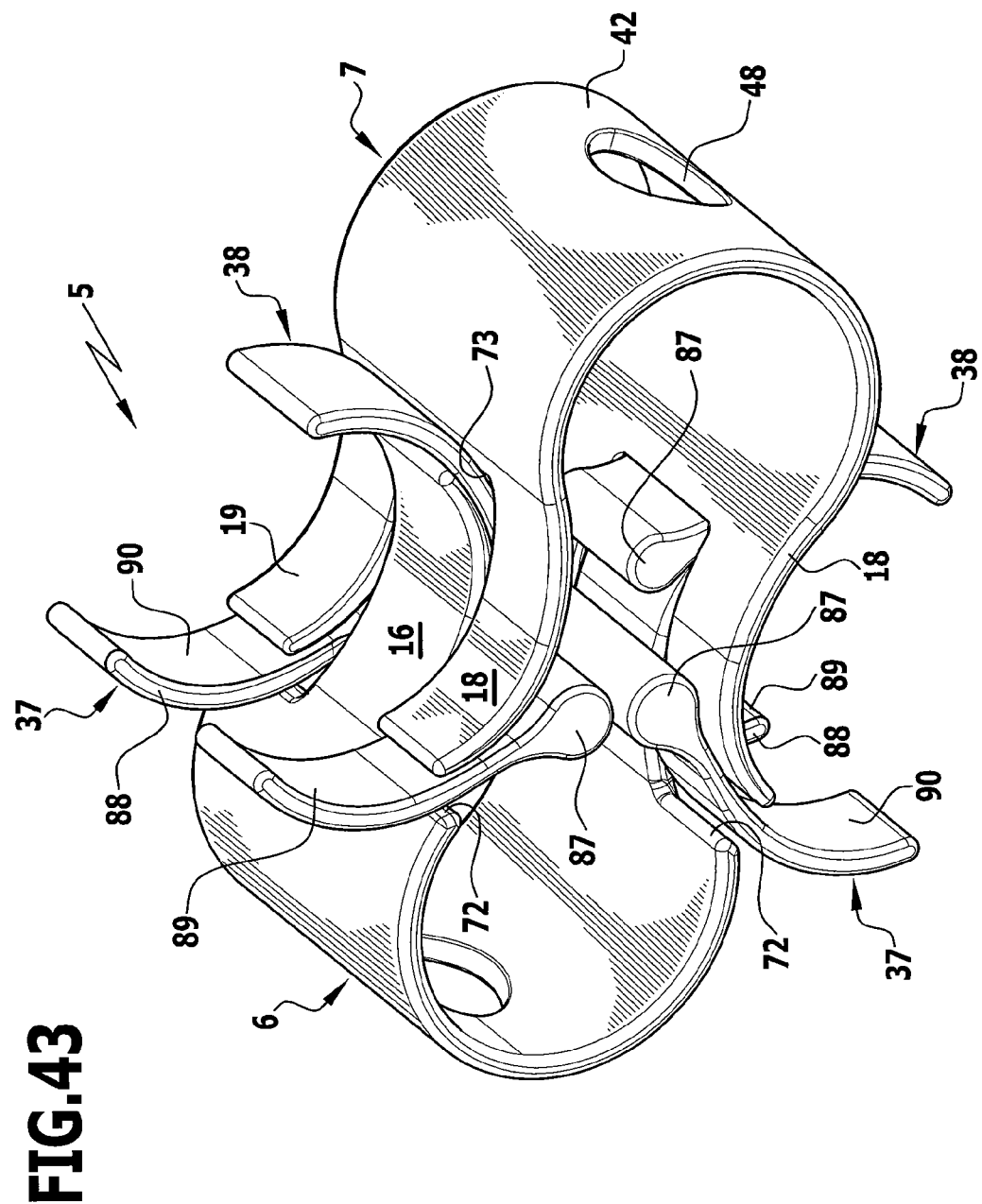
FIG. 43 is a perspective view of the implant of FIG. 42 after the implant components are pushed together and after the abutment elements are raised.
Figure 44:
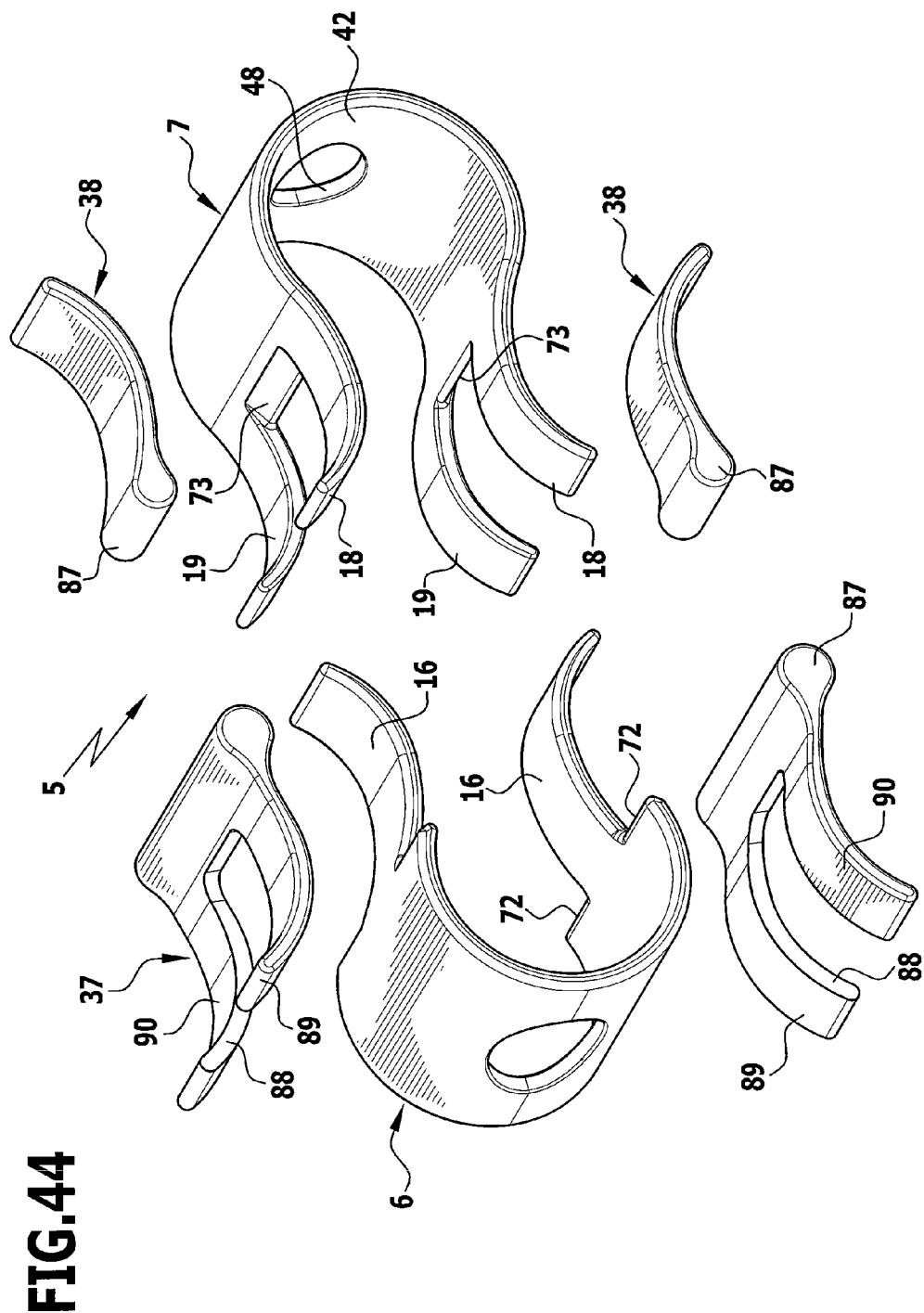
FIG. 44 is an exploded view of the implant of FIGS. 42 and 43.

An exemplary embodiment of an implant corresponding largely to that in FIGS. 33 and 34 is described in FIGS. 42 to 44. In addition to the two implant components 6, 7 band-like abutment elements 37, 38 are inserted respectively between the support arms of one implant component and the slide faces of the respective other implant component. These abutment elements are bent in a similar manner to the support arms and for insertion of an implant firstly abut flat against the support arms on the inner surface thereof. In this case, they terminate approximately with the free end of the support arms and bear a bead-shaped thickened area 87 on their opposite end. In this case the abutment elements correspond in their outer contours to the outer contours of the support arms, i.e. against the support arm 16, which is divided into two parallel support arm sections 18, 19 by a longitudinal slot 17, one abutment element 37 abuts, which is likewise divided into two parallel sections 89, 90 by a longitudinal slot 88, whereas the other abutment element, which abutments against the support arm 15 that is not divided, is likewise not divided.

After the insertion the band-like abutment elements can be removed in their longitudinal direction from the interstice that they fill between the support arms 15, 16, on one side, and the slide faces 72, 73, on the other side, and thus are raised at their free ends, i.e. they project substantially transversely from the upper side of the implant components 6, 7 and on both sides of the support surfaces 22, 23 formed by the outer surfaces of the support arms in the region adjoining the other free end. As a result of the bead-like thickened area 87, the extension length of the abutment elements is restricted, so that it is easily possible for the surgeon to pull these abutment elements out as far as their stop and thus secure the implant relative to the spinous process in the above-described manner.

Figure 45:
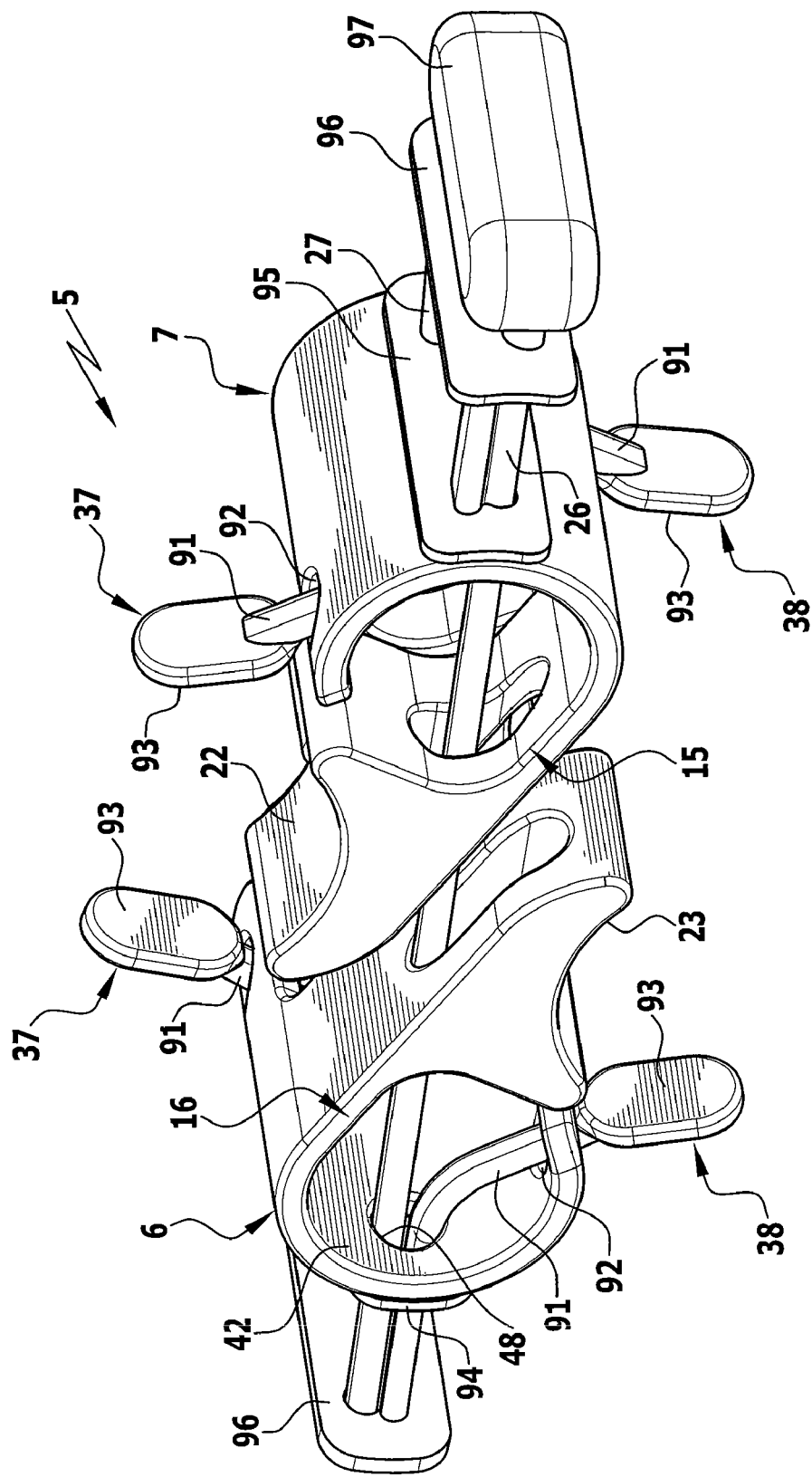
FIG. 45 is a perspective view of a further preferred exemplary embodiment of an implant before the implant components are pushed together.
Figure 46:
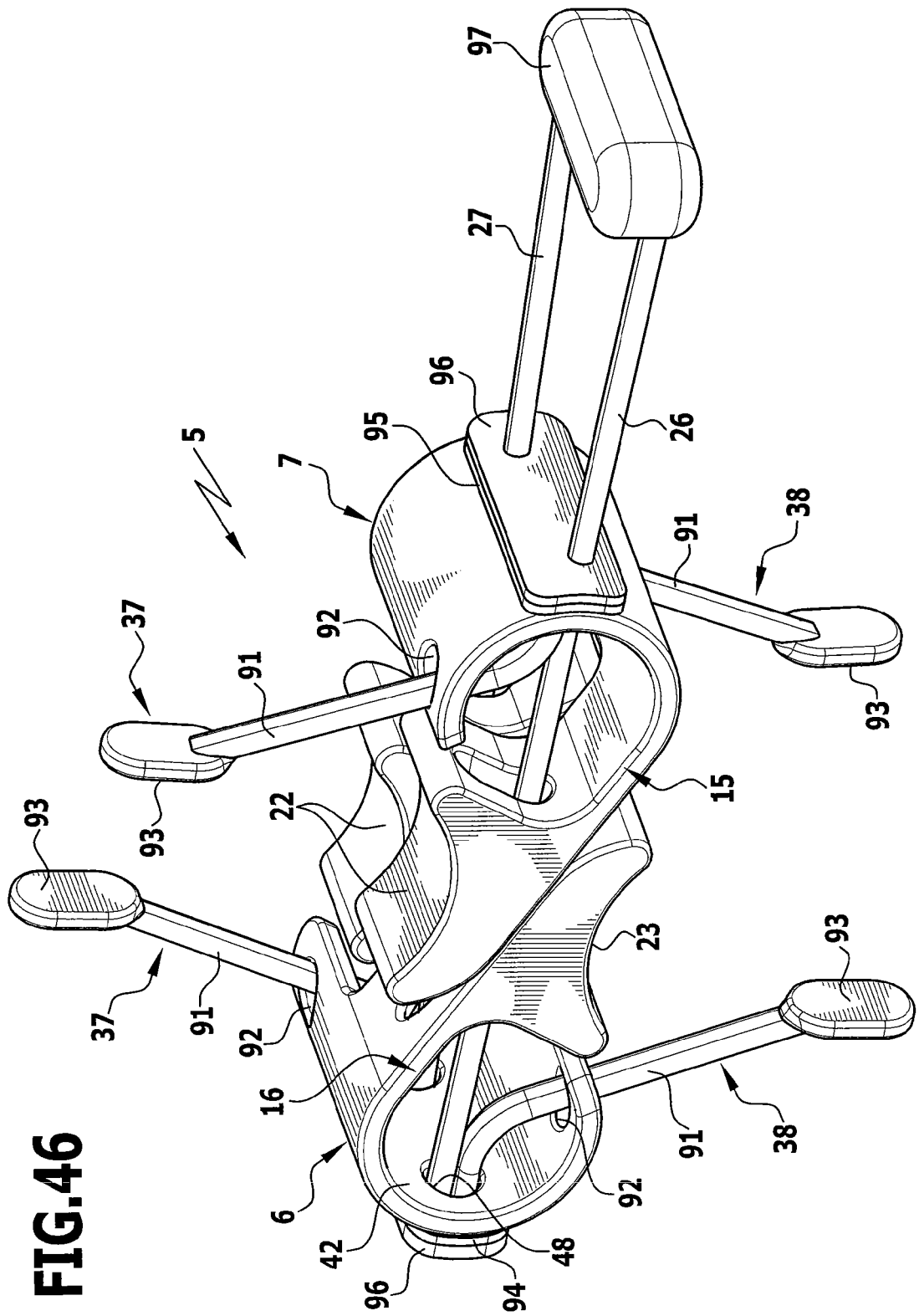
FIG. 46 is a perspective view of the implant of FIG. 45 after the two implant components are pushed together.
Figure 47:
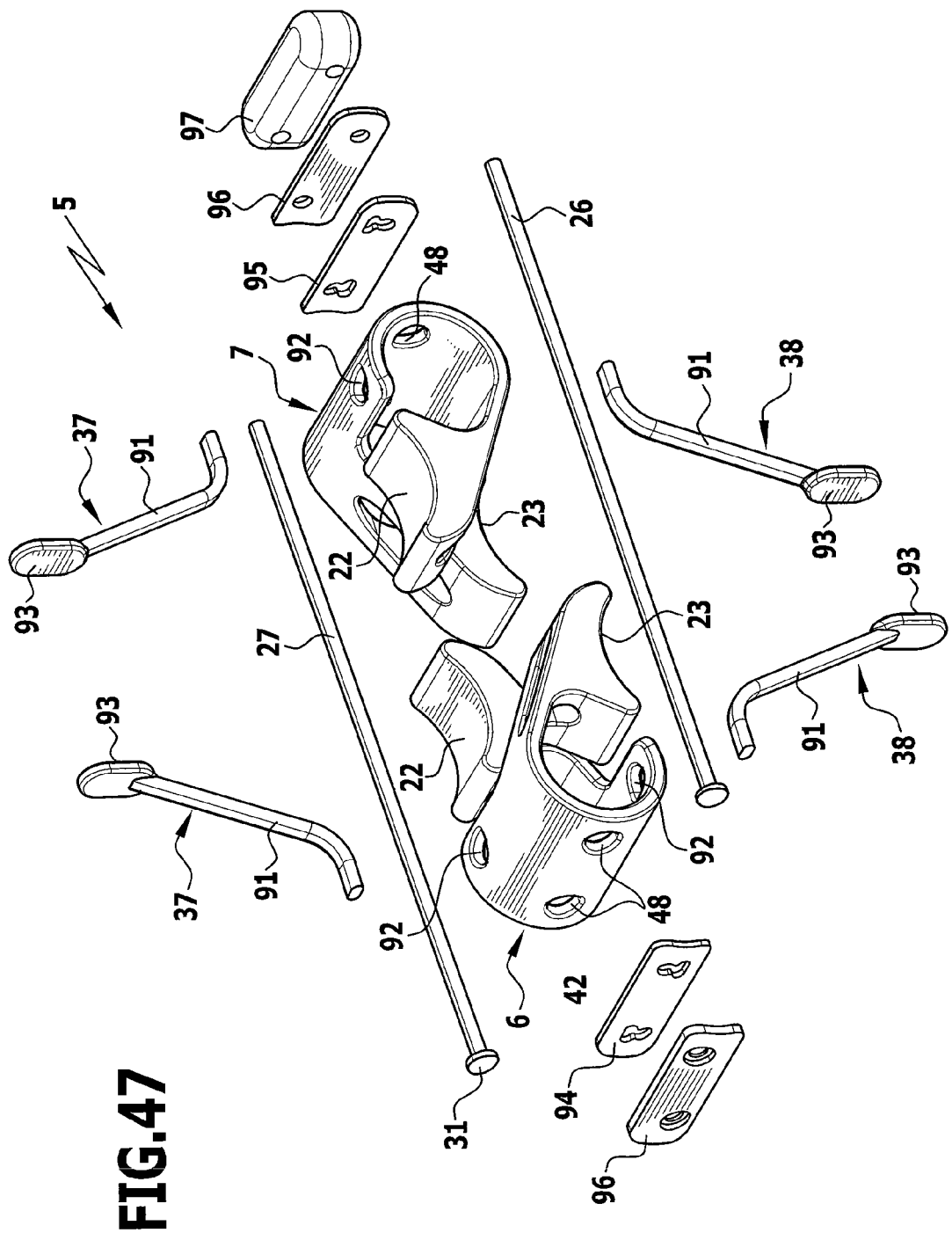
FIG. 47 is an exploded view of the implant of FIGS. 45 and 46.

In FIGS. 45 to 47 an implant, in which the implant components 6, 7 correspond to the implant components of FIGS. 22 and 23, is described. In place of the abutment elements used there in the form of coil springs, however, in the exemplary embodiment of FIGS. 45 to 47 special abutment elements 37, 38 are provided that substantially comprise a flexible bar-shaped support 91, which, starting from the centre of the bridge section 42, firstly enters the interior, i.e. parallel to the centre plane or displacement plane of the implant components, and then after strong angling off exits to the outside through an opening 92 in the end region of the respective bridge section 42. In this case, each implant component 6, 7 bears two such abutment elements, which exit from the implant component to opposite sides, wherein all the supports 51 bear an enlarged abutment surface 93 on their free end.

The supports 91 are not fixed on the bridge section 42, but pass through this through openings 48 of the bridge section 42, through which tie bars 26 and 27 are also guided. Outside the implant components 6, 7 on opposite sides thereof, two cross members 94, 95 are disposed to be longitudinally displaceable on these tie bars 26, 27, and two abutment elements 37, 38 are fixed at their supports 91 on each of these cross members 94, 95.

The two tie bars 26, 27 are connected at their ends by means of two bridge-shaped webs 96, 97, the spacing of which is firstly larger than the spacing of the implant components 6, 7 when in the pushed together state.

In this way, it is possible to displace the cross members 94, 95 along the tie bars 26, 27 and thus also move them away from the bridge sections 42. This causes the flexible supports 91 to be displaced in the openings 48 and 92, these openings acting as a guide in the case of such a displacement. If the supports 91 are displaced towards the respective implant components 6, 7 as a result of the cross members 94, 95 approaching the bridge section 42, this causes their ends bearing the abutment surface 93 to be pushed laterally further out of the implant components 6, 7, and then these pushed out supports with the abutment surfaces 93 abut laterally against the spinous processes, and in this way secure the implant relative to the vertebral bodies.

Therefore, when the implant components 6, 7 are clamped against one another after insertion as a result of displacement of the web 97 on the tie bars 26, 27, this simultaneously causes the cross members 94, 95 to be displaced towards the implant components and the supports 91 of the abutment elements 37, 38 to be extended. In this state, the individual parts can be fixed in their attained position by securing the web 97 on the tie bars 26, 27.

Figure 48:
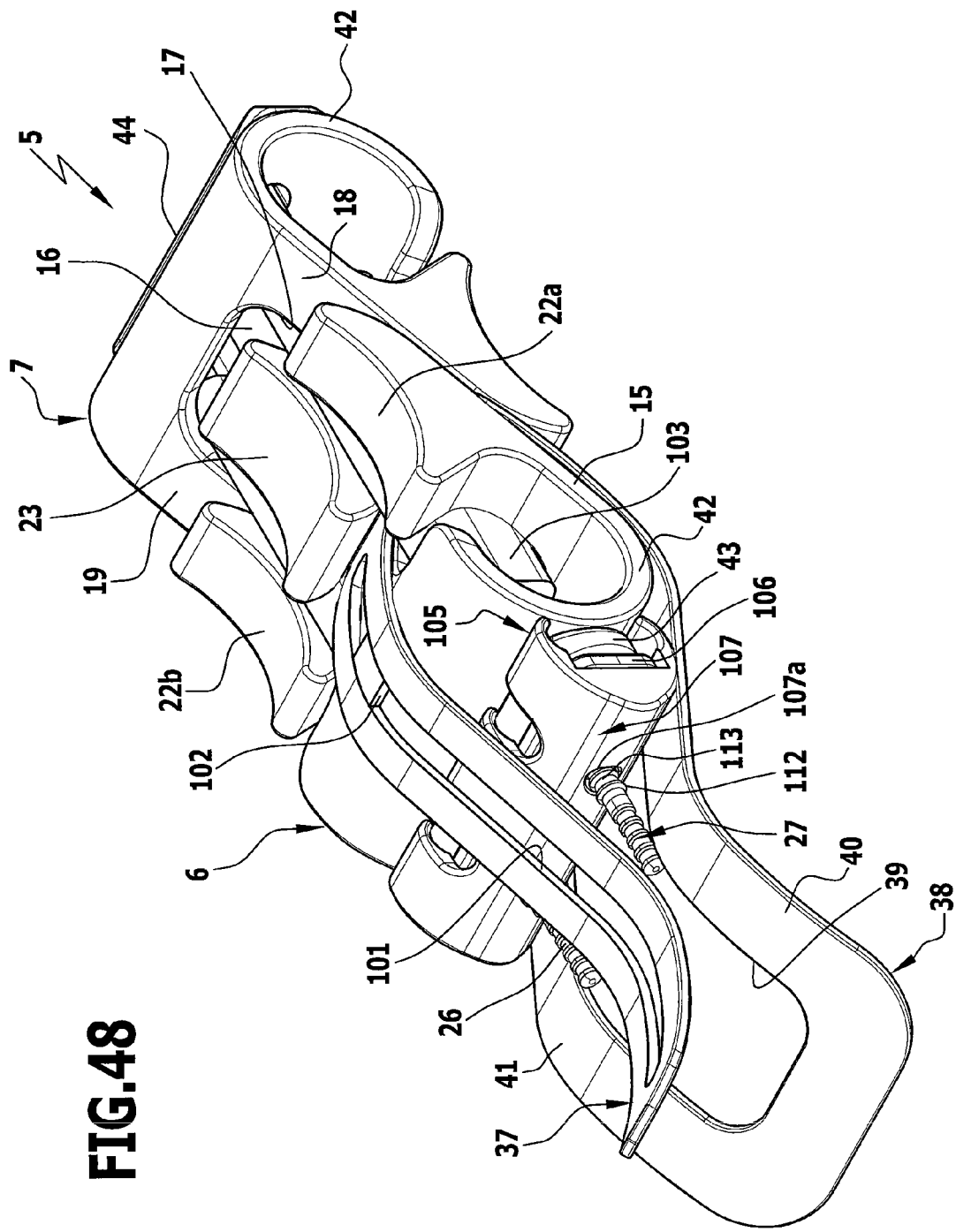
FIG. 48 is a perspective view of a further preferred exemplary embodiment of an implant after the implant components have been pushed together.
Figure 49:
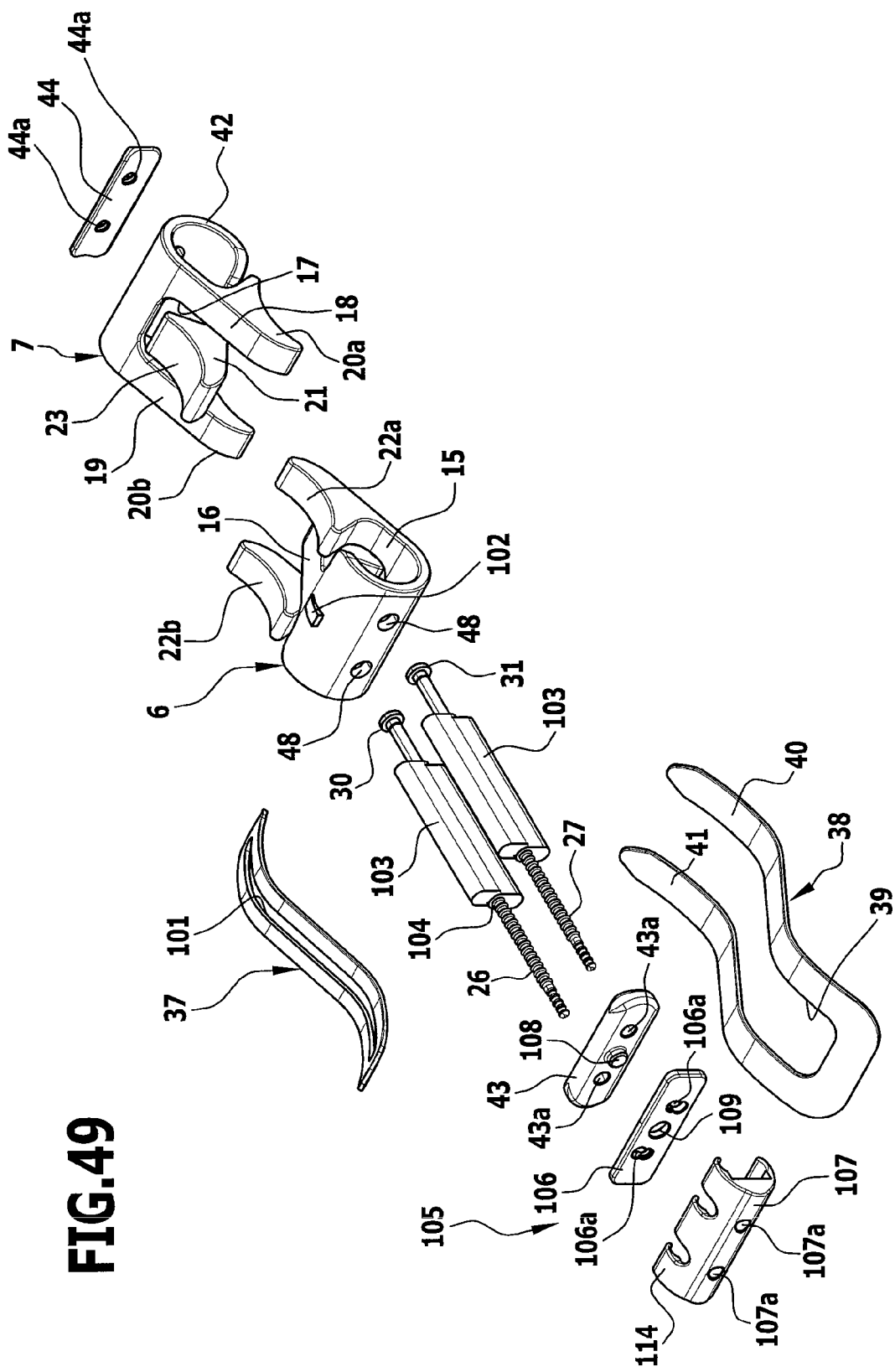
FIG. 49 is an exploded view of the implant of FIG. 48.

A further preferred exemplary embodiment of an implant is shown in FIGS. 48 and 49. This comprises implant components 6, 7, which correspond substantially to those of the exemplary embodiment of FIGS. 7 to 9, and corresponding parts have been given the same reference numerals. The abutment elements 37 and 38 are also similar in configuration to those in the exemplary embodiment of FIGS. 7 to 9, and corresponding parts have likewise been given the same reference numerals here.

In contrast to the exemplary embodiment of FIGS. 7 to 9, the band-shaped narrow abutment element 37 has a longitudinal slot 101, which extends over the largest portion of its length and into which a guide projection 102 arranged on the outer surface of the implant component 6 and configured to be so wide that it abuts against the two side edges of the longitudinal slot 101, engages when the abutment element 37 is inserted between the two implant components 6, 7. As a result, when the abutment element 37 is inserted between the two implant components 6, 7, the abutment element 37 is guided so that the user is assisted during insertion of the abutment element 37 and is given a guide to the advancing direction.

A similar guidance by means of a longitudinal slot and a guide projection can also occur in the other exemplary embodiments for the abutment element 37 and also for abutment element 38. In the case of abutment element 38 a relatively wide longitudinal slot 39 is provided, and other parts of the implant components can abut against its side edges in a guided manner, e.g. two tie bars 26, 27 or other parts of the implant components passing through the two implant components 6, 7.

In the exemplary embodiment of the implant according to FIGS. 48 and 49, the two implant components 6, 7 are clamped together by two adjacent tie bars 26, 27, which are passed through openings 48 in the bridge sections 42 of the two implant components. These tie bars 26, 27 respectively have a head 30, 31 at one end and are passed through openings 44a of a plate-shaped end piece 44, which can abut against the outer surface of the bridge section 42 of the implant component 7. A respective guide bar 103 is attached to both tie bars 26, 27, these guide bars 103 abut against the inner edges of the longitudinal slot 39 of the abutment element 38 and guide this during the longitudinal displacement, i.e. during insertion between the two implant components 6, 7. In this case, the guide bars 103 have a receiving channel 104, which extends through in the longitudinal direction and through which the tie bars 26, 27 engage.

On the side opposite the end piece 44, the tie bars 26, 27 exit through openings 48 in the implant components 6, and in this region a likewise plate-shaped end piece 43 is also pushed onto the two tie bars 26, 27 and has two openings 43a adjacent to one another, through which the tie bars 26, 27 pass.

The two implant components 6, 7 can be clamped against one another by moving the two end pieces 43 and 44 closer. To secure these implant components in the position where they are clamped against one another, a locking means 105 is provided, which comprises a plate-shaped locking element 106 and a cap 107, which can be attached to the end piece 43. Between the two openings 43a the end piece 43 bears a central locating stud 108, which engages into a central locating opening 109 of the locking plate 106, so that the locking plate 106 is disposed on the plate-shaped end piece 43 to pivot around the rotational axis formed by the locating stud 108.

Openings 106a, which are aligned with the openings 43a of the end piece 43, are arranged on both sides of the locating opening 109 in the locking plate 106. As can be seen in particular from FIGS. 52 and 53, the opening 106a is divided into two adjacent sections, namely a first section 110 with a larger diameter and a second section 111, the diameter of which is smaller, for example, an inwardly projecting shoulder or rib can be arranged in the second section 111, by means of which the diameter is reduced.

The tie bars 26 and 27 bear spaced peripheral ribs 112, which run transversely to the longitudinal direction and between which annular groove-shaped recessed areas 113 are thus formed. The diameters of the first section 110 and the second section 111 are selected so that with their peripheral ribs 112 the tie bars 26, 27 can be pushed in axial direction through the first sections 110, but the cross-section of the second sections 111 is smaller and no longer allows the peripheral ribs 112 to be pushed through so freely. In contrast, the cross-section of the second section 111 is so large that the tie bars 26, 27 can enter this second section 111 with the region lying between the peripheral ribs 112, i.e. with the groove-shaped recessed area 113. This causes the peripheral ribs 112 arranged next to the respective recessed area 113 to abut either against both outer surfaces of the locking plate 106 or against both side faces of a shoulder or rib reducing the cross-section of the second section 111, and as a result of this the locking plate 106 and the two tie bars 26, 27 are secured against axial displacement of the tie bars 26, 27 relative to the locking plate 106.

Thus, as a result of a pivoting movement of the locking plate 106 relative to the end piece 43 and thus relative to the tie bars 26, 27 projecting through the end piece 43, the locking plate 106 can be pivoted from a locking position into a release position and vice versa, wherein in a release position the tie bars 26, 27 pass through the first section 110 of the locking plate 106, but in the locking position pass through the second section 111. Thus, during clamping the locking plate 106 is firstly held in the release position pivoted relative to the end piece 43 (FIG. 52), and in this position the two end pieces 43, 44 can be readily clamped against one another, this naturally also applying to the locking plate 106 that abuts against the end piece 43 and is disposed to pivot on this end piece 43 by means of the locating stud 108. As soon as the two end pieces 43, 44 have been pushed together sufficiently, the locking plate 106 is pivoted into the locking position shown in FIG. 53, and the tie bars 26, 27 thus enter the second section 111 of the openings 106a and therefore prevent the locking plate 106 and with it also the end piece 43 from being able to shift along the tie bars 26, 27.

As soon as this locking has been achieved, the cap 107 is pushed over the locking plate 106 and the end piece 43, wherein the cap 107 engages over both the locking plate 106 and the end piece 43 with lateral arms 114. The arms 114 are preferably configured to be elastic, so that the cap 107 is held elastically on the end piece 43 and the locking plate 106 in the manner shown in FIG. 48. In this case, the cap 107 can have two openings 107a, through which the ends of the tie bars 26, 27 pass.

Figure 50:
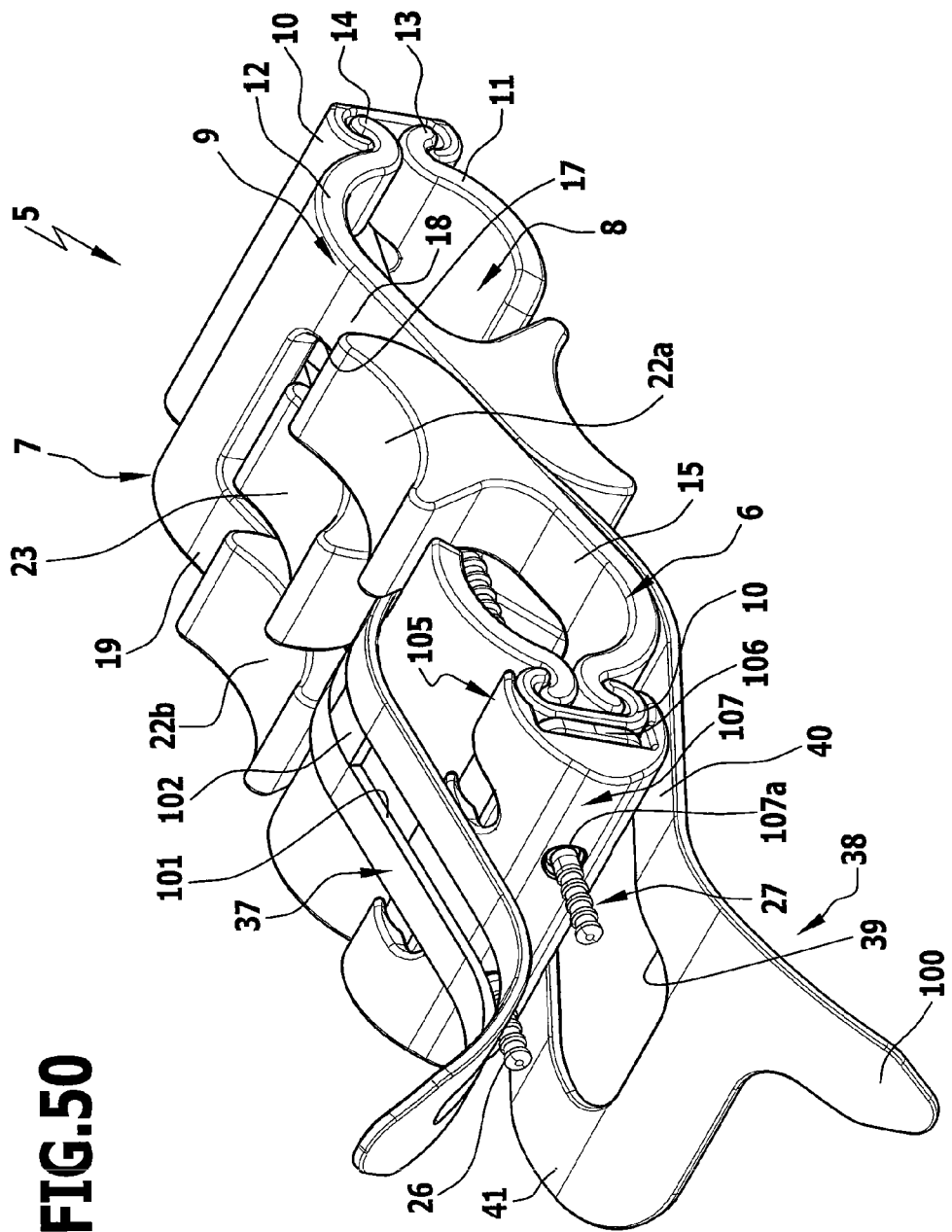
FIG. 50 is a perspective view of a further preferred exemplary embodiment of an implant after the implant components have been pushed together.
Figure 51:
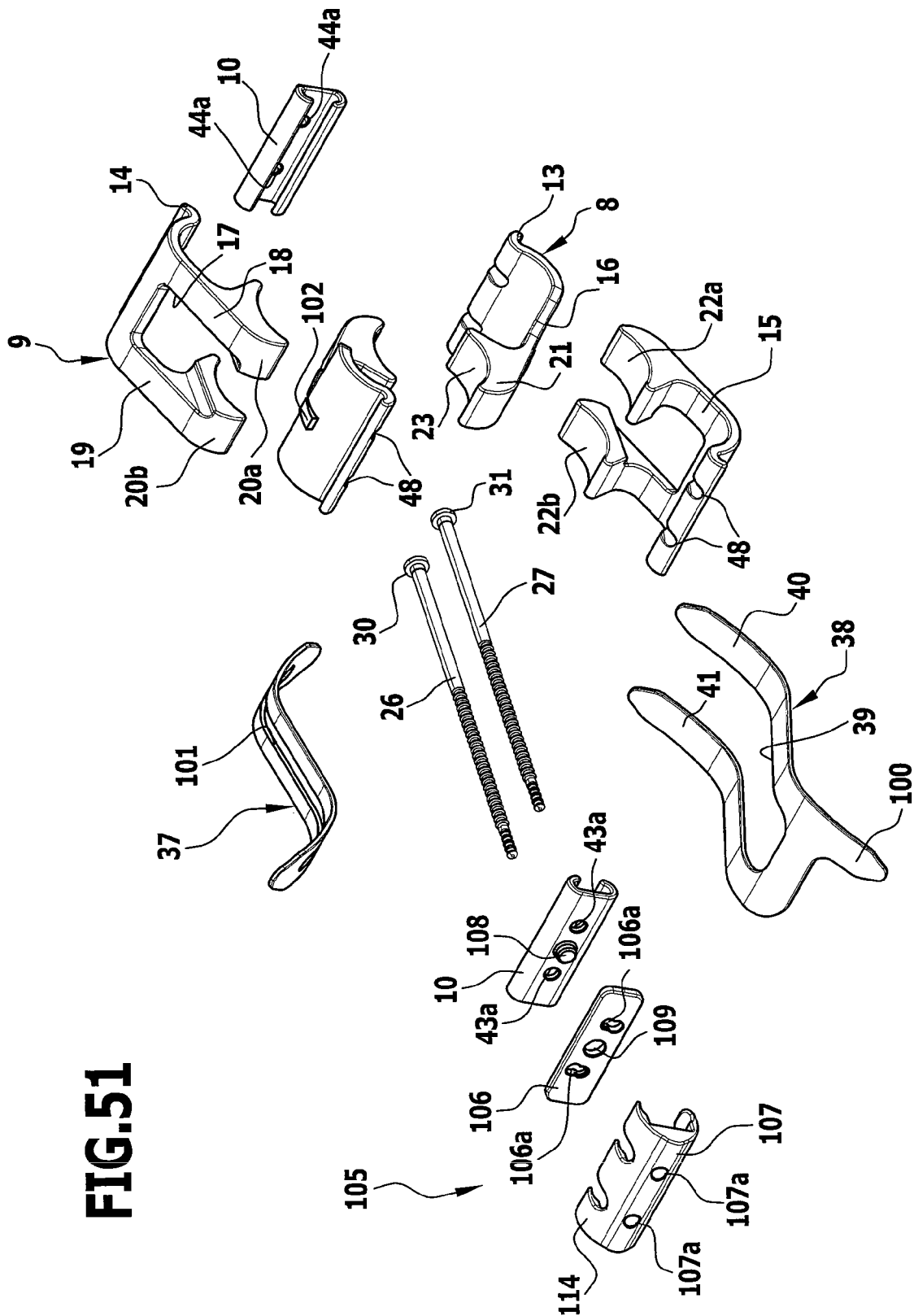
FIG. 51 is an exploded view of the implant of FIG. 50.
Figure 52:
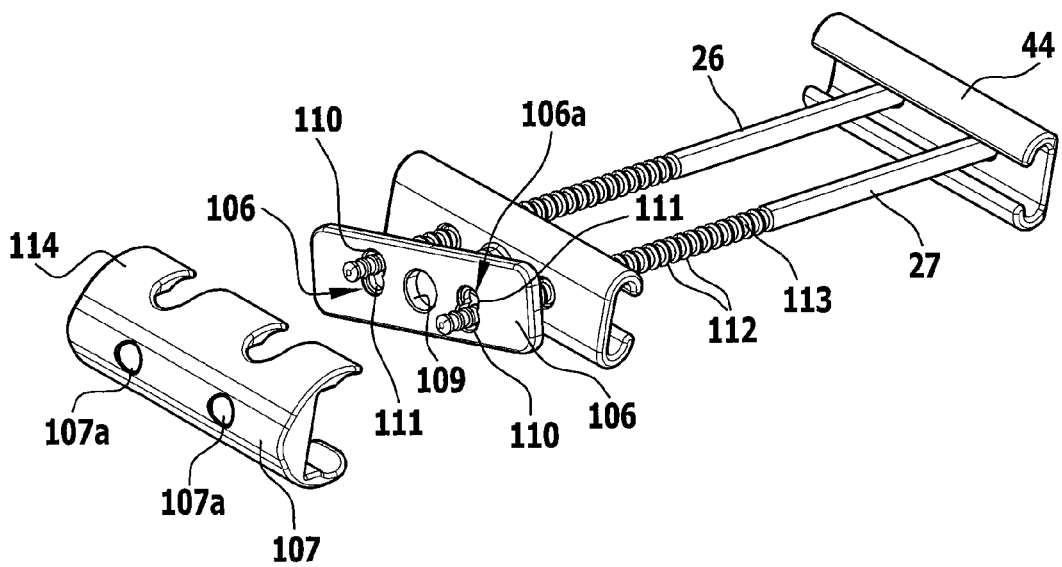
FIG. 52 is a perspective view of the tie rods and the locking means for the tie bars in the exemplary embodiments of FIGS. 48 to 51 before locking of the tie bars.
Figure 53:
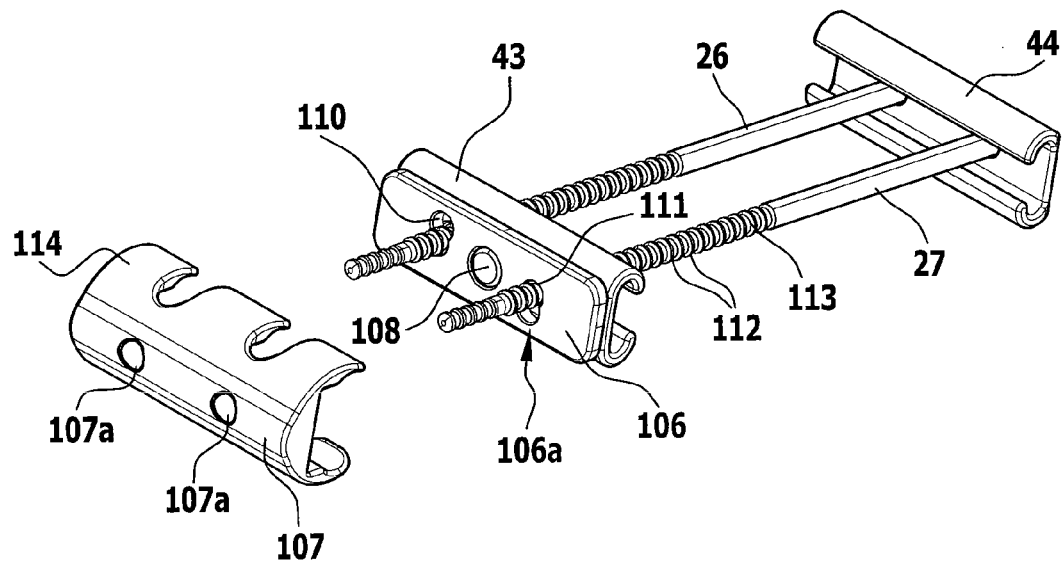
FIG. 53 is a view similar to FIG. 52 after the tie bars are locked and before the locking element is secured.

A very similar configuration overall is selected in the case of the exemplary embodiment of FIGS. 50 and 51, but in a similar manner to that in the exemplary embodiment of FIGS. 3 to 6, the two implant components 6, 7 are respectively composed of two structural parts 8, 9, which are held together in the same way by clamps 10. These clamps 10 thus assume the task of the end pieces 43 and 44 and, regardless of their function of holding together the structural parts 8, 9, are configured substantially the same as the end pieces 43 and 44 in the exemplary embodiment of FIGS. 48 and 49. Consequently, the locking means 105 also functions in the same manner.

In the exemplary embodiment of FIGS. 50 and 51, on one of its webs 40 the abutment element 38 bears an extension 100, which facilitates the insertion. Such an extension can also be provided on the abutment element 38 in the other exemplary embodiments.

What is claimed is:

1. An implant for mutual support of the spinous processes of two adjacent vertebral bodies with an upper support surface for the spinous process of an upper vertebral body and a lower support surface for the spinous process of a lower vertebral body, the spacing between which can be increased, wherein it comprises two implant components, each of which having at least two adjacent support arms, which are connected to one another at one end by means of a bridge and can be spread apart at their free ends, and at least one of which support arms forms one of the support surfaces, with the free ends of their support arms both implant components are directed towards the free ends of the support arms of the respective other implant component, and both implant components slide on slide faces of the respective other implant component, and are pivoted thereby, so that the spacing of the upper and lower support surfaces is thereby increased, wherein the support arms of one implant component run inclined relative to one another, starting from the bridge connecting them, that they cross over one another and that the support arms slide on the slide faces of the other implant component with their outer surfaces and are thereby inclined even more steeply relative to one another, wherein as a result of the crossover of the support arms the free ends of the support arms are moved away from one another.

2. The implant according to claim 1, wherein the support surfaces are concavely curved, so that when the spinous process is supported in the centre portion of a support surface, this rises at its edge regions on both sides of the spinous process.

3. The implant according to claim 1, wherein each implant component has a respective support surface on its two support arms, so that each implant component forms a part of the upper support surface and a part of the lower support surface.

4. The implant according to claim 1, wherein at least one support arm of an implant component is divided into two adjacent support arm sections by a longitudinal slot starting at its free end.

5. The implant according to claim 4, wherein support arms or support arm sections of one implant component are arranged in the longitudinal slot between support arm sections of the other implant component.

6. The implant according to claim 1, wherein at least one support arm bears a support surface on its inner surface.

7. The implant according to claim 1, wherein the outer surface of a support arm of one implant component forms the slide face for a support arm of the other implant component.

8. The implant according to claim 1, wherein both implant components of an implant are configured identically.

9. The implant according to claim 1, wherein an implant component consists of two individual parts, which are connected to one another in a hinge-like manner in the region of the bridge.

10. The implant according to claim 9, wherein on their ends abutting one another both individual parts respectively bear a locating bead, which run next to one another and are jointly embraced by a clamp and are thereby held next to one another.

11. The implant according to claim 1, wherein the implant component is made from an elastically deformable material.

12. The implant according to claim 1, wherein in the region of the bridge the implant component has at least one through opening for a tie bar pushing the two implant components towards one another.

13. The implant according to claim 1, wherein at least one tie bar, which clamps the two implant components against one another, engages through the implant components.

14. The implant according to claim 13, wherein the tie bar has alternating projections and recessed areas and a locking element, which can engage between adjacent projections, is disposed on the implant.

15. The implant according to claim 14, wherein the locking element has an opening for the tie bar with two adjacent regions, a first region of which is large enough that the tie bar can be pushed freely in an axial direction through this first region with its projections, whereas the second region is only large enough that a section of the tie bar lying between adjacent projections can be inserted into it, while a section bearing a projection cannot.

16. The implant according to claim 15, wherein the locking element can pivot around an axis running parallel to the longitudinal axis of the tie bar.

17. The implant according to claim 14, wherein the projections are configured as peripheral ribs.

18. The implant according to claim 14, wherein the locking element can be fixed in a position, in which it engages between adjacent projections of the tie bar.

19. The implant according to claim 18, wherein to fix the locking element in position a cap is provided, which can be attached to the locking element and a holding element, which is arranged adjacent to this and is held on the tie bar, to engage around the locking element and the holding element.

20. The implant according to claim 19, wherein the holding element and the locking element are disposed on one another to be able to pivot relative to one another.

21. The implant according to claim 1, wherein lateral abutment elements for the spinous process resting on the support surface are arranged on the implant next to the support surfaces.

22. The implant according to claim 21, wherein as the two implant components approach one another, the abutment elements are movable or deformable by relative movement of the two implant components from a starting position, in which they project little or not at all from the implant components, into an end position, in which they project to a greater extent from the implant component.

23. The implant according to claim 21, wherein the abutment elements are separate parts, which are respectively held on the implant component.

24. The implant according to claim 23, wherein the abutment elements are held in a wedge fit between the support arms of one implant component and the slide face of the other implant component.

25. The implant according to claim 24, wherein the abutment elements are in the form of bands.

26. The implant according to claim 25, wherein at least one abutment element has a longitudinal slot.

27. The implant according to claim 26, wherein a part of an implant component projects into the longitudinal slot and abuts against the side edges of the longitudinal slot.

28. The implant according to claim 24, wherein the abutment elements are bent to opposite sides on opposite ends.

29. An implant for mutual support of the spinous processes of two adjacent vertebral bodies with an upper support surface for the spinous process of an upper vertebral body and a lower support surface for the spinous process of a lower vertebral body, the spacing between which can be increased, wherein it comprises two implant components, each of which having at least two adjacent support arms, which are connected to one another at one end by means of a bridge and can be spread apart at their free ends, and at least one of which support arms forms one of the support surfaces, with the free ends of their support arms both implant components are directed towards the free ends of the support arms of the respective other implant component, and both implant components slide on slide faces of the respective other implant component, and are pivoted thereby, so that the spacing of the upper and lower support surfaces is thereby increased, wherein at least one tie bar, which clamps the two implant components against one another, engages through the implant components, wherein the tie bar has alternating projections and recessed areas and a locking element, which can engage between adjacent projections, is disposed on the implant, and wherein the locking element has an opening for the tie bar with two adjacent regions, a first region of which is large enough that the tie bar can be pushed freely in an axial direction through this first region with its projections, whereas the second region is only large enough that a section of the tie bar lying between adjacent projections can be inserted into it, while a section bearing a projection cannot.

30. The implant according to claim 29, wherein the projections are configured as peripheral ribs.

31. The implant according to claim 29, wherein the locking element can pivot around an axis running parallel to the longitudinal axis of the tie bar.

32. The implant according to claim 29, wherein the locking element can be fixed in a position, in which it engages between adjacent projections of the tie bar.

33. The implant according to claim 32, wherein to fix the locking element in position a cap is provided, which can be attached to the locking element and a holding element, which is arranged adjacent to this and is held on the tie bar, to engage around the locking element and the holding element.

34. The implant according to claim 33, wherein the holding element and the locking element are disposed on one another to be able to pivot relative to one another.

35. An implant for mutual support of the spinous processes of two adjacent vertebral bodies with an upper support surface for the spinous process of an upper vertebral body and a lower support surface for the spinous process of a lower vertebral body, the spacing between which can be increased, wherein it comprises two implant components, each of which having at least two adjacent support arms, which are connected to one another at one end by means of a bridge and can be spread apart at their free ends, and at least one of which support arms forms one of the support surfaces, with the free ends of their support arms both implant components are directed towards the free ends of the support arms of the respective other implant component, and both implant components slide on slide faces of the respective other implant component, and are pivoted thereby, so that the spacing of the upper and lower support surfaces is thereby increased, wherein lateral abutment elements for the spinous process resting on the support surface are arranged on the implant next to the support surfaces, wherein the abutment elements are separate parts, which are respectively held on the implant component, and wherein the abutment elements are held in a wedge fit between the support arms of one implant component and the slide face of the other implant component.

36. The implant according to claim 35, wherein as the two implant components approach one another, the abutment elements are movable or deformable by relative movement of the two implant components from a starting position, in which they project little or not at all from the implant components, into an end position, in which they project to a greater extent from the implant component.

37. The implant according to claim 35, wherein the abutment elements are bent to opposite sides on opposite ends.

38. The implant according to claim 35, wherein the abutment elements are in the form of bands.

39. The implant according to claim 38, wherein at least one abutment element has a longitudinal slot.

40. The implant according to claim 39, wherein a part of an implant component projects into the longitudinal slot and abuts against the side edges of the longitudinal slot.

* * * * *